United States Patent
Breitenkamp et al.

(10) Patent No.: US 8,212,083 B2
(45) Date of Patent: Jul. 3, 2012

(54) HETEROBIFUNCTIONAL POLY(ETHYLENE GLYCOL) CONTAINING ACID-LABILE AMINO PROTECTING GROUPS AND USES THEREOF

(75) Inventors: Kurt Breitenkamp, Tampa, FL (US); Kevin N. Sill, Tampa, FL (US); Habib Skaff, Tampa, FL (US)

(73) Assignee: Intezyne Technologies, Inc., Tampa, FL (US)

( * ) Notice: Subject to any disclaimer, the term of this patent is extended or adjusted under 35 U.S.C. 154(b) by 1040 days.

(21) Appl. No.: 11/796,392

(22) Filed: Apr. 27, 2007

(65) Prior Publication Data

US 2008/0188638 A1 Aug. 7, 2008

Related U.S. Application Data

(60) Provisional application No. 60/795,374, filed on Apr. 27, 2006.

(51) Int. Cl.
*C07C 205/00* (2006.01)

(52) U.S. Cl. ........ 568/583; 568/300; 568/557; 568/579; 564/269; 544/65; 560/160

(58) Field of Classification Search ........................ None
See application file for complete search history.

(56) References Cited

U.S. PATENT DOCUMENTS

| | | | |
|---|---|---|---|
| 5,483,008 | A | 1/1996 | Sakurai et al. |
| 5,925,720 | A | 7/1999 | Kataoka et al. |
| 6,388,041 | B1 | 5/2002 | Kataoka et al. |
| 6,448,369 | B1 | 9/2002 | Bentley et al. |
| 2006/0142506 | A1 | 6/2006 | Breitenkamp et al. |
| 2006/0172914 | A1 | 8/2006 | Breitenkamp et al. |
| 2006/0240092 | A1 | 10/2006 | Breitenkamp et al. |
| 2008/0207913 | A1 | 8/2008 | Breitenkamp et al. |

FOREIGN PATENT DOCUMENTS

FR 125975 A1 * 11/1984

OTHER PUBLICATIONS

Li et al, Biomacromolecules, 2003, 4, 1055-1067.*
Sauvagnat et al, Tetrahedron Letters, 1998, 39(8), 821-824.*
Akiyama, Y. et. al., Synthesis of Poly(ethylene glycol)-block-poly(ethylenimine) Possessing an Acetal Group at the PEG End, Macromolecules, 33:5841-5845 (2000).
Akiyama, Y. et. al., Synthesis of Heterotelechelic Poly(ethylene glycol) Derivatives Having alpha-Benzaldehyde and omega-Pyridyl Disulfide Groups by Ring Opening Polymerization of Ethylene Oxide Using 4-(Diethoxymethyl)benzyl Alkoxide as a Novel Initiator, Bioconjugate Chemistry, 15:424-427 (2004).
Fauq, Synthesis of Acid-Cleavable Light Isotope-Coded Affinity Tag (ICAT-L) for Potential Use in Proteomic Expression Profiling Analysis, Bioconjugate Chemistry, 17(1):248-254 (2006).
Glaied, O. et. al., Oxazoline-Terminated Macromonomers by the Alkylation of 2-Methyl-2-oxazoline, Journal of Polymer Science Part A, 43:2440-2447 (2005).
Huang, Y. et. al., The Kinetics of the Attachment of Polymer Chains to Reactive Latex Particles and the Resulting Latex Stabilization, Journal of Polymer Science: Polymer Chemistry Edition, 23:795-799 (1985).
Nagasaki, Y. et. al., Primary Amino-Terminal Heterobifunctional Poly(ethylene oxide). Facile Synthesis of Poly (ethylene oxide) with a Primary Amino Group at One End and a Hydroxyl Group at the Other End, Bioconjugate Chemistry, 6(6):702-704 (1995).
Reed, N. et al., A One-Step Synthesis of Monoprotected Polyethylene Glycol Ethers, Journal of Organic Chemistry, 65:5843-5845 (2000).
International Search Report, PCT/US07/10358, date of mailing Dec. 4, 2008.
Written Opinion, PCT/US07/10358, date of mailing Oct. 27, 2008.

* cited by examiner

*Primary Examiner* — Sudhakar Katakam

(57) ABSTRACT

The present invention provides bifunctional polymers, methods of preparing the same, and intermediates thereto. These compounds are useful in a variety of applications including the PEGylation of biologically active molecules. The invention also provides methods of using said compounds and compositions thereof.

5 Claims, No Drawings

SEQUENCE LISTING

<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: HIV Tat peptide sequence

<400> SEQUENCE: 1

Gly Arg Lys Lys Arg Gln Arg Arg Arg
1               5                   10

```
<210> SEQ ID NO 2
<211> LENGTH: 9
<212> TYPE: PRT
<213> ORGANISM: Artificial Sequence
<220> FEATURE:
<223> OTHER INFORMATION: Oligoarginine sequence

<400> SEQUENCE: 2

Arg Arg Arg Arg Arg Arg Arg Arg Arg
1               5

<210> SEQ ID NO 3
<211> LENGTH: 15
<212> TYPE: PRT
<213> ORGANISM: Artificial Sequence
<220> FEATURE:
<223> OTHER INFORMATION: Penetratin Sequence

<400> SEQUENCE: 3

Arg Gln Ile Lys Ile Trp Phe Gln Asn Arg Arg Met Lys Lys Lys
1               5                   10                  15

<210> SEQ ID NO 4
<211> LENGTH: 5
<212> TYPE: PRT
<213> ORGANISM: Artificial Sequence
<220> FEATURE:
<223> OTHER INFORMATION: Oligohistidine sequence

<400> SEQUENCE: 4

His His His His His
1               5
```

HETEROBIFUNCTIONAL POLY(ETHYLENE GLYCOL) CONTAINING ACID-LABILE AMINO PROTECTING GROUPS AND USES THEREOF

CROSS-REFERENCE TO RELATED APPLICATIONS

This application claims priority to U.S. provisional patent application Ser. No. 60/795,374, filed Apr. 27, 2006, the entirety of which is hereby incorporated herein by reference.

FIELD OF THE INVENTION

The present invention relates to the field of polymer chemistry and more particularly to functionalized polymers, uses thereof, and intermediates thereto.

BACKGROUND OF THE INVENTION

Poly(ethylene glycol), also known as PEG, is useful in a variety of technological areas and is generally known by the formula $HO-CH_2CH_2O-(CH_2CH_2O)_n-CH_2CH_2-OH$, wherein n typically ranges from about 3 to about 4000. In particular, there is great interest in utilizing PEG, and derivatives thereof, in the pharmaceutical and biomedical fields. This interest stems from the fact that PEG is nontoxic, biocompatible, non-immunogenic, soluble in water and other solvents, and is amenable to a variety of therapeutic applications including pharmaceutical formulations and drug delivery systems, among others.

One such area of interest relates to "PEGylation" or "conjugation" which refers to the modification of other molecules, especially biomolecules, using PEG and derivatives thereof. PEGylation is often utilized in order to impart the desirable characteristics of PEG to a particular molecule or biological scaffold. Such molecules or scaffolds targeted for PEGylation include proteins, dyes, peptides, hydrogels, cells, viruses, and drugs, to name but a few. In the case of drugs, the formation of PEG-drug conjugates is also of interest to improve aqueous solubility of hydrophobic drugs and improve biodistribution profiles. In addition, PEG has been utilized with a variety of natural and synthetic substrates including biological implants, medical devices, and the like. Accordingly, it would be advantageous to provide heterobifunctionalized PEG's having a variety of terminal functional groups.

DETAILED DESCRIPTION OF CERTAIN EMBODIMENTS OF THE INVENTION

1. General Description of the Invention

In certain embodiments, the present invention provides a compound of formula I:

$$\underset{R^y}{\overset{R^x}{>}}=N-G^1-O{\left(\!\!\!\begin{array}{c}\\ \end{array}\!\!\!O\!\!\!\right)}_n L^2 \! R^2 \qquad \text{I}$$

or a salt thereof, wherein:

n is 2-2500;

$R^x$ and $R^y$ are each independently optionally substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur, or:

$R^x$ and $R^y$ are taken together to form an optionally substituted 3-8 membered saturated or partially unsaturated ring having 0-3 heteroatoms independently selected from nitrogen, oxygen, or sulfur;

$G^1$ and $L^2$ are each independently a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

each X is independently halogen;

each R is independently hydrogen or an optionally substituted aliphatic group; and $R^2$ is hydrogen, halogen, $NO_2$, CN, $N_3$, —P(O)(OR)$_2$, —P(O)(X)$_2$, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety.

In other embodiments, the present invention provides a compound of formula II:

$$\underset{}{\overset{O}{\underset{O}{>}}}N-G^1-O{\left(\!\!\!\begin{array}{c}\\ \end{array}\!\!\!O\!\!\!\right)}_n L^2 \! R^2 \qquad \text{II}$$

or a salt thereof, wherein:

n is 2-2500;

$G^1$ and $L^2$ are each independently a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^2$ is hydrogen, halogen, $NO_2$, CN, $N_3$, —P(O)(OR)$_2$, —P(O)(X)$_2$, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

each X is independently halogen; and each R is independently hydrogen or an optionally substituted aliphatic group.

According to another embodiment, the present invention provides a compound of formula III:

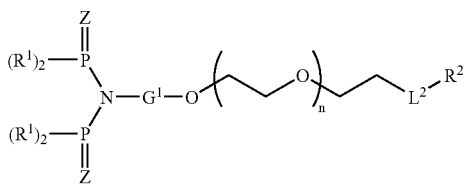

III or a salt thereof, wherein:

n is 2-2500;

each Z is independently oxygen or sulfur;

each $R^1$ is independently an optionally substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur;

$G^1$ and $L^2$ are each independently a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

each X is independently halogen;

each R is independently hydrogen or an optionally substituted aliphatic group; and $R^2$ is hydrogen, halogen, NO$_2$, CN, N$_3$, —P(O)(OR)$_2$, —P(O)(X)$_2$, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety.

In certain embodiments, the present invention provides a compound of formula IV:

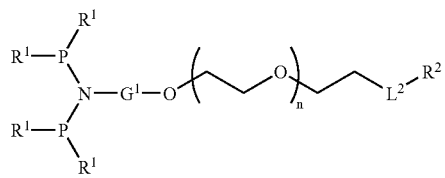

IV or a salt thereof, wherein:

n is 2-2500;

each $R^1$ is independently an optionally substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur;

$G^1$ and $L^2$ are each independently a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

each X is independently halogen;

each R is independently hydrogen or an optionally substituted aliphatic group; and $R^2$ is hydrogen, halogen, NO$_2$, CN, N$_3$, —P(O)(OR)$_2$, —P(O)(X)$_2$, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety.

2. Definitions

Compounds of this invention include those described generally above, and are further illustrated by the embodiments, sub-embodiments, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As used herein, the phrase "living polymer chain-end" refers to the terminus resulting from a polymerization reaction which maintains the ability to react further with additional monomer or with a polymerization terminator.

As used herein, the term "termination" refers to attaching a terminal group to a living polymer chain-end by reacting the living polymer chain-end with a polymerization terminator. Alternatively, the term "termination" may refer to the attachment of a terminal group to a hydroxyl end, or derivative thereof, of the polymer chain.

As used herein, the term "polymerization terminator" is used interchangeably with the term "polymerization terminating agent" and refers to compounds that react with a living polymer chain-end to afford a polymer with a terminal group. Alternatively, the term "polymerization terminator" may refer to a compound that may react with a hydroxyl end, or derivative thereof, of the polymer chain to afford a polymer with a terminal group.

As used herein, the term "polymerization initiator" refers to a compound, or anion thereof, which reacts with ethylene oxide in a manner which results in polymerization thereof. In certain embodiments, the polymerization initiator is the anion of a functional group which initiates the polymerization of ethylene oxide.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon. This includes any oxidized form of nitrogen, sulfur, phosphorus, or silicon; the quaternized form of any basic nitrogen, or; a substitutable nitrogen of a heterocyclic ring including =N— as in 3,4-dihydro-2H-pyrrolyl, —NH— as in pyrrolidinyl, or =N(R†)— as in N-substituted pyrrolidinyl.

The term "unsaturated", as used herein, means that a moiety has one or more units of unsaturation.

As used herein, the term "bivalent, saturated or unsaturated, straight or branched $C_{1-12}$ hydrocarbon chain", refers to bivalent alkylene, alkenylene, and alkynylene chains that are straight or branched as defined herein.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains three to seven ring members. The term "aryl" may be used interchangeably with the term "aryl ring".

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}$C(O)OR$^\circ$; —$(CH_2)_{0-4}$CH(OR$^\circ$)$_2$; —$(CH_2)_{0-4}$SR$^\circ$; —$(CH_2)_{0-4}$Ph, which may be substituted with R$^\circ$; —$(CH_2)_{0-4}$O(CH$_2$)$_{0-1}$Ph which may be substituted with R$^\circ$; —CH=CHPh, which may be substituted with R$^\circ$; —NO$_2$; —CN; —N$_3$; —$(CH_2)_{0-4}$N(R$^\circ$)$_2$; —$(CH_2)_{0-4}$N(R$^\circ$)C(O)R$^\circ$; —N(R$^\circ$)C(S)R$^\circ$; —$(CH_2)_{0-4}$N(R$^\circ$)C(O)NR$^\circ_{12}$; —N(R$^\circ$)C(S)NR$^\circ_2$; —$(CH_2)_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ_2$; —N(R$^\circ$)N(R$^\circ$)C(O)OR$^\circ$; —$(CH_2)_{0-4}$C(O)R$^\circ$; —C(S)R$^\circ$; —$(CH_2)_{0-4}$C(O)OR$^\circ$; —$(CH_2)_{0-4}$C(O)SR$^\circ$; —$(CH_2)_{0-4}$C(O)OSiR$^\circ_3$; —$(CH_2)_{0-4}$OC(O)R$^\circ$; —OC(O)(CH$_2$)$_{0-4}$SR—, SC(S)SR$^\circ$; —$(CH_2)_{0-4}$SC(O)R$^\circ$; —$(CH_2)_{0-4}$C(O)NR$^\circ_2$; —C(S)NR$^\circ_2$; —C(S)SR$^\circ$; —SC(S)SR$^\circ$, —$(CH_2)_{0-4}$OC(O)NR$^\circ_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —$(CH_2)_{0-4}$SSR$^\circ$; —$(CH_2)_{0-4}$S(O)$_2$R$^\circ$; —$(CH_2)_{0-4}$S(O)$_2$OR$^\circ$; —$(CH_2)_{0-4}$OS(O)$_2$R$^\circ$; —S(O)$_2$NR$^\circ_2$; —$(CH_2)_{0-4}$S(O)R$^\circ$; —N(R$^\circ$)S(O)$_2$NR$^\circ_2$; —N(R$^\circ$)S(O)$_2$R$^\circ$; —N(OR$^\circ$)R$^\circ$; —C(NH)NR$^\circ_2$; —P(O)$_2$R$^\circ$; —P(O)R$^\circ_2$; —OP(O)R$^\circ_2$; —OP(O)(OR$^\circ$)$_2$; SiR$^\circ_3$; —($C_{1-4}$ straight or branched alkylene)O—N(R$^\circ$)$_2$; or —($C_{1-4}$ straight or branched alkylene)C(O)O—N(R$^\circ$)$_2$, wherein each R$^\circ$ may be substituted as defined below and is independently hydrogen, $C_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —$(CH_2)_{0-2}$R$^\bullet$, -(haloR$^\bullet$), —$(CH_2)_{0-2}$OH, —$(CH_2)_{0-2}$OR$^\bullet$, —$(CH_2)_{0-2}$CH(OR$^\bullet$)$_2$; —O(haloR$^\bullet$), —CN, —N$_3$, —$(CH_2)_{0-2}$C(O)R$^\bullet$, —$(CH_2)_{0-2}$C(O)OH, —$(CH_2)_{0-2}$C(O)OR$^\bullet$, —$(CH_2)_{0-2}$SR$^\bullet$, —$(CH_2)_{0-2}$SH, —$(CH_2)_{0-2}$NH$_2$, —$(CH_2)_{0-2}$NHR$^\bullet$, —$(CH_2)_{0-2}$NR$^\bullet_2$, —NO$_2$, —SiR$^\bullet_3$, —OSiR$^\bullet_3$, —C(O)SR$^\bullet$, —($C_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. A suitable tetravalent substituent that is bound to vicinal substitutable methylene carbons of an "optionally substituted" group is the dicobalt hexacarbonyl cluster represented by

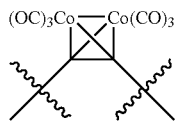

when depicted with the methylenes which bear it.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{554}$ are independently halogen, —R$^\dagger$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, propionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy) methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

A "crown ether moiety" is the radical of a crown ether. A crown ether is a monocyclic polyether comprised of repeating units of —CH$_2$CH$_2$O—. Examples of crown ethers include 12-crown-4, 15-crown-5, and 18-crown-6.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

As used herein, the term "detectable moiety" is used interchangeably with the term "label" and relates to any moiety capable of being detected (e.g., primary labels and secondary labels). A "detectable moiety" or "label" is the radical of a detectable compound.

"Primary" labels include radioisotope-containing moieties (e.g., moieties that contain $^{32}$P, $^{33}$P, $^{35}$S, or $^{14}$C), mass-tags, and fluorescent labels, and are signal-generating reporter groups which can be detected without further modifications.

Other primary labels include those useful for positron emission tomography including molecules containing radioisotopes (e.g. $^{18}$F) or ligands with bound radioactive metals (e.g. $^{62}$Cu). In other embodiments, primary labels are contrast agents for magnetic resonance imaging such as gadolinium, gadolinium chelates, or iron oxide (e.g $Fe_3O_4$ and $Fe_2O_3$) particles. Similarly, semiconducting nanoparticles (e.g. cadmium selenide, cadmium sulfide, cadmium telluride) are useful as fluorescent labels. Other metal nanoparticles (e.g colloidal gold) also serve as primary labels.

"Secondary" labels include moieties such as biotin, or protein antigens, that require the presence of a second compound to produce a detectable signal. For example, in the case of a biotin label, the second compound may include streptavidin-enzyme conjugates. In the case of an antigen label, the second compound may include an antibody-enzyme conjugate. Additionally, certain fluorescent groups can act as secondary labels by transferring energy to another compound or group in a process of nonradiative fluorescent resonance energy transfer (FRET), causing the second compound or group to then generate the signal that is detected.

Unless otherwise indicated, radioisotope-containing moieties are optionally substituted hydrocarbon groups that contain at least one radioisotope. Unless otherwise indicated, radioisotope-containing moieties contain from 1-40 carbon atoms and one radioisotope. In certain embodiments, radioisotope-containing moieties contain from 1-20 carbon atoms and one radioisotope.

The term "mass-tag" as used herein refers to any compound that is capable of being uniquely detected by virtue of its mass using mass spectrometry (MS) detection techniques. Examples of mass-tags include electrophore release tags such as N-[3-[4'-[(p-methoxytetrafluorobenzyl)oxy]phenyl]-3-methylglyceronyl]-isonipocotic acid, 4'-[2,3,5,6-tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "fluorescent label", "fluorescent group", "fluorescent compound", "fluorescent dye", and "fluorophore", as used herein, refer to compounds or moieties that absorb light energy at a defined excitation wavelength and emit light energy at a different wavelength. Examples of fluorescent compounds include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, anthracene, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), carbazole, Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "substrate", as used herein refers to any material or macromolecular complex to which a functionalized end-group of a PEG can be attached. Examples of commonly used substrates include, but are not limited to, glass surfaces, silica surfaces, plastic surfaces, metal surfaces, surfaces containing a metallic or chemical coating, membranes (e.g., nylon, polysulfone, silica), micro-beads (e.g., latex, polystyrene, or other polymer), porous polymer matrices (e.g., polyacrylamide gel, polysaccharide, polymethacrylate), and macromolecular complexes (e.g., protein, polysaccharide).

The term "targeting group", as used herein refers to any molecule, macromolecule, or biomacromolecule which selectively binds to receptors that are over-expressed on specific cell types. Such molecules can be attached to the functionalized end-group of a PEG for cell specific delivery of proteins, viruses, DNA plasmids, oligonucleotides (e.g. siRNA, miRNA, antisense therapeutics, aptamers, etc.), drugs, dyes, and primary or secondary labels which are bound to the opposite PEG end-group. Such targeting groups include, but or not limited to monoclonal and polyclonal antibodies (e.g. IgG, IgA, IgM, IgD, IgE antibodies), sugars (e.g. mannose, mannose-6-phosphate, galactose), proteins (e.g. Transferrin), oligopeptides (e.g. cyclic and acylic RGD-containing oligopedptides), oligonucleotides (e.g. aptamers), and vitamins (e.g. folate).

The term "permeation enhancer", as used herein refers to any molecule, macromolecule, or biomacromolecule which aids in or promotes the permeation of cellular membranes and/or the membranes of intracellular compartments (e.g. endosome, lysosome, etc.) Such molecules can be attached to the functionalized end-group of a PEG to aid in the intracellular and/or cytoplasmic delivery of proteins, viruses, DNA plasmids, oligonucleotides (e.g. siRNA, miRNA, antisense therapeutics, aptamers, etc.), drugs, dyes, and primary or secondary labels which are bound to the opposite PEG end-group. Such permeation enhancers include, but are not limited to, oligopeptides containing protein transduction domains such as the HIV Tat peptide sequence (GRKKRRQRRR), oligoarginine (RRRRRRRRR), or penetratin (RQIKIWFQNRRMKWKK). Oligopeptides which undergo conformational changes in varying pH environments such oligohistidine (HHHHH) also promote cell entry and endosomal escape.

3. Description of Exemplary Embodiments

As defined generally above, the n group of any of formulae I, II, III, and IV is 10-2500. In certain embodiments, the present invention provides compounds of any of formulae I, II, III, and IV, as described herein, wherein n is about 225. In other embodiments, n is about 10 to about 40. In other embodiments, n is about 40 to about 60. In other embodiments, n is about 60 to about 90. In still other embodiments, n is about 90 to about 150. In other embodiments, n is about 150 to about 200. In still other embodiments, n is about 200 to about 250. In other embodiments, n is about 300 to about 375. In other embodiments, n is about 400 to about 500. In still other embodiments, n is about 650 to about 750. In some embodiments, n is about 5 to about 10. In other embodiments, n is about 5 to about 15. In certain embodiments, n is selected from 50±10. In other embodiments, n is selected from 80±10, 115±10, 180±10, or 225±10.

According to another embodiment, the present invention provides a compound of any of formulae I, II, III, and IV, as described herein, wherein said compound has a polydispersity index ("PDI") of about 1.0 to about 1.2. According to another embodiment, the present invention provides a compound of any of formulae I, II, III, and IV, as described herein, wherein said compound has a polydispersity index ("PDI") of about 1.02 to about 1.05. According to yet another embodiment, the present invention provides a compound of any of formulae I, II, III, and IV, as described herein, wherein said compound has a polydispersity index ("PDI") of about 1.05 to about 1.10. In other embodiments, said compound has a PDI of about 1.01 to about 1.03. In other embodiments, said compound has a PDI of about 1.10 to about 1.15. In still other embodiments, said compound has a PDI of about 1.15 to about 1.20.

As defined generally above, $R^x$ and $R^y$ of formula I are each independently optionally substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur, or $R^x$ and $R^y$ are taken together to form an optionally substituted 3-8 membered saturated or partially unsaturated ring having 0-3 heteroatoms independently selected from nitrogen, oxygen, or sulfur.

In certain embodiments, $R^x$ and $R^y$ of formula I are each independently an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur. In other embodiments, $R^x$ and $R^y$ are each independently an optionally substituted 3-8 membered saturated, partially unsaturated, or aryl ring having 0-4 heteroatoms independently selected from nitrogen, oxygen, or sulfur. In still other embodiments, $R^x$ and $R^y$ of formula I are each independently phenyl optionally substituted with one or more groups independently selected from $R^o$ as defined herein, CN, $N_3$, $NO_2$, —$CH_3$, —$CH_2N_3$, t-butyl, 5-norbornene-2-yl, octane-5-yl, —CH=$CH_2$, —C≡CH, —$CH_2$C≡CH, —$CH_2CH_2$C≡CH, —$CH_2CH_2CH_2$C≡CH, Cl, Br, I, F, —$NH_2$, —OH, —SH, —$CO_2$H, —C(O)H, —$CH_2NH_2$, —$CH_2$OH, —$CH_2$SH, —$CH_2CO_2$H, —$CH_2$C(O)H, —C(O)($C_{1-6}$ aliphatic), —NHC(O)($C_{1-6}$ aliphatic), —NHC(O)NH—, —NHC(O)NH($C_{1-6}$ aliphatic), —NHC(S)NH—, —NHC(S)N($C_{1-6}$ aliphatic)$_2$, —NHC(O)O($C_{1-6}$ aliphatic), —NHNH$_2$, —NHNHC(O)($C_{1-6}$ aliphatic), —NHNHC(O)NH$_2$, —NHNHC(O)NH($C_{1-6}$ aliphatic), —NHNHC(O)O($C_{1-6}$ aliphatic), —C(O)NH$_2$, —C(O)NH($C_{1-6}$ aliphatic)$_2$, —C(O)NHNH$_2$, —C(S)N($C_{1-6}$ aliphatic)$_2$, —OC(O)NH($C_{1-6}$ aliphatic), —C(O)C(O)($C_{1-6}$ aliphatic), —C(O)CH$_2$C(O)($C_{1-6}$ aliphatic), —S(O)$_2$($C_{1-6}$ aliphatic), —S(O)$_2$O($C_{1-6}$ aliphatic), —OS(O)$_2$($C_{1-6}$ aliphatic), —S(O)$_2$NH($C_{1-6}$ aliphatic), —S(O) ($C_{1-6}$ aliphatic), —NHS(O)$_2$NH($C_{1-6}$ aliphatic), —NHS(O)$_2$($C_{1-6}$ aliphatic), —P(O)$_2$($C_{1-6}$ aliphatic), —P(O)($C_{1-6}$ aliphatic)$_2$, —OP(O)($C_{1-6}$ aliphatic)$_2$, or —OP(O)(O$C_{1-6}$ aliphatic)$_2$.

In other embodiments, $R^x$ and $R^y$ of formula I are each independently optionally substituted aliphatic. In other embodiments, $R^x$ and $R^y$ of formula I are each independently an unsubstituted aliphatic. In some embodiments, each $R^x$ and $R^y$ group is an optionally substituted alkyl group. In other embodiments, each $R^x$ and $R^y$ group is an optionally substituted alkynyl or alkenyl group. Such groups include t-butyl, 5-norbornene-2-yl, octane-5-yl, —C≡CH, —$CH_2$C=CH, —$CH_2CH_2$C≡CH, and —$CH_2CH_2CH_2$C≡CH. When each $R^x$ and $R^y$ group is a substituted aliphatic group, suitable substituents on each $R^x$ and $R^y$ group include any of CN, $N_3$, $NO_2$, —$CO_2$H, —SH, —$NH_2$, —C(O)H, —NHC(O)$R^o$, —NHC(S)$R^o$, —NHC(O)N($R^o$)$_2$, —NHC(S)N($R^o$)$_2$, —NHC(O)O$R^o$, —NHNHC(O)$R^o$, —NHNHC(O)N($R^o$)$_2$, —NHNHC(O)O$R^o$, —C(O)$R^o$, —C(S)$R^o$, —C(O)O$R^o$, —C(O)S$R^o$, —C(O)OSi($R^o$)$_3$, —OC(O)$R^o$, SC(S)S$R^o$, —SC(O)$R^o$, —C(O)N($R^o$)$_2$, —C(S)N($R^o$)$_2$, —C(S)S$R^o$; —SC(S)S$R^o$, —OC(O)N($R^o$)$_2$; —C(O)NHN($R^o$)$_2$, —C(O)N(O$R^o$)$R^o$, —C(O)C(O)$R^o$, —C(O)CH$_2$C(O)$R^o$, —C(NO$R^o$)$R^o$, —SS$R^o$, —S(O)$_2$$R^o$, —S(O)$_2$O$R^o$, —OS(O)$_2$$R^o$, —S(O)$_2$ N($R^o$)$_2$, —S(O)$R^o$, —N($R^o$)S(O)$_2$N($R^o$)$_2$, —N($R^o$)S(O)$_2$$R^o$, —N(O$R^o$)$R^o$, —C(NH)N($R^o$)$_2$, —P(O)$_2$$R^o$, —P(O)($R^o$)$_2$, —OP(O)($R^o$)$_2$, or —OP(O)(O$R^o$)$_2$, wherein each $R^o$ is as defined herein.

In other embodiments, each $R^x$ and $R^y$ group of formula I is an aliphatic group optionally substituted with any of Cl, Br, I, F, —$NH_2$, —OH, —SH, —$CO_2$H, —C(O)H, —C(O)($C_{1-6}$ aliphatic), —NHC(O)($C_{1-6}$ aliphatic), —NHC(O)NH—, —NHC(O)NH($C_{1-6}$ aliphatic), —NHC(S)NH$_2$, —NHC(S)N($C_{1-6}$ aliphatic)$_2$, —NHC(O)O($C_{1-6}$ aliphatic), —NHNH$_2$, —NHNHC(O)($C_{1-6}$ aliphatic), —NHNHC(O)NH$_2$, —NHNHC(O)NH($C_{1-6}$ aliphatic), —NHNHC(O)O($C_{1-6}$ aliphatic), —C(O)NH$_2$, —C(O)NH($C_{1-6}$ aliphatic)$_2$, —C(O)NHNH$_2$, —C(S)N($C_{1-6}$ aliphatic)$_2$, —OC(O)NH($C_{1-6}$ aliphatic), —C(O)C(O)($C_{1-6}$ aliphatic), —C(O)CH$_2$C(O)($C_{1-6}$ aliphatic), —S(O)$_2$($C_{1-6}$ aliphatic), —S(O)$_2$O($C_{1-6}$ aliphatic), —OS(O)$_2$($C_{1-6}$ aliphatic), —S(O)$_2$NH($C_{1-6}$ aliphatic), —S(O)($C_{1-6}$ aliphatic), —NHS(O)$_2$NH($C_{1-6}$ aliphatic), —NHS(O)$_2$($C_{1-6}$ aliphatic), —P(O)$_2$($C_{1-6}$ aliphatic), —P(O)($C_{1-6}$ aliphatic)$_2$, —OP(O)($C_{1-6}$ aliphatic)$_2$, or —OP(O)(O$C_{1-6}$ aliphatic)$_2$.

In certain embodiments, one of $R^x$ and $R^y$ of formula I is an optionally substituted aliphatic group, as defined and described herein, and the other of $R^x$ and $R^y$ is an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur, as defined and described herein.

In certain embodiments, $R^x$ and $R^y$ of formula I are taken together to form a 3-8 membered saturated or partially unsaturated ring having 0-3 heteroatoms independently selected from nitrogen, oxygen, or sulfur. In other embodiments, $R^x$ and $R^y$ are taken together to form an optionally substituted 3-6 membered saturated or partially unsaturated ring having 0-1 heteroatoms independently selected from nitrogen, oxygen, or sulfur. In still other embodiments, $R^x$ and $R^y$ are taken together to form an optionally substituted 5-6 membered saturated or partially unsaturated ring having 0-1 heteroatoms independently selected from nitrogen, oxygen, or sulfur. Such groups include those depicted in Table 1, below.

As defined generally above, the $G^1$ group of any of formulae I, II, III, and IV is a valence bond or a bivalent, saturated or unsaturated, straight or branched $C_{1-12}$ hydrocarbon chain, wherein 0-6 methylene units of $G^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, $G^1$ group of any of formulae I, II, III, and IV is a valence bond. In other embodiments, $G^1$ is a bivalent, saturated $C_{1-12}$ hydrocarbon chain, wherein 0-6 methylene units of $G^1$ are independently replaced by -Cy-, —O—, —NH—, —S—, —OC(O)—, —C(O)O—, —C(O)—, —C(O)NH—, or —NHC(O)—, wherein each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In still other embodiments, $G^1$ is a bivalent, saturated $C_{1-6}$ alkylene chain, wherein 0-3 methylene units of $G^1$ are independently replaced by -Cy-, —O—, —NH—, —S—, —OC(O)—, —C(O)O—, —C(O)—, —C(O)NH—, or —NHC(O)—.

In certain embodiments, the $G^1$ group of any of formulae I, II, III, and IV is -Cy- (i.e. a $C_1$ alkylene chain wherein the methylene unit is replaced by -Cy-), wherein -Cy- is an optionally substituted 3-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, the $G^1$ group of any of formulae I, II, III, and IV is —O—, —S—, or —NH—. In other embodiments, the $G^1$ group of any of formulae I, II, III, and IV is -Cy-, -Cy-CH$_2$—, —CH$_2$-Cy-, -Cy-CH$_2$CH$_2$—, —NH—, or —O-Cy-CH$_2$NH—. In still other embodiments, the $G^1$ group of any of formulae I, II, III, and IV is any of —OCH$_2$—, —OCH$_2$CH$_2$—, —OCH$_2$CH$_2$—, or —OCH$_2$CH$_2$NH—. In some embodiments, the $G^1$ group of any of formulae I, II, III, and IV is any of —CH$_2$—, —CH$_2$CH$_2$—, or —CH$_2$CH$_2$CH$_2$—.

As defined generally above, the $R^2$ group of any of formulae I, II, III, and IV is hydrogen, halogen, NO$_2$, CN, N$_3$, —N═C═O, —C(R)═NN(R)$_2$, —P(O)(OR)$_2$, —P(O)(X)$_2$, a 9-30-membered crown ether, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety; wherein each R is independently hydrogen or an optionally substituted aliphatic group.

In certain embodiments, the $R^2$ group of any of formulae I, II, III, and IV is optionally substituted aliphatic. In other embodiments, $R^2$ is an unsubstituted aliphatic. In some embodiments, said $R^2$ moiety is an optionally substituted alkyl group. In other embodiments, said $R^2$ moiety is an optionally substituted alkynyl or alkenyl group. Such groups include t-butyl, 5-norbornene-2-yl, octane-5-yl, —C≡CH, —CH$_2$C≡CH, —CH$_2$CH$_2$C≡CH, and —CH$_2$CH$_2$CH$_2$C≡CH. When said $R^2$ moiety is a substituted aliphatic group, suitable substituents on $R^2$ include any of CN, N$_3$, NO$_2$, —CO$_2$H, —SH, —NH$_2$, —C(O)H, —NHC(O)R$^o$, —NHC(S)R$^o$, —NHC(O)N(R$^o$)$_2$, —NHC(S)N(R$^o$)$_2$, —NHC(O)OR$^o$, —NHNHC(O)R$^o$, —NHNHC(O)N(R$^o$)$_2$, —NHNHC(O)OR$^o$, —C(O)R$^o$, —C(S)R$^o$, —C(O)OR$^o$, —C(O)SR$^o$, —C(O)OSi(R$^o$)$_3$, —OC(O)R$^o$, SC(S)SR$^o$, —SC(O)R$^o$, —C(O)NR$^o$$_2$, —C(S)NR$^o$$_2$, —C(S)SR$^o$; —SC(S)SR$^o$, —OC(O)N(R$^o$)$_2$; —C(O)NHN(R$^o$)$_2$, —C(O)N(OR$^o$)R$^o$, —C(O)C(O)R$^o$, —C(O)CH$_2$C(O)R$^o$—, —C(NOR$^o$)R$^o$, —SSR$^o$, —S(O)$_2$R$^o$, —S(O)$_2$OR$^o$, —OS(O)$_2$R$^o$, —S(O)$_2$N(R$^o$)$_2$, —S(O)R$^o$, —N(R$^o$)S(O)$_2$N(R$^o$)$_2$, —N(R$^o$)S(O)$_2$R$^o$, —N(OR$^o$)R$^o$, —C(NH)N(R$^o$)$_2$, —P(O)$_2$R$^o$, —P(O)(R$^o$)$_2$, —OP(O)(R$^o$)$_2$, or —OP(O)(OR$^o$)$_2$, wherein each R$^o$ is as defined herein.

In other embodiments, the $R^2$ group of any of formulae I, II, III, and IV is an aliphatic group optionally substituted with any of Cl, Br, I, F, —NH$_2$, —OH, —SH, —CO$_2$H, —C(O)H, —C(O)(C$_{1-6}$ aliphatic), —NHC(O)(C$_{1-6}$ aliphatic), —NHC(O)NH—, —NHC(O)NH(C$_{1-6}$ aliphatic), —NHC(S)NH$_2$, —NHC(S)N(C$_{1-6}$ aliphatic)$_2$, —NHC(O)N(C$_{1-6}$ aliphatic)$_2$, —NHC(S)O(C$_{1-6}$ aliphatic), —NHNH$_2$, —NHNHC(O)(C$_{1-6}$ aliphatic), —NHNHC(O)NH$_2$, —NHNHC(O)NH(C$_{1-6}$ aliphatic), —NHNHC(O)O(C$_{1-6}$ aliphatic), —C(O)NH$_2$, —C(O)NH(C$_{1-6}$ aliphatic)$_2$, —C(O)NHNH$_2$, —C(S)N(C$_{1-6}$ aliphatic)$_2$, —OC(O)NH(C$_{1-6}$ aliphatic), —C(O)C(O)(C$_{1-6}$ aliphatic), —C(O)CH$_2$C(O)(C$_{1-6}$ aliphatic), —S(O)$_2$(C$_{1-6}$ aliphatic), —S(O)$_2$O(C$_{1-6}$ aliphatic), —OS(O)$_2$(C$_{1-6}$ aliphatic), —S(O)$_2$NH(C$_{1-6}$ aliphatic), —S(O)(C$_{1-6}$ aliphatic), NHS(O)$_2$NH(C$_{1-6}$ aliphatic), —NHS(O)$_2$(C$_{1-6}$ aliphatic), —P(O)$_2$(C$_{1-6}$ aliphatic), —P(O)(C$_{1-6}$ aliphatic)$_2$, —OP(O)(C$_{1-6}$ aliphatic)$_2$, or —OP(O)(OC$_{16}$ aliphatic)$_2$.

In certain embodiments, the $R^2$ group of any of formulae I, II, III, and IV is a group suitable for Click chemistry. Click reactions tend to involve high-energy ("spring-loaded") reagents with well-defined reaction coordinates, that give rise to selective bond-forming events of wide scope. Examples include nucleophilic trapping of strained-ring electrophiles (epoxide, aziridines, aziridinium ions, episulfonium ions), certain carbonyl reactivity (e.g., the reaction between aldehydes and hydrazines or hydroxylamines), and several cycloaddition reactions. The azide-alkyne 1,3-dipolar cycloaddition is one such reaction. Click chemistry is known in the art and one of ordinary skill in the art would recognize that certain $R^2$ moieties of the present invention are suitable for Click chemistry.

According to one embodiment, the $R^2$ group of any of formulae I, II, III, and IV is an azide-containing group. According to another embodiment, the $R^2$ group of any of formulae I, II, III, and IV is an alkyne-containing group. In certain embodiments, the $R^2$ group of any of formulae I, II, III, and IV has a terminal alkyne moiety.

According to another embodiment, the $R^2$ group of any of formulae I, II, III, and IV is an aldehyde-containing group.

In certain embodiments, the $R^2$ group of any of formulae I, II, III, and IV has a terminal hydrazine moiety.

In other embodiments, the $R^2$ group of any of formulae I, II, III, and IV has a terminal oxyamine moiety.

In still other embodiments, the $R^2$ group of any of formulae I, II, III, and IV is a epoxide-containing group.

In certain other embodiments, the $R^2$ group of any of formulae I, II, III, and IV has a terminal maleimide moiety.

In some embodiments, the $R^2$ group of any of formulae I, II, III, and IV is —$NH_2$.

In other embodiments, the $R^2$ group of any of formulae I, II, III, and IV is an optionally substituted 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur. In certain embodiments, $R^2$ is an optionally substituted 3-7 membered saturated or partially unsaturated ring having 0-4 heteroatoms independently selected from nitrogen, oxygen, or sulfur. In other embodiments, $R^2$ is an optionally substituted phenyl ring or a 5-6 membered heteroaryl ring having 1-4 heteroatoms independently selected from nitrogen, oxygen, or sulfur.

In certain embodiments, the $R^2$ group of any of formulae I, II, III, and IV is an optionally substituted aryl group. Examples include optionally substituted phenyl, optionally substituted pyridyl, optionally substituted naphthyl, optionally substituted pyrenyl, optionally substituted triazole, optionally substituted imidazole, optionally substituted phthalimide, optionally substituted tetrazole, optionally substituted furan, and optionally substituted pyran. When said $R^2$ moiety is a substituted aryl group, suitable substituents on $R^2$ include $R°$, CN, $N_3$, $NO_2$, —$CH_3$, —$CH_2N_3$, t-butyl, 5-norbornene-2-yl, octane-5-yl, —CH═$CH_2$, —C≡CH, —$CH_2$C≡CH, —$CH_2CH_2$C≡CH, —$CH_2CH_2CH_2$C≡CH, Cl, Br, I, F, —$NH_2$, —OH, —SH, —$CO_2H$, —C(O)H, —$CH_2NH_2$, —$CH_2OH$, —$CH_2SH$, —$CH_2CO_2H$, —$CH_2C$(O)H, —C(O)($C_{1-6}$ aliphatic), —NHC(O)($C_{1-6}$ aliphatic), —NHC(O)NH—, —NHC(O)NH($C_{1-6}$ aliphatic), —NHC(S)NH—, —NHC(S)N($C_{1-6}$ aliphatic)$_2$, —NHC(O)O($C_{1-6}$ aliphatic), —$NHNH_2$, —NHNHC(O)($C_{1-6}$ aliphatic), —$NHNHC(O)NH_2$, —NHNHC(O)NH($C_{1-6}$ aliphatic), —NHNHC(O)O($C_{1-6}$ aliphatic), —C(O)$NH_2$, —C(O)NH ($C_{1-6}$ aliphatic)$_2$, —C(O)$NHNH_2$, —C(S)N($C_{1-6}$ aliphatic)$_2$, —OC(O)NH($C_{1-6}$ aliphatic), —C(O)C(O)($C_{1-6}$ aliphatic), —C(O)$CH_2$C(O)($C_{1-6}$ aliphatic), —S(O)$_2$($C_{1-6}$ aliphatic), —S(O)$_2$O($C_{1-6}$ aliphatic), —OS(O)$_2$($C_{1-6}$ aliphatic), —S(O)$_2$NH($C_{1-6}$ aliphatic), —S(O) ($C_{1-6}$ aliphatic), —NHS(O)$_2$NH($C_{1-6}$ aliphatic), —NHS(O)$_2$($C_{1-6}$ aliphatic), —P(O)$_2$($C_{1-6}$ aliphatic), —P(O)($C_{1-6}$ aliphatic)$_2$, —OP(O)($C_{1-6}$ aliphatic)$_2$, or —OP(O)(O$C_{1-6}$ aliphatic)$_2$.

Suitable substitutents on the $R^2$ group of any of formulae I, II, III, and IV further include bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl.

In other embodiments, the $R^2$ group of any of formulae I, II, III, and IV is hydrogen.

In certain embodiments, the $R^2$ group of any of formulae I, II, III, and IV is $N_3$.

In other embodiments, the $R^2$ group of any of formulae I, II, III, and IV is an epoxide ring.

In certain embodiments, the $R^2$ group of any of formulae I, II, III, and IV is a crown ether. Examples of such crown ethers include 12-crown-4, 15-crown-5, and 18-crown-6.

In still other embodiments, the $R^2$ group of any of formulae I, II, III, and IV is a detectable moiety. Detectable moieties are known in the art and include those described herein. According to one aspect of the invention, the $R^2$ group of any of formulae I, II, III, and IV is a fluorescent moiety. Such fluorescent moieties are well known in the art and include coumarins, quinolones, benzoisoquinolones, hostasol, and Rhodamine dyes, to name but a few. Exemplary fluorescent moieties of $R^2$ include anthracen-9-yl, pyren-4-yl, 9-H-carbazol-9-yl, the carboxylate of rhodamine B, and the carboxylate of coumarin 343. In certain embodiments, $R^2$ is a detectable moiety selected from:

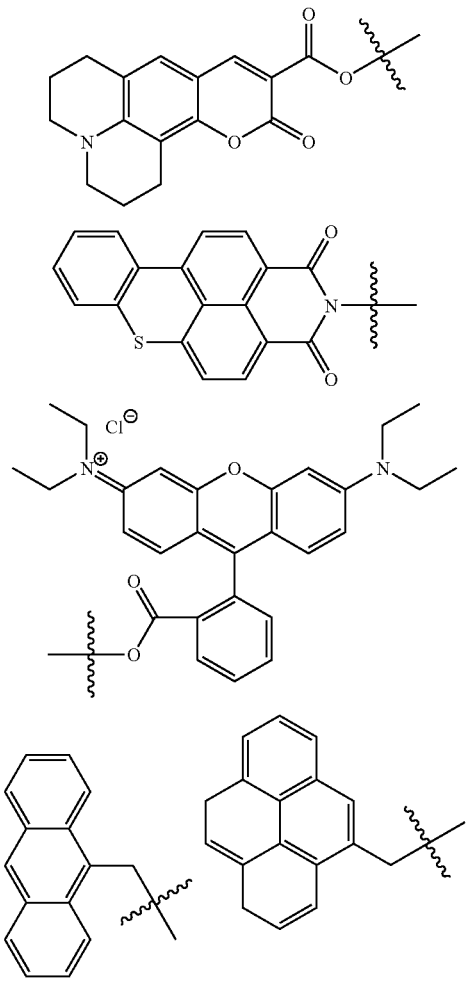

-continued

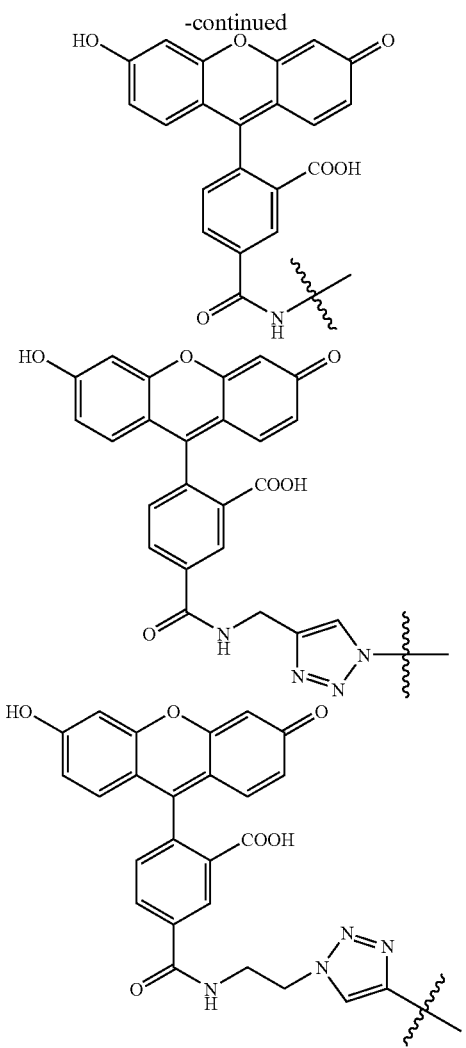

wherein each wavy line indicates the point of attachment to the rest of the molecule.

In certain embodiments, the $R^2$ group of any of formulae I, II, III, and IV is —P(O)(OR)$_2$, or —P(O)(X)$_2$. According to one aspect, the present invention provides a compound of any of formulae I, II, III, and IV, wherein $R^2$ is —P(O)(OH)$_2$. According to another aspect, the present invention provides a compound of any of formulae I, II, III, and IV wherein $R^2$ is —P(O)(Cl)$_2$.

As defined generally above, the $L^2$ group of any of formulae I, II, III, and IV is a valence bond or a bivalent, saturated or unsaturated, straight or branched $C_{1-12}$ hydrocarbon chain, wherein 0-6 methylene units of $L^2$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, —NRC(O)O—, —NH—O—, or —O-Cy-CH$_2$NH—O—, wherein each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, the $L^2$ group of any of formulae I, II, III, and IV is a $C_{1-6}$ alkylene chain wherein one methylene unit of $L^2$ is replaced by -Cy- or —OCy-. In other embodiments, $L^2$ is -Cy- (i.e. a $C_1$ alkylene chain wherein the methylene unit is replaced by -Cy-), wherein -Cy- is an optionally substituted 3-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, the $L^2$ group of any of formulae I, II, III, and IV is —O-Cy- (i.e. a $C_2$ alkylene chain wherein one methylene unit is replaced by -Cy- and the other by —O—), wherein -Cy- is an optionally substituted 3-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, the $L^2$ group of any of formulae I, II, III, and IV is —O—, —S—, —NH—, or —C(O)O—. In other embodiments, the $L^2$ group of any of formulae I, II, III, and IV is -Cy-, —C(O)—, —C(O)NH—, —NH—O—, —O-Cy-CH$_2$NH—O—, or —NHC(O)—. In still other embodiments, the $L^2$ group of any of formulae I, II, III, and IV is any of —OCH$_2$—, —OCH$_2$C(O)—, —OCH$_2$CH$_2$C(O)—, —OCH$_2$CH$_2$O—, —OCH$_2$CH$_2$S—, —OCH$_2$CH$_2$C(O)O—, —OCH$_2$CH$_2$NH—, —OCH$_2$CH$_2$NHC(O)—, —OCH$_2$CH$_2$C(O)NH—, and —NHC(O)CH$_2$CH$_2$C(O)O—. According to another aspect, the $L^2$ group of any of formulae I, II, III, and IV is any of —OCH$_2$CH$_2$NHC(O)CH$_2$CH$_2$C(O)O—, —OCH$_2$CH$_2$NHC(O)CH$_2$OCH$_2$C(O)O—, —OCH$_2$CH$_2$NHC(O)CH$_2$OCH$_2$C(O)NH—, —CH$_2$C(O)NH—, —CH$_2$C(O)NHNH—, or —OCH$_2$CH$_2$NHNH—. In other embodiments, the $L^2$ group of any of formulae I, II, III, and IV is —OC(O)CH$_2$CH$_2$CH$_2$CH$_2$—, —OCH$_2$CH$_2$—, —NHC(O)CH$_2$CH$_2$—, —NHC(O)CH$_2$CH$_2$CH$_2$—, —OC(O)CH$_2$CH$_2$CH$_2$—, —O-Cy-, —O-Cy-CH$_2$—, —O-Cy-NH—, —O-Cy-S—, —O-Cy-C(O)—, —O-Cy-C(O)O—, —O-Cy-C(O)O-Cy-, —O-Cy-OCH$_2$CH(CH$_3$)C(O)O—, —O-Cy-C(O)O—, —O-Cy-OCH(CH$_3$)CH$_2$C(O)O—, —OCH$_2$C(O)O—, —OCH$_2$C(O)NH—, —OCH$_2$O—, —OCH$_2$S—, or —OCH$_2$NH—. In certain embodiments, $L^2$ is —O—.

According to another aspect of the present invention, a functional group formed by the -$L^2$-$R^2$ moiety of any of formulae I, II, III, and IV is optionally protected. Thus, in certain embodiments, the -$L^2$-$R^2$ moiety of any of formulae I, II, III, and IV optionally comprises a mono-protected amine, a di-protected amine, a protected aldehyde, a protected hydroxyl, a protected carboxylic acid, or a protected thiol group. Such groups include those described above with respect to the -L²-R² moiety of any of formulae I, II, III, and IV.

In certain embodiments, each R¹ group of formulae III and IV is independently an optionally substituted aliphatic or an optionally substituted 3-8 membered saturated, partially unsaturated, or aryl ring. In some embodiments, each R¹ group of formulae III and IV is independently $C_{1-4}$ straight or branched alkyl. In other embodiments, each R¹ is independently $C_{4-8}$ cycloalkyl. In still other embodiments, each R¹ is independently optionally substituted phenyl.

substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur;

According to another embodiment, the present invention provides a compound of any of formulae I-a, I-b, I-c, I-d, I-e, I-f, I-g, I-h, I-i, I-j, I-k, I-l, and I-m:

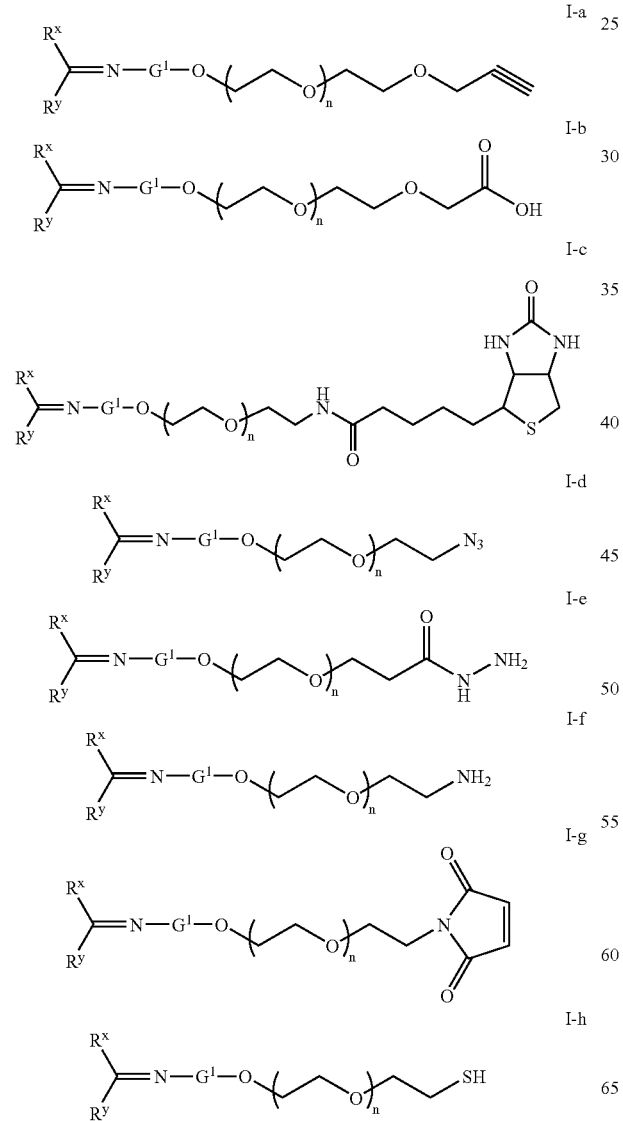

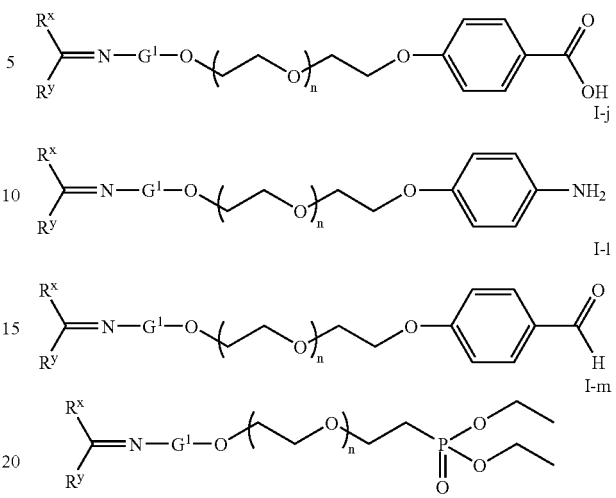

or a salt thereof, wherein each of n, G¹, $R^x$, and $R^y$ is as defined above and described in classes and subclasses herein, independently, singly and in combination.

Representative —N=$R^x$($R^y$) groups of formula I are set forth in Table 1, below.

TABLE 1

Representative —N = $R^x$($R^y$) Groups of Formula I

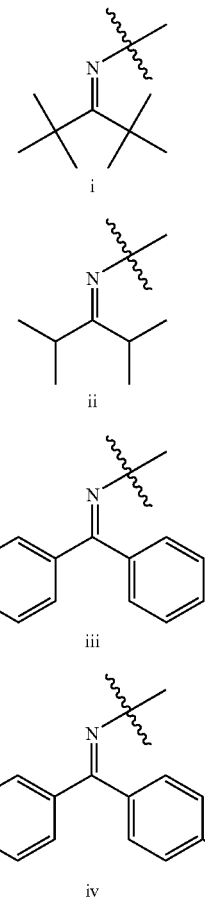

TABLE 1-continued
Representative —N=R$^x$(R$^y$) Groups of Formula I
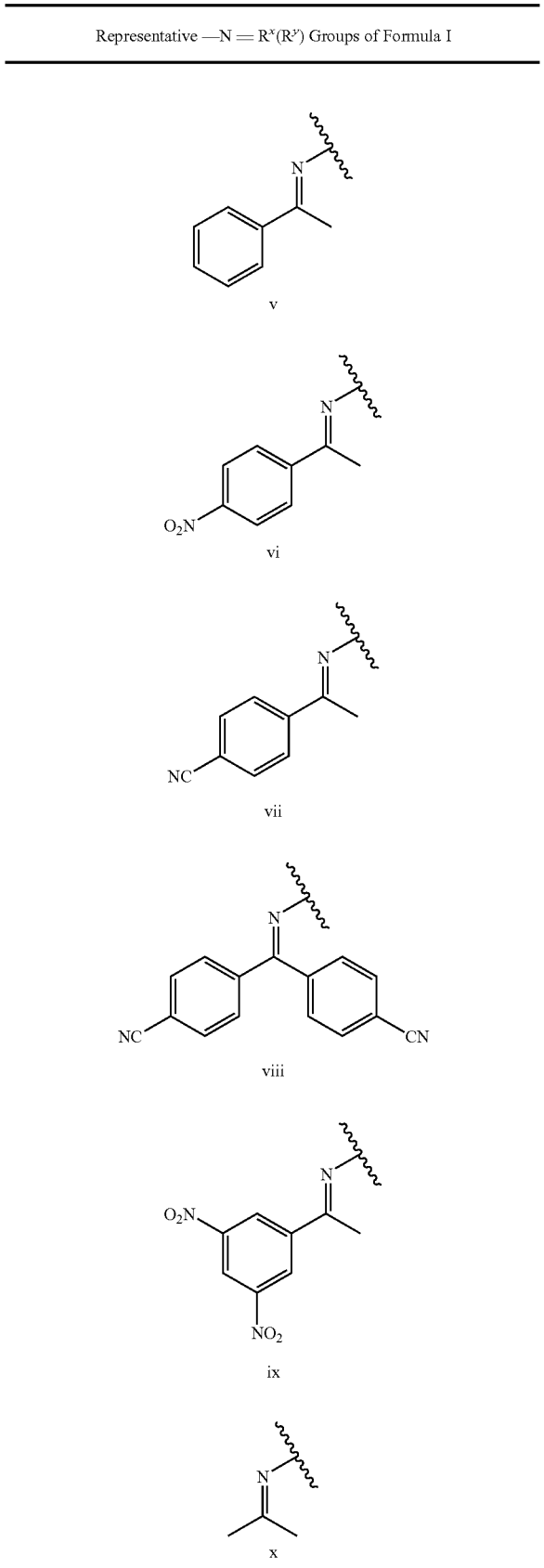
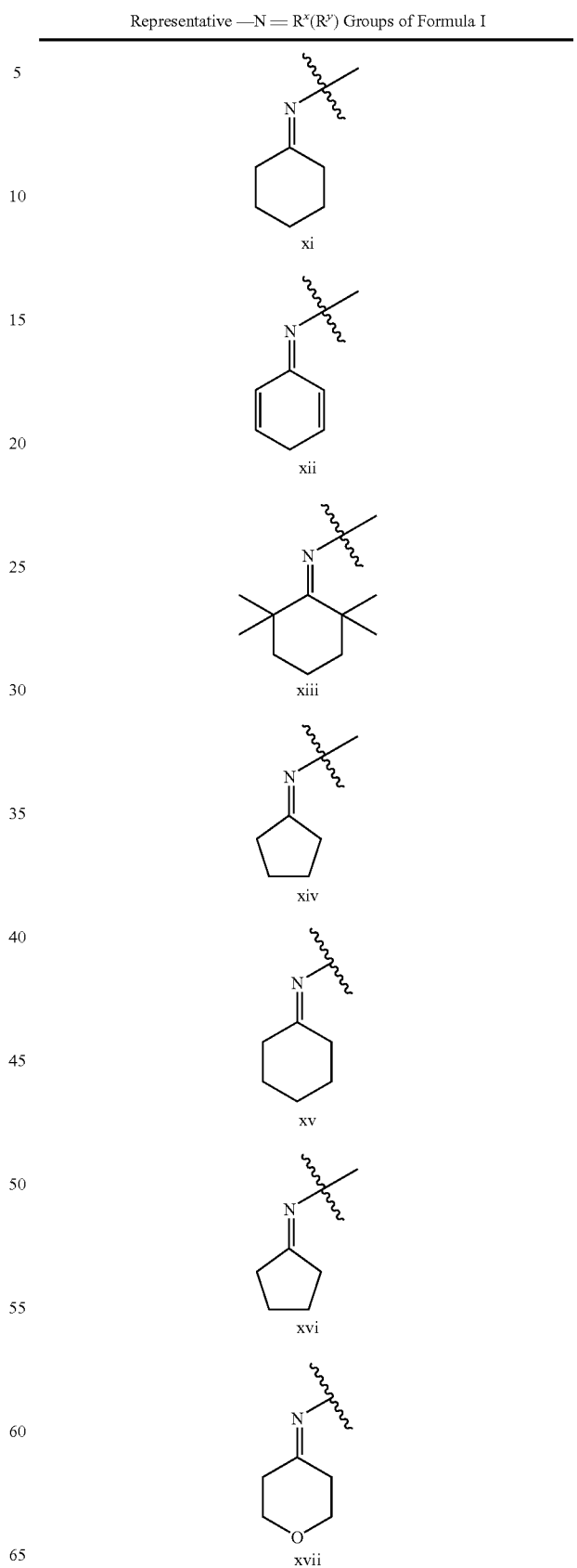

TABLE 1-continued

Representative —N═R$^x$(R$^y$) Groups of Formula I

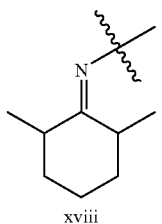
xviii

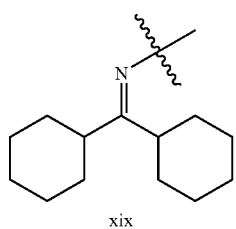
xix

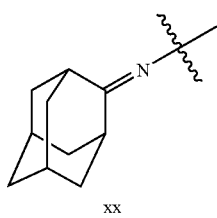
xx

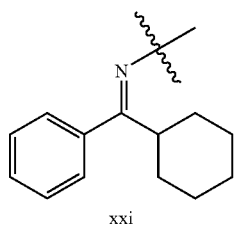
xxi

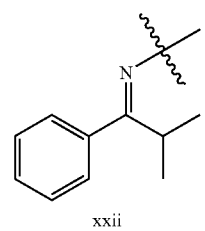
xxii

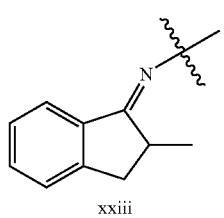
xxiii wherein each wavy line designates the point of attachment to the rest of the molecule.

In certain embodiments, the present invention provides a compound of any of formulae II-a, II-b, II-c, II-d, II-e, II-f, II-g, and II-h:

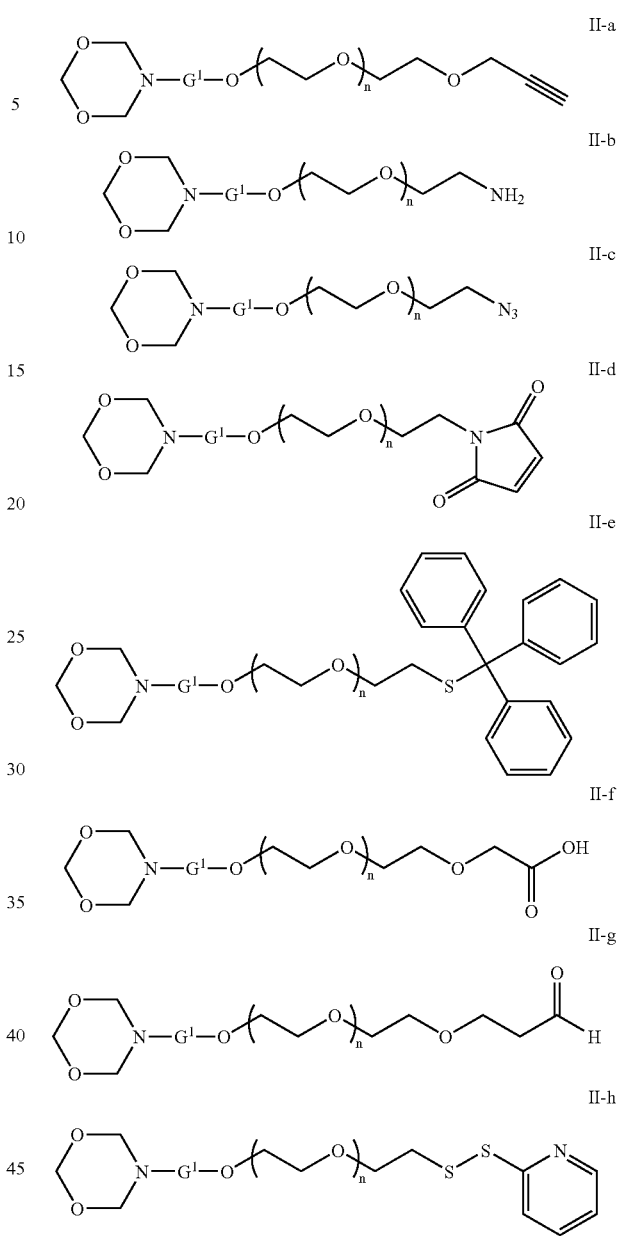

or a salt thereof, wherein each of n and G$^1$ is as defined above and described in classes and subclasses herein, independently, singly and in combination.

In some embodiments, the present invention provides a compound of any of formulae III-a, III-b, III-c, III-d, III-e, III-f, III-g, and III-h:

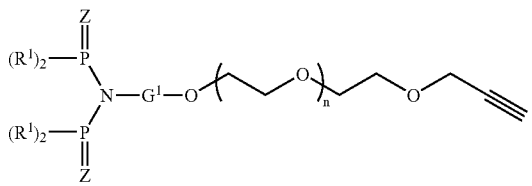

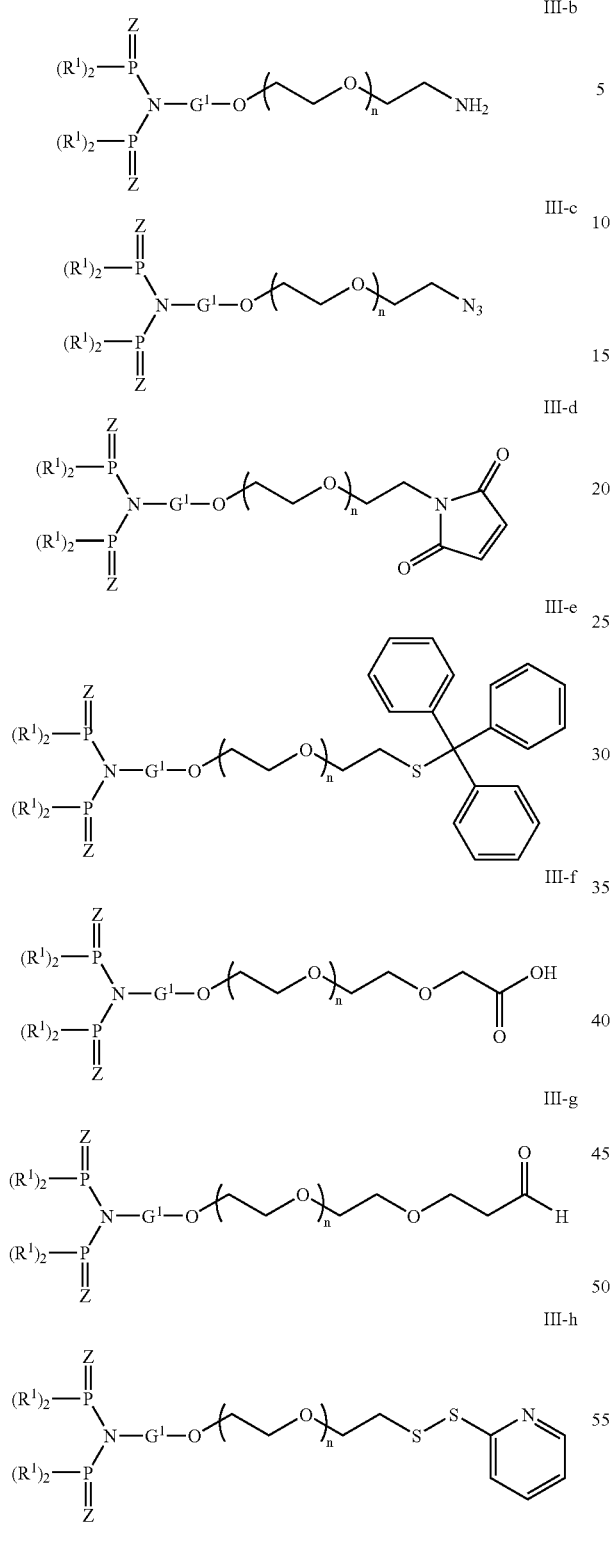
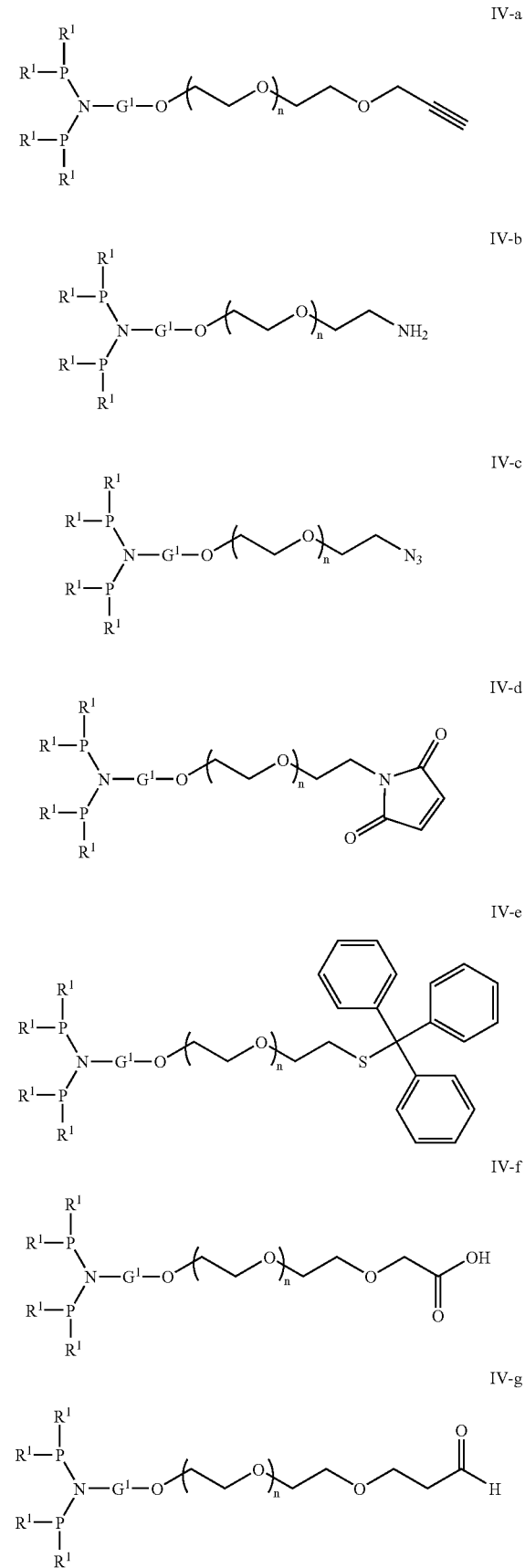
or a salt thereof, wherein each of n, G¹, Z, and R¹ is as defined above and described in classes and subclasses herein, independently, singly and in combination.
In certain embodiments, the present invention provides a compound of any of formulae IV-a, IV-b, IV-c, IV-d, IV-e, IV-f, IV-g, and IV-h:

-continued

IV-h $$R^1-\underset{\underset{R^1}{|}}{P}-\underset{\underset{\underset{R^1}{|}}{P}-R^1}{N}-G^1-O\left(\phantom{\rule{0ex}{0ex}}\right)\!\!\left(O\right)_n\!\!\left(\phantom{\rule{0ex}{0ex}}\right)\!\!S\!\!-\!\!S\!\!-\!\!\underset{}{\underset{}{\underset{}{\underset{}{\text{pyridyl}}}}}$$

or a salt thereof, wherein each of n, $G^1$, and $R^1$ is as defined above and described in classes and subclasses herein, independently, singly and in combination.

In certain embodiments, the present invention provides a method for preparing a compound of formula V:

$$\overset{\ominus}{A}\;\overset{\oplus}{H_3N}-G^1-O\!\!\left(\phantom{\rule{0ex}{0ex}}\right)\!\!\left(O\right)_n\!\!\left(\phantom{\rule{0ex}{0ex}}\right)\!\!L^2\!\!-\!\!R^2$$

V wherein:
$G^1$ and $L^2$ are each independently a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:
each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
each X is independently halogen;
each R is independently hydrogen or an optionally substituted aliphatic group;
$R^2$ is hydrogen, halogen, NO$_2$, CN, N$_3$, —P(O)(OR)$_2$, —P(O)(X)$_2$, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety; and
A is the anion of a suitable acid,
comprising the steps of:
(a) providing a compound of formula I:

$$\underset{R^y}{\overset{R^x}{>}}\!\!=\!\!N\!\!-\!\!G^1\!\!-\!\!O\!\!\left(\phantom{\rule{0ex}{0ex}}\right)\!\!\left(O\right)_n\!\!\left(\phantom{\rule{0ex}{0ex}}\right)\!\!L^2\!\!-\!\!R^2$$

I or a salt thereof, wherein:
n is 10-2500;
$R^x$ and $R^y$ are each independently optionally substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur, or:
$R^x$ and $R^y$ are taken together to form a 3-8 membered saturated or partially unsaturated ring having 0-3 heteroatoms independently selected from nitrogen, oxygen, or sulfur;
$G^1$ and $L^2$ are each independently a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:
each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
each X is independently halogen;
each R is independently hydrogen or an optionally substituted aliphatic group; and
$R^2$ is hydrogen, halogen, NO$_2$, CN, N$_3$, —P(O)(OR)$_2$, —P(O)(X)$_2$, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety,
and
(b) treating said compound of formula I with a suitable acid to form said compound of formula V.

In certain embodiments, the present invention provides a method for preparing a compound of formula V:

$$\overset{\ominus}{A}\;\overset{\oplus}{H_3N}-G^1-O\!\!\left(\phantom{\rule{0ex}{0ex}}\right)\!\!\left(O\right)_n\!\!\left(\phantom{\rule{0ex}{0ex}}\right)\!\!L^2\!\!-\!\!R^2$$

V wherein:
$G^1$ and $L^2$ are each independently a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:
each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
each X is independently halogen;
each R is independently hydrogen or an optionally substituted aliphatic group;

$R^2$ is hydrogen, halogen, $NO_2$, CN, $N_3$, —P(O)(OR)$_2$, —P(O)(X)$_2$, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety; and A is the anion of a suitable acid, comprising the steps of:

(a) providing a compound of formula II:

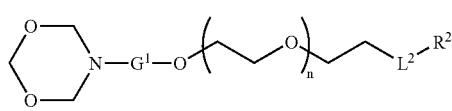

II or a salt thereof, wherein:

n is 10-2500;

$G^1$ and $L^2$ are each independently a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^2$ is hydrogen, halogen, $NO_2$, CN, $N_3$, —P(O)(OR)$_2$, —P(O)(X)$_2$, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

each X is independently halogen; and each R is independently hydrogen or an optionally substituted aliphatic group, and (b) treating said compound of formula II with a suitable acid to form said compound of formula V.

In certain embodiments, the present invention provides a method for preparing a compound of formula V:

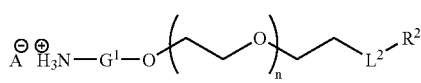

V wherein:

$G^1$ and $L^2$ are each independently a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

each X is independently halogen;

each R is independently hydrogen or an optionally substituted aliphatic group;

$R^2$ is hydrogen, halogen, $NO_2$, CN, $N_3$, —P(O)(OR)$_2$, —P(O)(X)$_2$, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety; and A is the anion of a suitable acid, comprising the steps of:

(a) providing a compound of formula III:

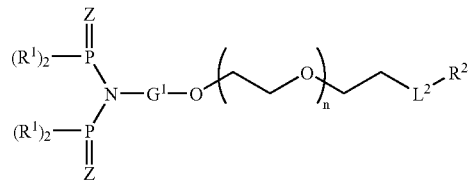

III or a salt thereof, wherein:

n is 10-2500;

each Z is independently oxygen or sulfur;

each $R^1$ is independently an optionally substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur;

$G^1$ and $L^2$ are each independently a valence bond or a bivalent, saturated or unsaturated, straight or branched $C_{1-12}$ hydrocarbon chain, wherein 06 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

each X is independently halogen;

each R is independently hydrogen or an optionally substituted aliphatic group; and $R^2$ is hydrogen, halogen, $NO_2$, CN, $N_3$, —P(O)(OR)$_2$, —P(O)(X)$_2$, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
and
(b) treating said compound of formula III with a suitable acid to form said compound of formula V.

In other embodiments, the present invention provides a method for preparing a compound of formula V:

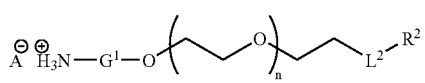

wherein:
$G^1$ and $L^2$ are each independently a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—,
wherein:
each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
each X is independently halogen;
each R is independently hydrogen or an optionally substituted aliphatic group;
$R^2$ is hydrogen, halogen, NO$_2$, CN, N$_3$, —P(O)(OR)$_2$, —P(O)(X)$_2$, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety; and
A is the anion of a suitable acid,
comprising the steps of:
(a) providing a compound of formula IV:

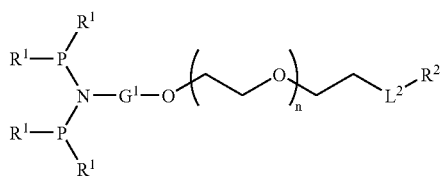

or a salt thereof, wherein:
n is 10-2500;
each $R^1$ is independently an optionally substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur;
$G^1$ and $L^2$ are each independently a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—,
wherein:
each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
each X is independently halogen;
each R is independently hydrogen or an optionally substituted aliphatic group; and
$R^2$ is hydrogen, halogen, NO$_2$, CN, N$_3$, —P(O)(OR)$_2$, —P(O)(X)$_2$, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
and
(b) treating said compound of formula IV with a suitable acid to form said compound of formula V.

Each n, $G^1$, $L^2$, and $R^2$ group of compounds of formula V are as described herein for compounds of any of formulae I, II, III, and IV in classes and subclasses, both singly and in combination.

As described generally above, a compound of formula V is prepared by treating a compound of any of formulae I, II, III, and IV with a suitable acid. One of ordinary skill in the art will recognize that compounds of formulae I, II, III, and IV contain acid-labile amino protecting groups. Such amino protecting groups liberate an amine salt, i.e. of formula V, upon treatment with a suitable acid. Such deprotection conditions are well known in the art and include those described in detail in Greene. As used herein, the term "suitable acid" refers to an acid (inorganic or organic) that is capable of deprotecting a compound of any of formulae I, II, III, and IV to form the amine salt of formula V. Such acids include inorganic acid such as hydrochloric acid, hydrobromic acid, phosphoric acid, sulfuric acid or perchloric acid. It is also contemplated that acids include organic acid such as as trifluoroacetic acid, acetic, acetic acid, oxalic acid, maleic acid, tartaric acid, citric acid, succinic acid, malonic acid, and the like, or by using other methods used in the art such as ion exchange.

As defined generally above, the A$^-$ group of formula V is the anion of a suitable acid. Thus, the A$^-$ group includes anions of inorganic acid such as hydrochloric acid, hydrobromic acid, phosphoric acid, sulfuric acid or perchloric acid. It is also contemplated that A$^-$ is, in certain embodiments, the anion of an organic acid such as as trifluoroacetic acid, acetic, acetic acid, oxalic acid, maleic acid, tartaric acid, citric acid, succinic acid, malonic acid, and the like. In certain embodiments, the suitable acid is trifluoroacetic acid and A$^-$ is the anion of trifluoroacetic acid.

Compounds of formula V are particularly useful for preparing block copolymers by the controlled ring-opening polymerization of cyclic monomers such as N-carboxy anhydrides (NCAs), lactams, and cyclic imides wherein the polymerization is initiated by the amine salt functionality of the compound of formula V. Such methods are described in detail in U.S. patent application Ser. No. 11/325,020, filed Jan. 4, 2006, the entirety of which is hereby incorporated herein by reference.

In certain embodiments, the method for preparing a compound of formula V from a compound of any of formulae I, II, III, and IV further comprises the step of treating the compound of formula V with a suitable base to form a compound of formula V-a:

$$H_2N—G^1—O{\left(\!\!\begin{array}{c}\phantom{x}\\\phantom{x}\end{array}\!\!O\right)}_n L^2 R^2$$
V-a wherein each of $G^1$, n, $L^2$, and $R^2$ is as defined above and described in classes and subclasses herein singly and in combination.

One of ordinary skill in the art would appreciate that a variety of bases are suitable for forming the free-base compound of formula V-a from the salt form of formula V. Such bases are well known in the art. In certain embodiments, the suitable base is pyridine, or a derivative thereof, such as dimethylaminopyridine ("DMAP"), lutidine or collidine. In other embodiments, the base utilized at step (d) is dimethylaminopyridine ("DMAP"). In still other embodiments, inorganic bases are utilized and include ammonia, potassium hydroxide, sodium hydroxide, sodium carbonate, sodium bicarbonate, potassium carbonate, or potassium bicarbonate.

Exemplary compounds of the present invention are set forth in the Tables A through D, below.

TABLE A

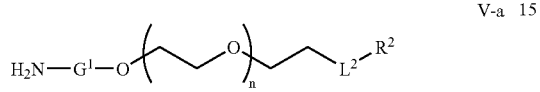

| # | $R^a$ | $R^b$ |
|---|---|---|

(table continues with entries 1–8 showing benzophenone imine $R^a$ groups and various $R^b$ groups: alkyne, $H_2N$-ethyl, $N_3$-ethyl, aldehyde, HS-ethyl, norbornene-imide, maleimide, -OH)

TABLE A-continued $$R^a\text{O}\left(\text{\_\_\_O}\right)_n R^b$$

| # | $R^a$ | $R^b$ |
|---|-------|-------|
| 9 | (Ph)₂P(=O)–N(–)–P(=O)(Ph)₂ group attached via alkyl chain | –CH₂–C≡CH |
| 10 | (Ph)₂P(=O)–N(–)–P(=O)(Ph)₂ group attached via alkyl chain | H₂N–CH₂CH₂– |
| 11 | (Ph)₂P(=O)–N(–)–P(=O)(Ph)₂ group attached via alkyl chain | N₃–CH₂CH₂– |
| 12 | (Ph)₂P(=O)–N(–)–P(=O)(Ph)₂ group attached via alkyl chain | OHC–CH₂– |
| 13 | (Ph)₂P(=O)–N(–)–P(=O)(Ph)₂ group attached via alkyl chain | HS–CH₂CH₂– |
| 14 | (Ph)₂P(=O)–N(–)–P(=O)(Ph)₂ group attached via alkyl chain | exo-oxanorbornene dicarboximide-N–CH₂CH₂– |
| 15 | (Ph)₂P(=O)–N(–)–P(=O)(Ph)₂ group attached via alkyl chain | maleimide-N–CH₂CH₂– |
| 16 | (Ph)₂P(=O)–N(–)–P(=O)(Ph)₂ group attached via alkyl chain | HO–CH₂CH₂– |
| 17 | (Me)₂P(=O)–N(–)–P(=O)(Me)₂ attached via ethyl chain | –CH₂–C≡CH |

TABLE A-continued $$R^a\text{-}O\text{-}(\text{-}CH_2CH_2O\text{-})_n\text{-}R^b$$

| # | $R^a$ | $R^b$ |
|---|-------|-------|
| 18 | dimethylphosphoryl-N(dimethylphosphoryl)-propyl- | H₂N-CH₂CH₂- |
| 19 | dimethylphosphoryl-N(dimethylphosphoryl)-propyl- | N₃-CH₂CH₂- |
| 20 | dimethylphosphoryl-N(dimethylphosphoryl)-propyl- | OHC-CH₂- |
| 21 | dimethylphosphoryl-N(dimethylphosphoryl)-propyl- | HS-CH₂CH₂- |
| 22 | dimethylphosphoryl-N(dimethylphosphoryl)-propyl- | N-oxanorbornene-dicarboximide-propyl- |
| 23 | dimethylphosphoryl-N(dimethylphosphoryl)-propyl- | maleimido-propyl- |
| 24 | dimethylphosphoryl-N(dimethylphosphoryl)-propyl- | HO-CH₂CH₂- |

TABLE B $$R^a\text{-}O\text{-}(\text{-}CH_2CH_2O\text{-})_n\text{-}R^b$$

| Entry | $R^a$ | $R^b$ |
|-------|-------|-------|
| 25 | Ph₂C=N-CH₂CH₂- | CH₃O-CH₂CH₂- |
| 26 | (Ph)₃P(=O)-N(P(=O)(Ph)₂)-CH₂CH₂- | CH₃O-CH₂CH₂- |
| 27 | dimethylphosphoryl-N(dimethylphosphoryl)-propyl- | CH₃O-CH₂CH₂- |

TABLE C $$R^a\text{-}O\text{-}(\text{-}CH_2CH_2O\text{-})_n\text{-}R^b$$

| # | $R^a$ | $R^b$ |
|---|-------|-------|
| 28 | F₃C-CO₂⁻ ·H₃N⁺-CH₂CH₂- | HC≡C-CH₂- |
| 29 | F₃C-CO₂⁻ ·H₃N⁺-CH₂CH₂- | N₃-CH₂CH₂- |
| 30 | F₃C-CO₂⁻ ·H₃N⁺-CH₂CH₂- | N-oxanorbornene-dicarboximide-propyl- |
| 31 | Cl⁻ ·H₃N⁺-CH₂CH₂- | HC≡C-CH₂- |
| 32 | Cl⁻ ·H₃N⁺-CH₂CH₂- | N₃-CH₂CH₂- |

TABLE C-continued

R$^a$—O—(—O—)$_n$—R$^b$

| # | R$^a$ | R$^b$ |
|---|---|---|
| 33 | Cl$^\ominus$ H$_3$N$^\oplus$—CH$_2$CH$_2$— | (N-ethyl-oxanorbornene-dicarboximide group) |

TABLE D

R$^a$—O—(—O—)$_n$—R$^b$

| # | R$^a$ | R$^b$ |
|---|---|---|
| 34 | F$_3$C—C(O)—O$^\ominus$ H$_3$N$^\oplus$—CH$_2$CH$_2$— | —CH$_2$CH$_2$—O—CH$_3$ |
| 35 | Cl$^\ominus$ H$_3$N$^\oplus$—CH$_2$CH$_2$— | —CH$_2$CH$_2$—O—CH$_3$ |

4. General Methods of Providing the Present Compounds

Compounds of this invention may be prepared in general by synthetic methods known to those skilled in the art for analogous compounds and as illustrated by the general schemes and the preparative examples that follow. In certain embodiments, compounds of the present invention are prepared by methods as described in detail in United States patent application entitled "Heterobifunctional poly(ethylene glycol) and Uses Thereof" filed Oct. 24, 2005, and given Ser. No. 11/256,735, the entirety of which is hereby incorporated herein by reference.

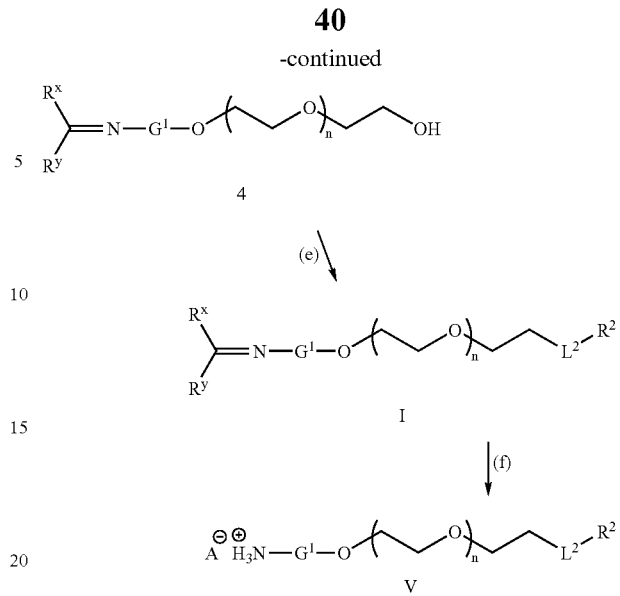

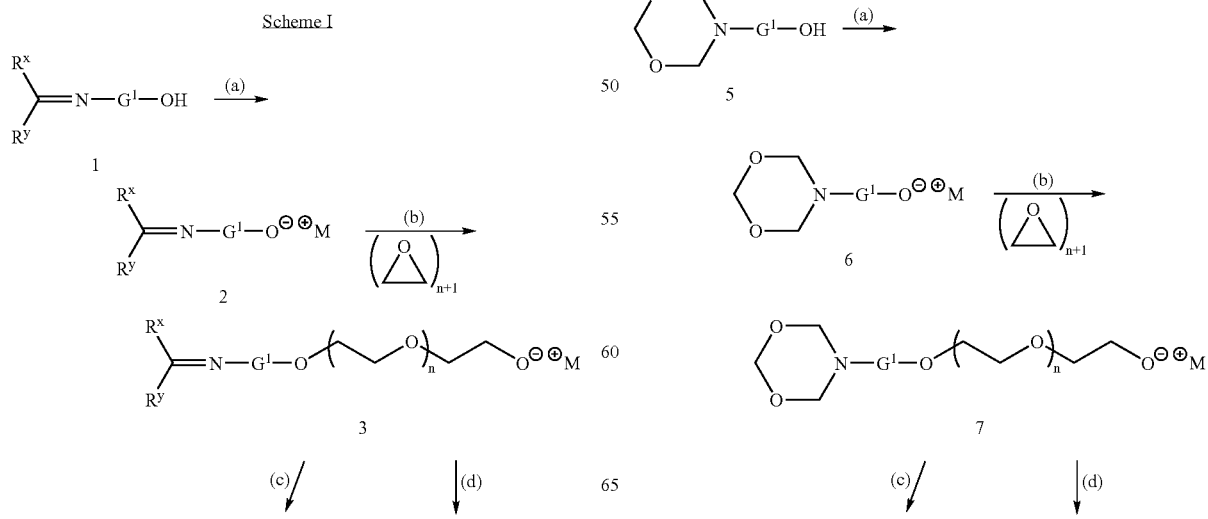

Scheme I above shows a general method for preparing compounds of the present invention. At step (a), the polymerization initiator is treated with a suitable base to form 2. A variety of bases are suitable for the reaction at step (a). Such bases include, but are not limited to, potassium naphthalenide, diphenylmethyl potassium, triphenylmethyl potassium, and potassium hydride. At step (b), the resulting anion is treated with ethylene oxide to form the polymer 3. Polymer 3 can be transformed at step (d) to a compound of formula I directly by terminating the living polymer chain-end of 3 with a suitable polymerization terminator to afford a compound of formula I. Alternatively, polymer 3 may be quenched at step (c) to form the hydroxyl compound 4. Compound 4 is then derivatized (e) to afford a compound of formula I by methods known in the art. A compound of formula I can be treated with a suitable acid (f) to afford a compound of formula V.

In a similar fashion, compounds of formula II are prepared as depicted in Scheme II below.

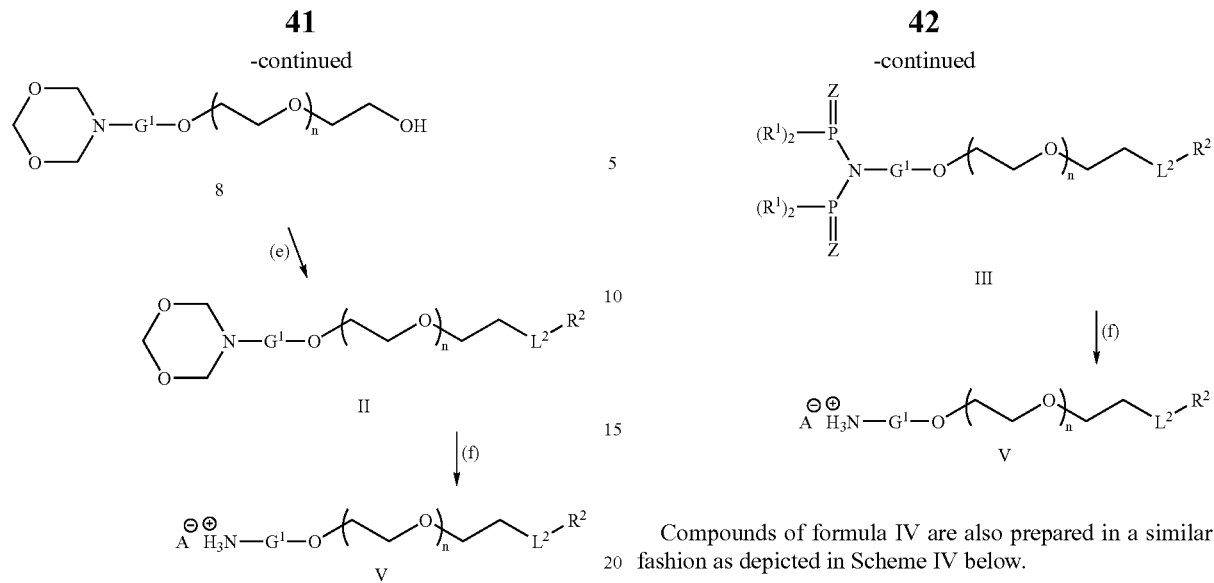
In a similar fashion, compounds of formula III are prepared as depicted in Scheme III below.
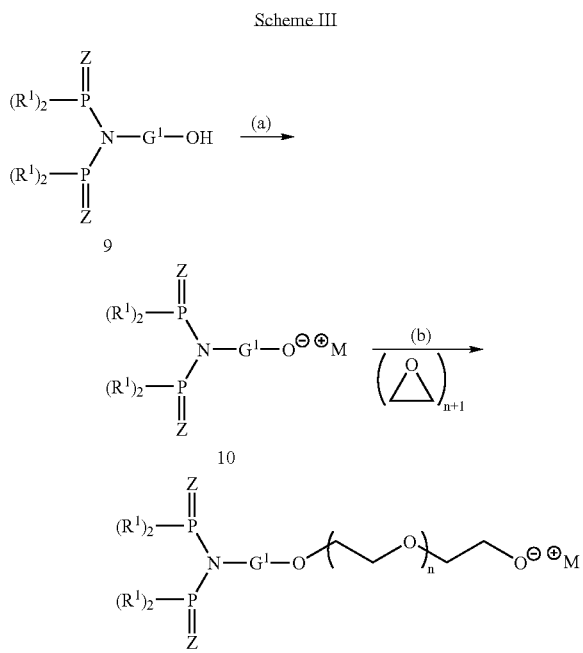
Compounds of formula IV are also prepared in a similar fashion as depicted in Scheme IV below.
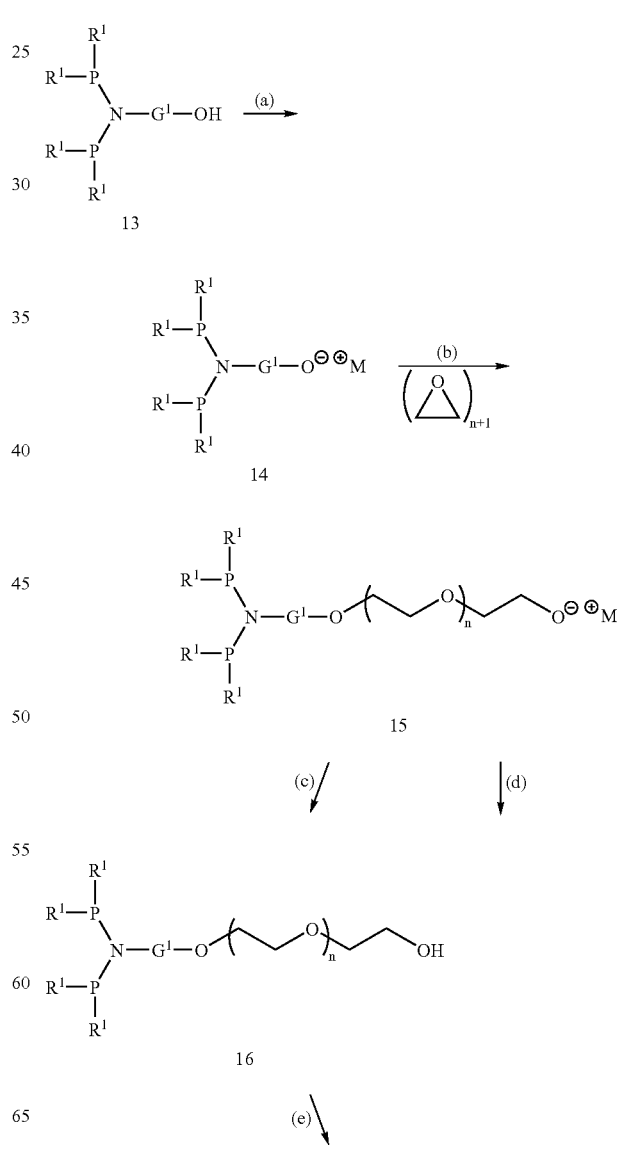

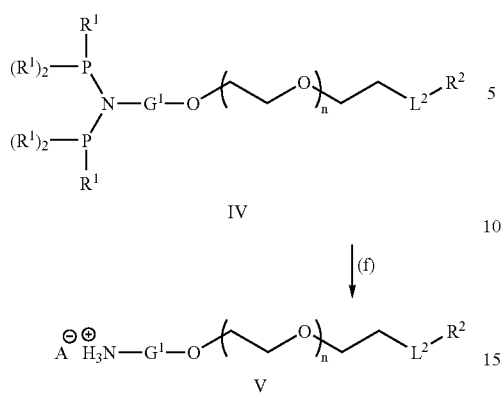
IV
↓ (f)
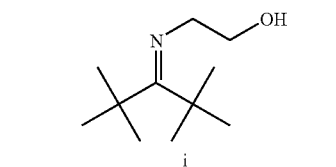
V
In certain embodiments, the polymerization initiator compound I (Scheme I) is selected from those set forth in Table 2-a:
TABLE 2-a
Representative Polymerization Initiators
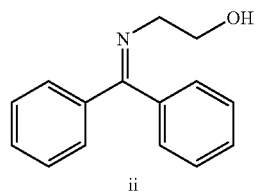
i
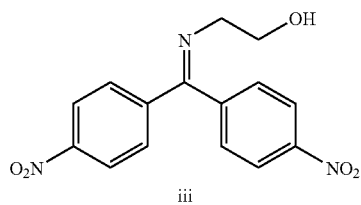
ii
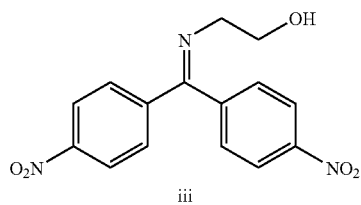
iii
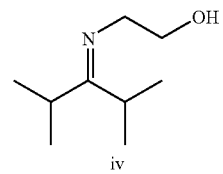
iv
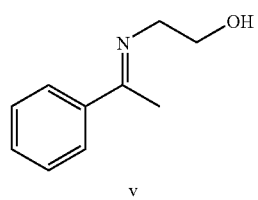
v
TABLE 2-a-continued
Representative Polymerization Initiators
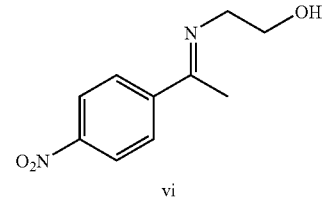
vi
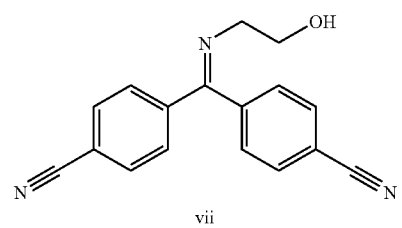
vii
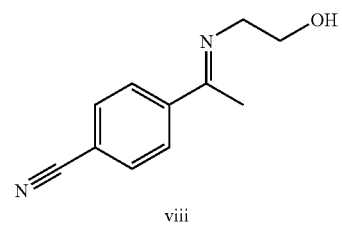
viii
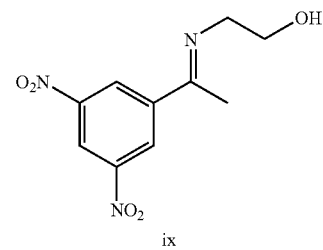
ix
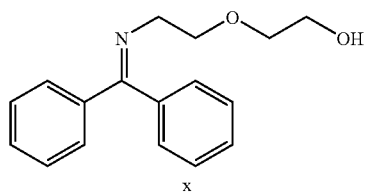
x
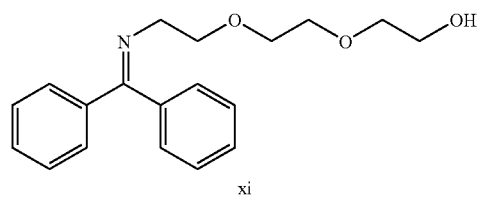
xi
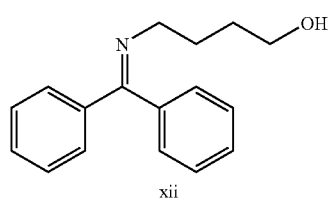
xii TABLE 2-a-continued
Representative Polymerization Initiators
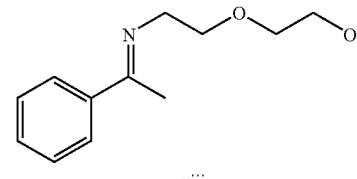
xiii
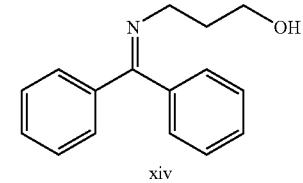
xiv
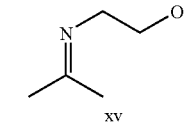
xv
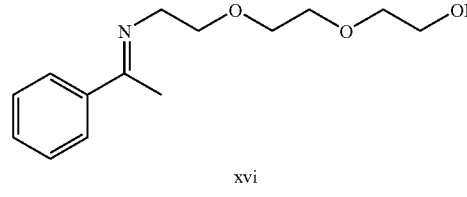
xvi
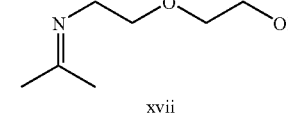
xvii
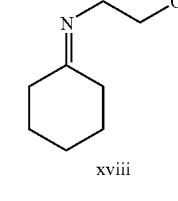
xviii
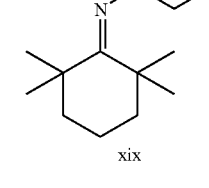
xix
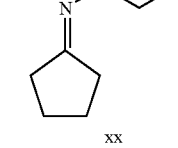
xx
TABLE 2-a-continued
Representative Polymerization Initiators
xxi
xxii
xxiii
xxiv
xxv
xxvi
xxvii TABLE 2-a-continued
Representative Polymerization Initiators
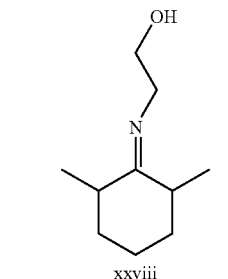
xxviii
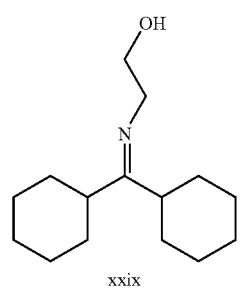
xxix
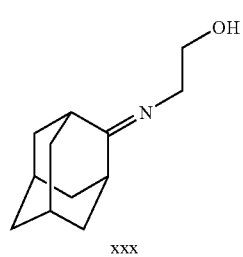
xxx
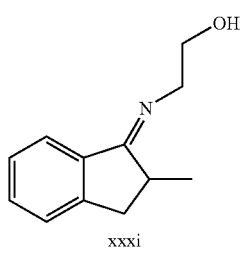
xxxi
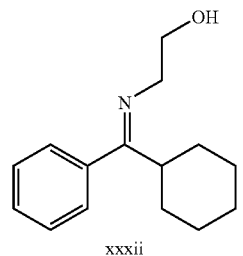
xxxii
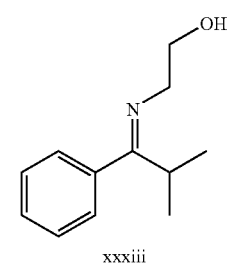
xxxiii
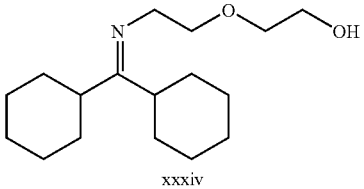
xxxiv
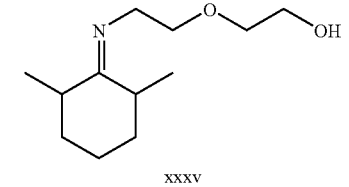
xxxv
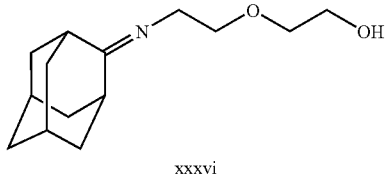
xxxvi
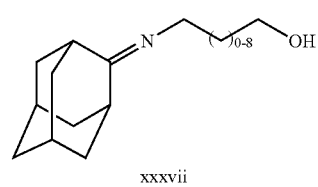
xxxvii
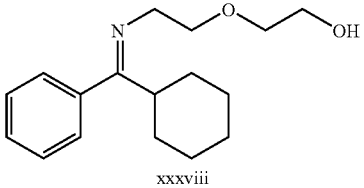
xxxviii
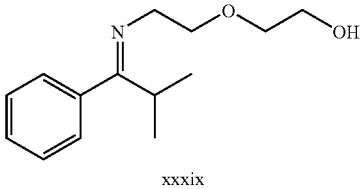
xxxix
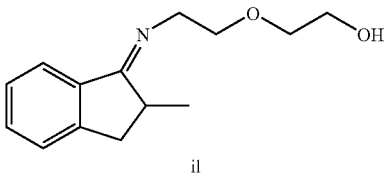
il
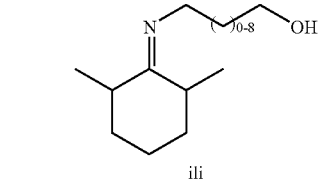
ili

TABLE 2-a-continued

Representative Polymerization Initiators

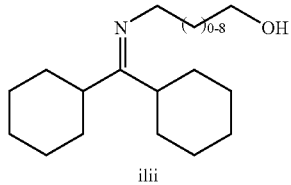

ilii

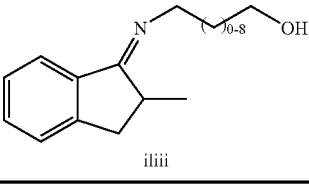

iliii

In other embodiments, the polymerization initiator compound 5 (Scheme II) is selected from those set forth in Table 2-b.

TABLE 2-b

Representative Polymerization Initiators

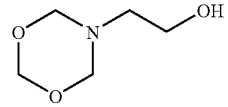

a

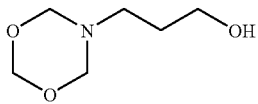

b

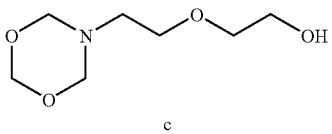

c

In other embodiments, the polymerization initiator compound 9 (Scheme III) is selected from those set forth in Table 2-c.

TABLE 2-c

Representative Polymerization Initiators

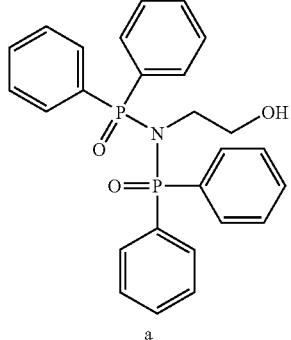

a

TABLE 2-c-continued

Representative Polymerization Initiators

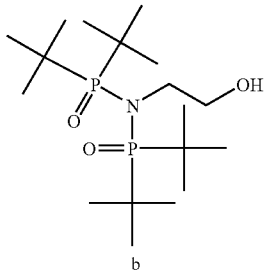

b

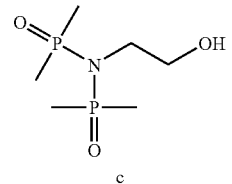

c

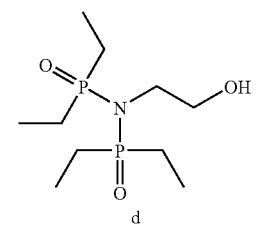

d

In other embodiments, the polymerization initiator compound 13 (Scheme IV) is selected from those set forth in Table 2-d.

TABLE 2-d

Representative Polymerization Initiators

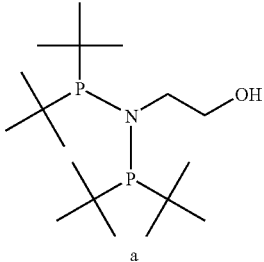

a

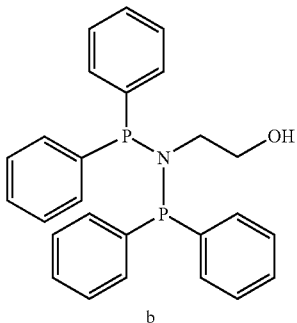

b

Referring back to Schemes 1-4, above, one of ordinary skill in the art will recognize that the derivatization of a compound of formula 4 to form a compound of formula I (and, likewise, a compound of formula 8 to a compound of formula II; a compound of formula 12 to a compound of formula III, or a compound of formula 16 to a compound of formula IV) may be achieved in a single step or via a multi-step process. For example, the hydroxyl group of formula 4 can be converted to a suitable leaving group which is then displaced by a nucleophile to form a compound of formula I. Suitable leaving groups are well known in the art, e.g., see, "Advanced Organic Chemistry," Jerry March, 5th Ed., pp. 351-357, John Wiley and Sons, N.Y. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, and diazonium moieties. Examples of suitable leaving groups include chloro, iodo, bromo, fluoro, methanesulfonyloxy (mesyloxy), tosyloxy, triflyloxy, nitro-phenylsulfonyloxy (nosyloxy), and bromo-phenylsulfonyloxy (brosyloxy).

In certain embodiments, the present invention provides a compound of formula I-i:

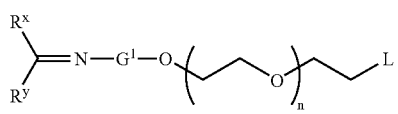

or a salt thereof, wherein each of n, $G^1$, $R^x$, and $R^y$ is as defined above and described in classes and subclasses herein, independently, singly and in combination and L is a suitable leaving group as described above.

In certain embodiments, the present invention provides a compound of formula II-ii:

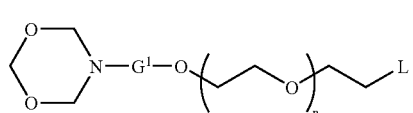

or a salt thereof, wherein each of n and $G^1$ is as defined above and described in classes and subclasses herein, independently, singly and in combination and L is a suitable leaving group as described above.

In certain embodiments, the present invention provides a compound of formula

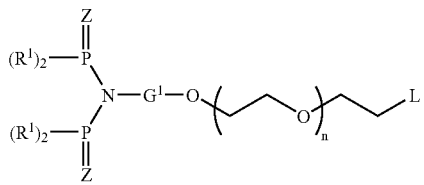

or a salt thereof, wherein each of n, $G^1$, $R^1$, and Z is as defined above and described in classes and subclasses herein, independently, singly and in combination and L is a suitable leaving group as described above.

In certain embodiments, the present invention provides a compound of formula IV-a:

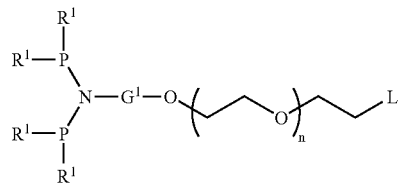

or a salt thereof, wherein each of n, $G^1$, and $R^1$ is as defined above and described in classes and subclasses herein, independently, singly and in combination and L is a suitable leaving group as described above.

According to an alternate embodiment, the suitable leaving group may be generated in situ within a reaction medium. For example, a leaving group may be generated in situ from a precursor of that compound wherein said precursor contains a group readily replaced by said leaving group in situ.

Derivatization of the hydroxyl group of formula 4 can be achieved using methods known to one of ordinary skill in the art to obtain a variety of compounds. For example, said hydroxyl group may be transformed to a protected hydroxyl group, or, alternatively, to a suitable leaving group. Hydroxyl protecting groups are well known and include those described above and herein. Such transformations are known to one skilled in the art and include, among others, those described herein.

An exemplary transformation includes coupling of the hydroxyl group of formula 4 with an acid to form an ester thereof. Once of ordinary skill in the art would recognize that this transformation would result in compounds of formula I wherein $L^2$ is a bivalent, saturated or unsaturated, straight or branched $C_{1-12}$ alkylene chain, as defined and described herein, wherein the terminal methylene group is replaced by —C(O)O—. Such coupling reactions are well known in the art. In certain embodiments, the coupling is achieved with a suitable coupling reagent. Such reagents are well known in the art and include, for example, DCC and EDC, among others. In other embodiments, the carboxylic acid moiety is activated for use in the coupling reaction. Such activation includes formation of an acyl halide, use of a Mukaiyama reagent, and the like.

These methods, and others, are known to one of ordinary skill in the art, e.g., see, "Advanced Organic Chemistry," Jerry March, 5th Ed., pp. 351-357, John Wiley and Sons, N.Y.

In certain embodiments, the $R^2$-$L^2$- group of any of formulae I, II, III, and IV is incorporated at either of steps (b) or (e) by derivatization of the hydroxyl group of formula 4 (or 8, 12, or 16, as the case may be) via Mitsunobu coupling. The Mitsunobu reaction is a mild method for achieving formal substitution of the hydroxyl group using azodicarboxylic esters/amides and triphenylphosphine (TPP) or trialkylphosphines or phosphites. In addition, other azo compounds have been developed as alternatives to the traditional azodicarboxylic esters diethylazodicarboxylate (DEAD) and diisopropylazodicarboxylate (DIAD). These include dibenzyl azodicarboxylate (DBAD), N,N,N',N'-tetramethylazodicarbonamide (TMAD), and dipiperidyl azodicarboxylate (DPAD). Mitsunobu coupling provides access to terminal groups including, but not limited to, halides, azide, amines, esters, ethers, thioethers and isothiocyanates. Accordingly, it will be appreciated that a variety of compounds of any of formulae I, II, III, and IV are obtained by the derivatization of the hydroxyl group of formula 4 (or 8, 12, or 16, as the case may be) by Mitsunobu reaction.

In certain embodiments, the polymerization terminating agent is one that is capable of Mistunobu coupling. These include optionally substituted phenols, optionally substituted thiophenols, cyclic imides, carboxylic acids, azide, and other reagents capable of Mitsunobu coupling. Such Mitsunobu terminating agents include, but are not limited to, those set forth in Table 3, below.

TABLE 3

Representative Mitsunobu Polymerization Terminating Agents

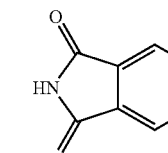

TABLE 3-continued

Representative Mitsunobu Polymerization Terminating Agents

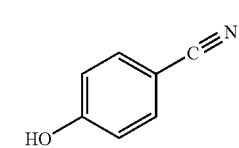

TABLE 3-continued
Representative Mitsunobu Polymerization Terminating Agents
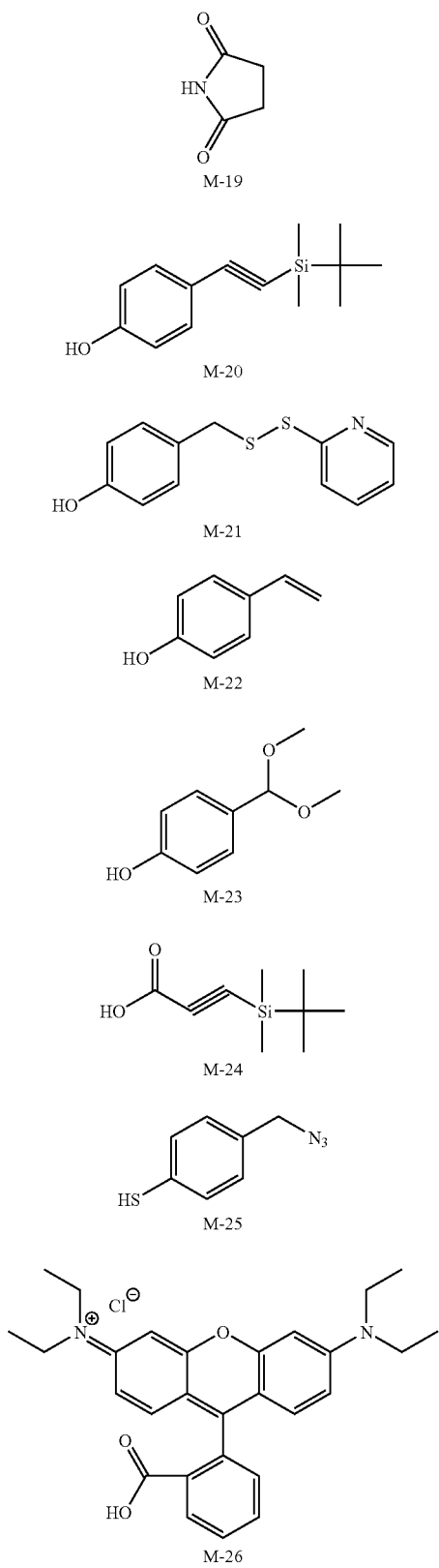
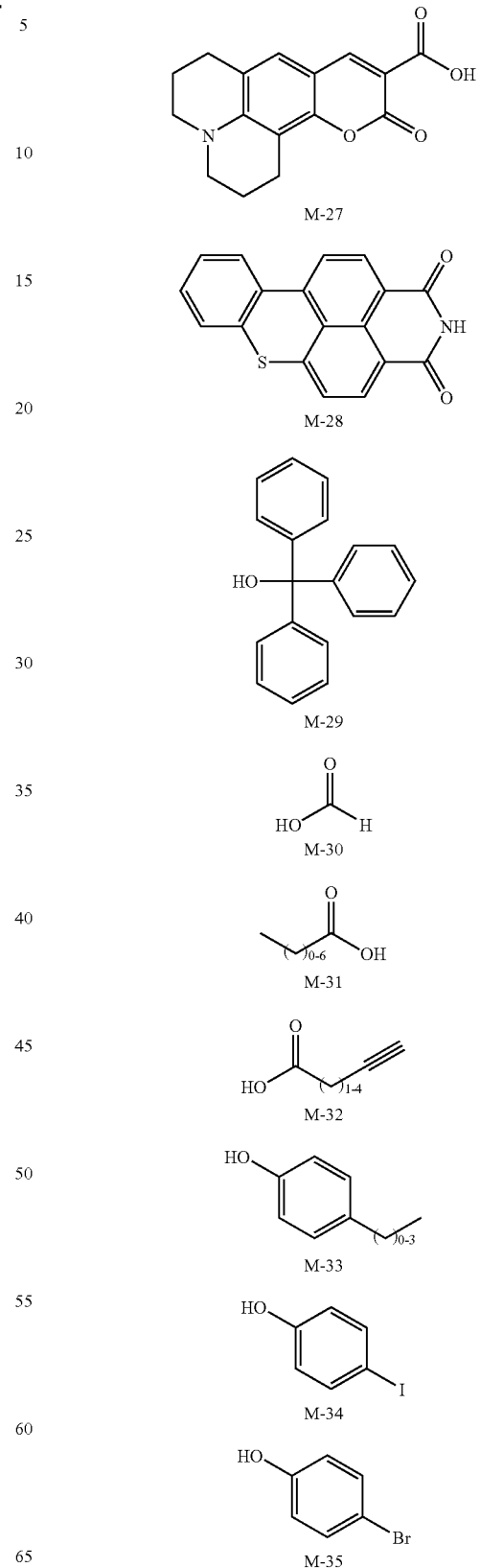

TABLE 3-continued
Representative Mitsunobu Polymerization Terminating Agents
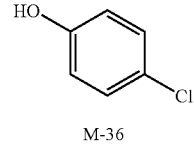
M-36
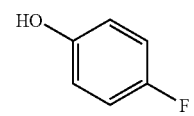
M-37
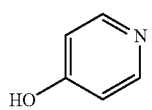
M-38
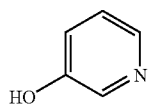
M-39
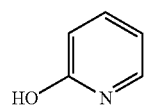
M-40
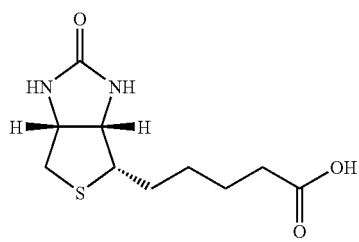
M-41
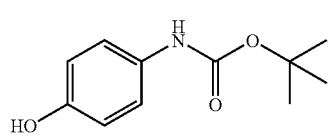
M-42
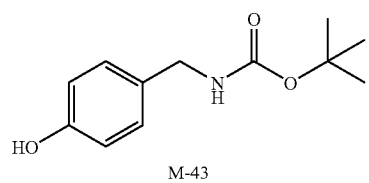
M-43
TABLE 3-continued
Representative Mitsunobu Polymerization Terminating Agents
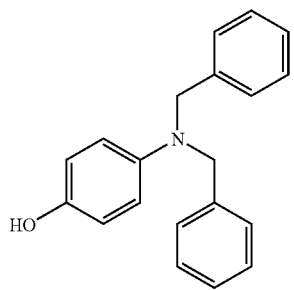
M-44
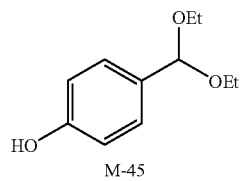
M-45
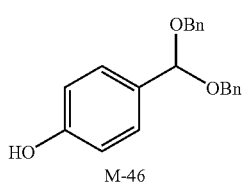
M-46
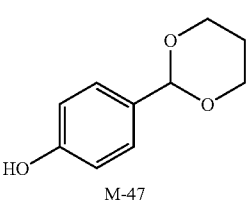
M-47
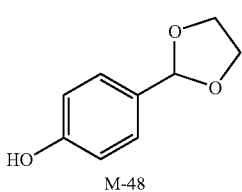
M-48
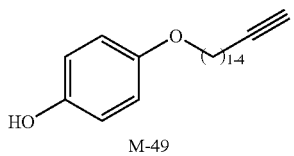
M-49
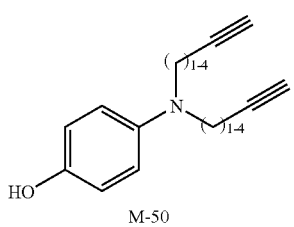
M-50

TABLE 3-continued
Representative Mitsunobu Polymerization Terminating Agents
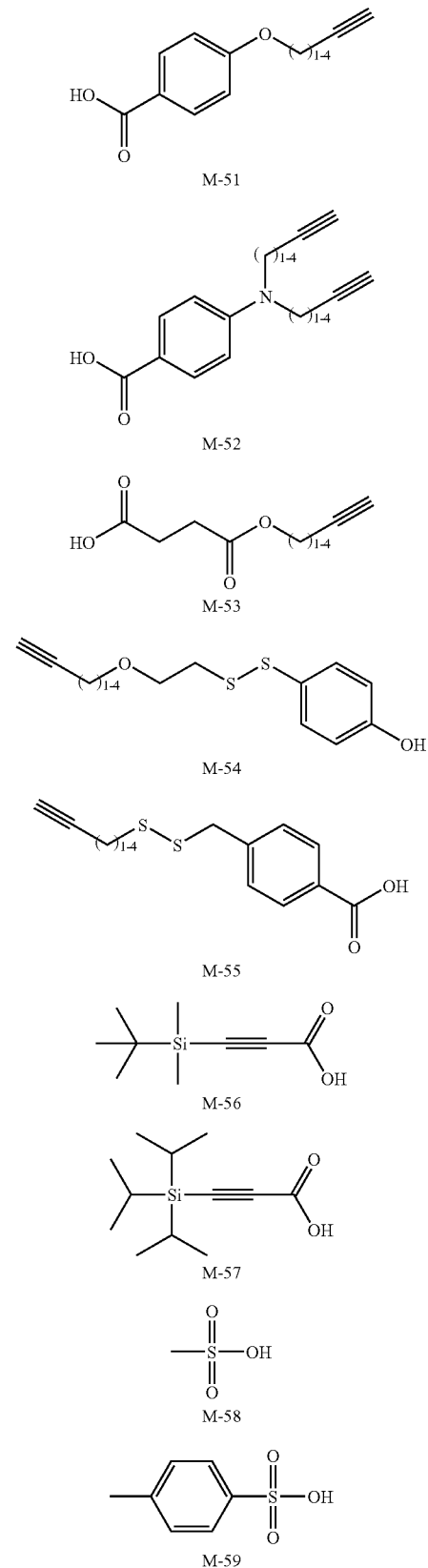
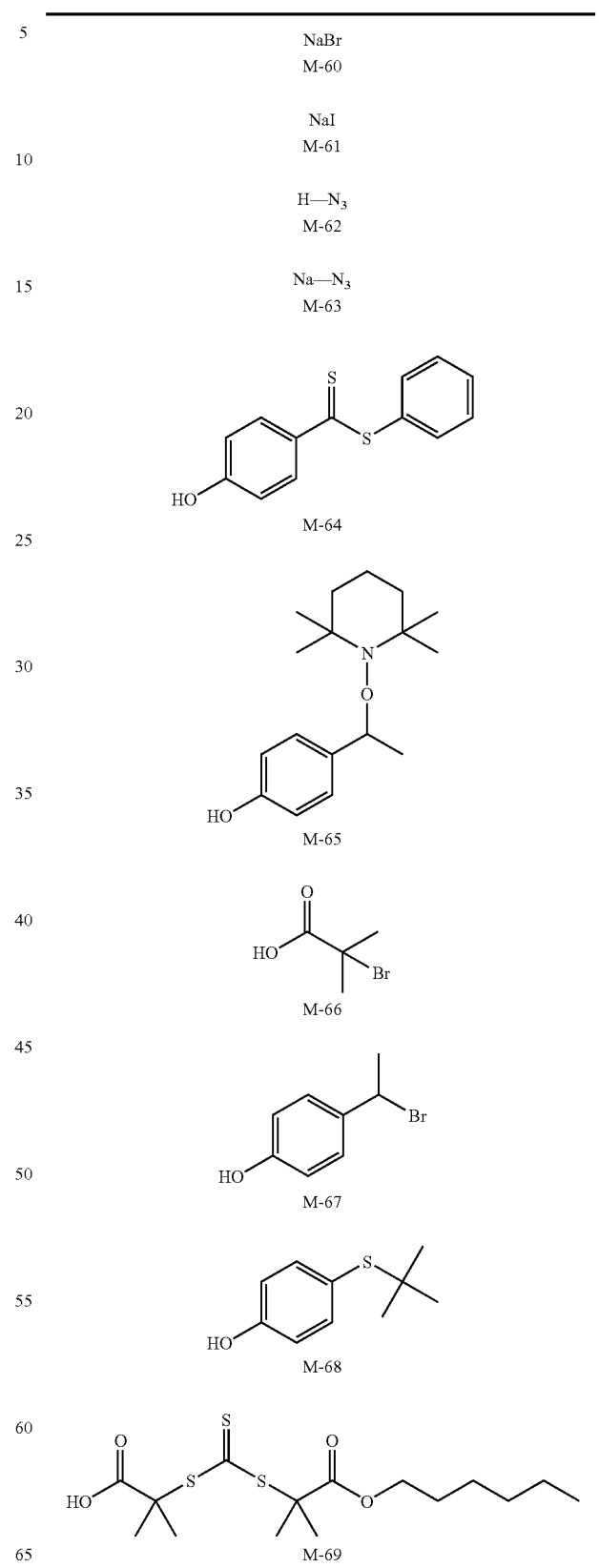

TABLE 3-continued
Representative Mitsunobu Polymerization Terminating Agents
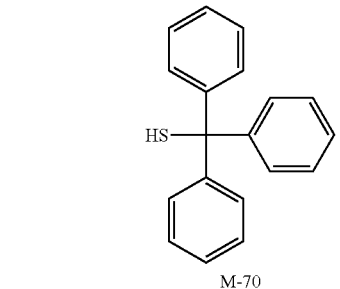
M-70
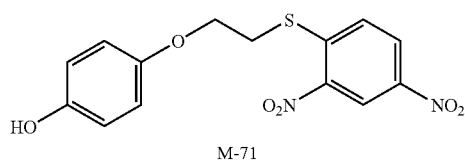
M-71
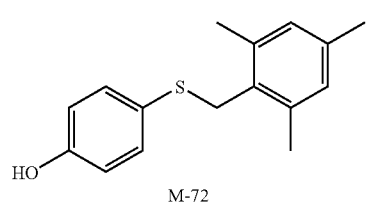
M-72
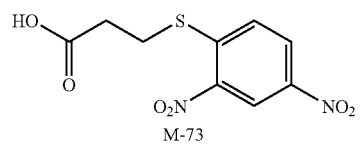
M-73
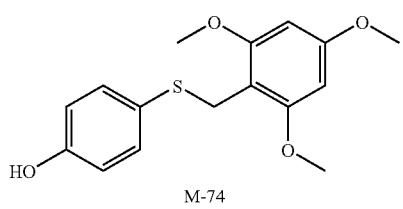
M-74
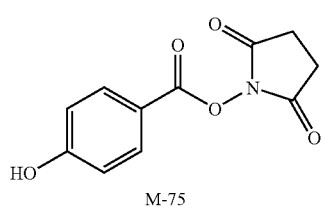
M-75
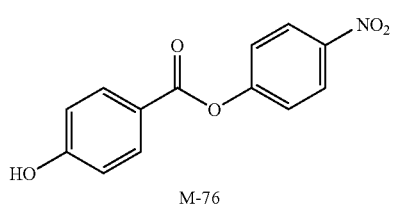
M-76
TABLE 3-continued
Representative Mitsunobu Polymerization Terminating Agents
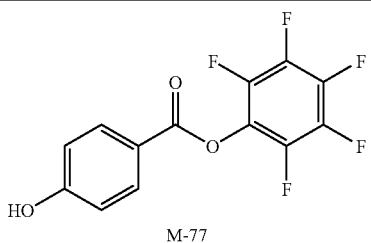
M-77
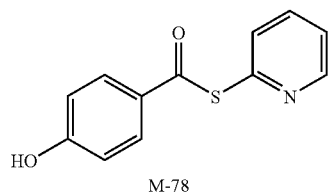
M-78
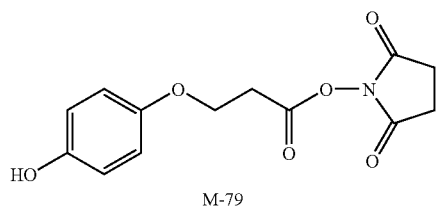
M-79
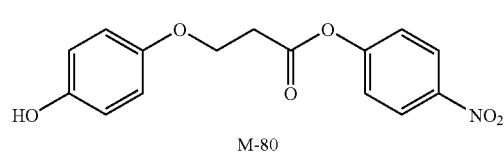
M-80
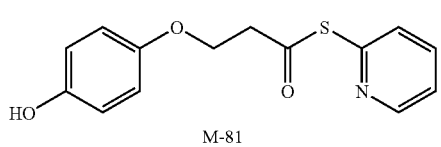
M-81
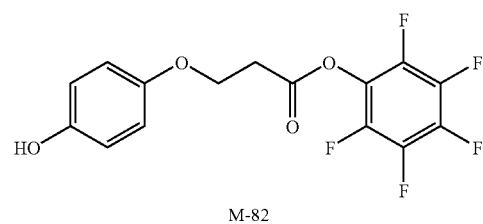
M-82
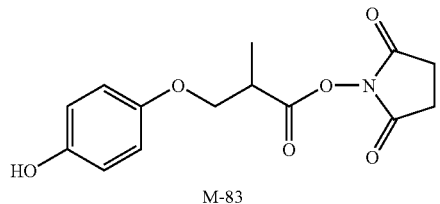
M-83
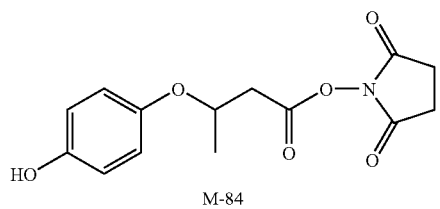
M-84

TABLE 3-continued

Representative Mitsunobu Polymerization Terminating Agents

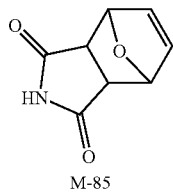

M-85

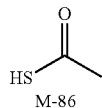

M-86

In other embodiments, the $R^2$-$L^2$- group of any of formulae I, II, III, and IV is incorporated by derivatization of the hydroxyl group of formula 4 (or 8, 12, or 16, as the case may be) via anhydride coupling. One of ordinary skill in the art would recognize that anhydride polymerization terminating agents containing an azide, an aldehyde, a protected hydroxyl, an alkyne, and other groups, may be used to incorporate said azide, said aldehyde, said protected hydroxyl, said alkyne, and other groups into the $R^2$-$L^2$- group of compounds of any of formulae I, II, III, and IV. It will also be appreciated that such anhydride polymerization terminating agents are also suitable for terminating the living polymer chain-end of a compound of formula 3 (or 7, 11, or 15, as the case may be). Such anhydride polymerization terminating agents include, but are not limited to, those set forth in Table 4, below.

TABLE 4

Representative Anhydride Polymerization Terminating Agents

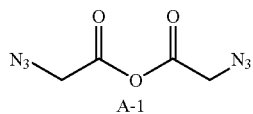

A-1

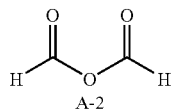

A-2

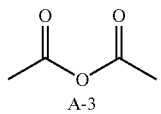

A-3

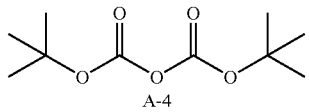

A-4

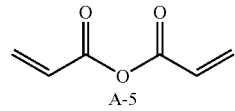

A-5

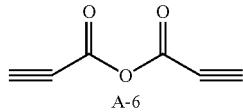

A-6

TABLE 4-continued

Representative Anhydride Polymerization Terminating Agents

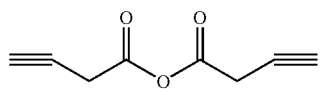

A-7

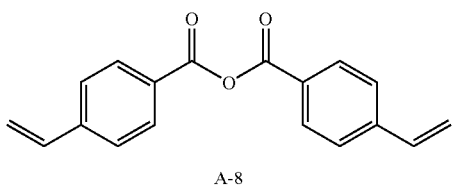

A-8

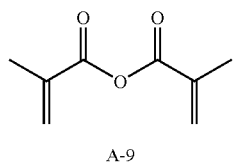

A-9

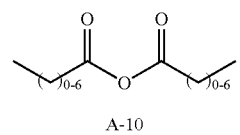

A-10

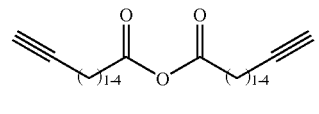

A-11

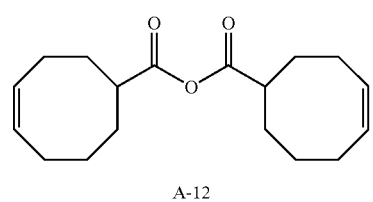

A-12

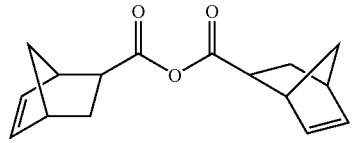

A-13

In other embodiments, the $R^2$-$L^2$- group of any of formulae I, II, III, and IV is incorporated by derivatization of the hydroxyl group of formula 4 (or 8, 12, or 16, as the case may be) via reaction with a polymerization terminating agent having a suitable leaving group. It will also be appreciated that such polymerization terminating agents are also suitable for terminating the living polymer chain-end of a compound of formula 3 (or 7, 11, or 15, as the case may be). Examples of such polymerization terminating agents include, but are not limited to, those set forth in Table 5, below.

TABLE 5
Representative Polymerization Terminating Agents
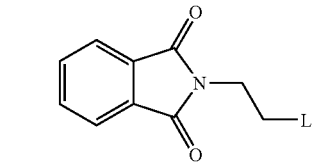
L-1
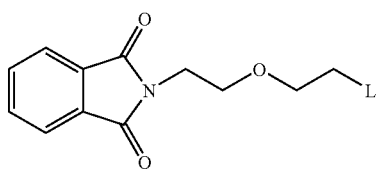
L-2
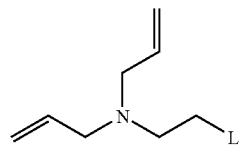
L-3
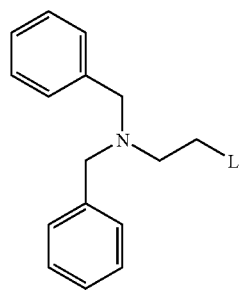
L-4
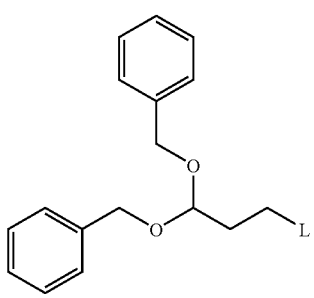
L-5
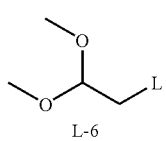
L-6
TABLE 5-continued
Representative Polymerization Terminating Agents
L-7
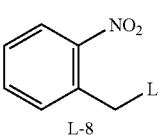
L-8
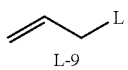
L-9
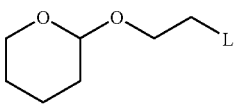
L-10
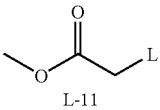
L-11
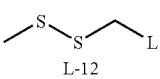
L-12
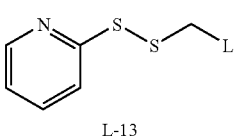
L-13
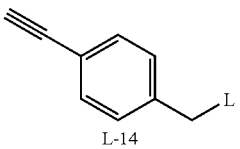
L-14
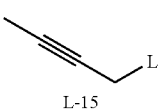
L-15
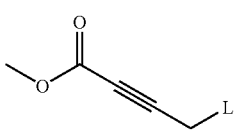
L-16
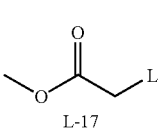
L-17

TABLE 5-continued
Representative Polymerization Terminating Agents
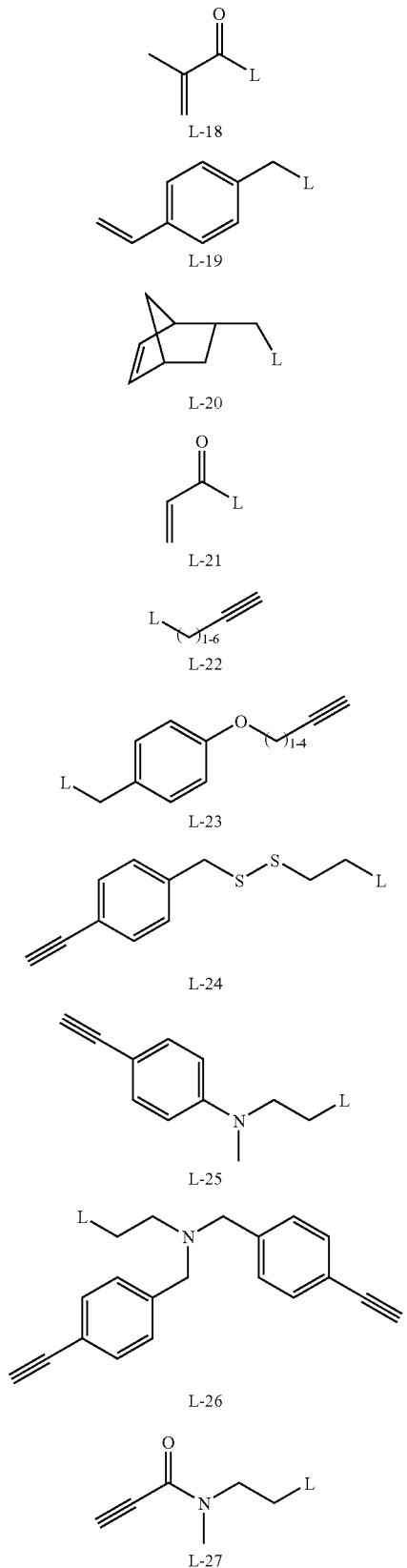
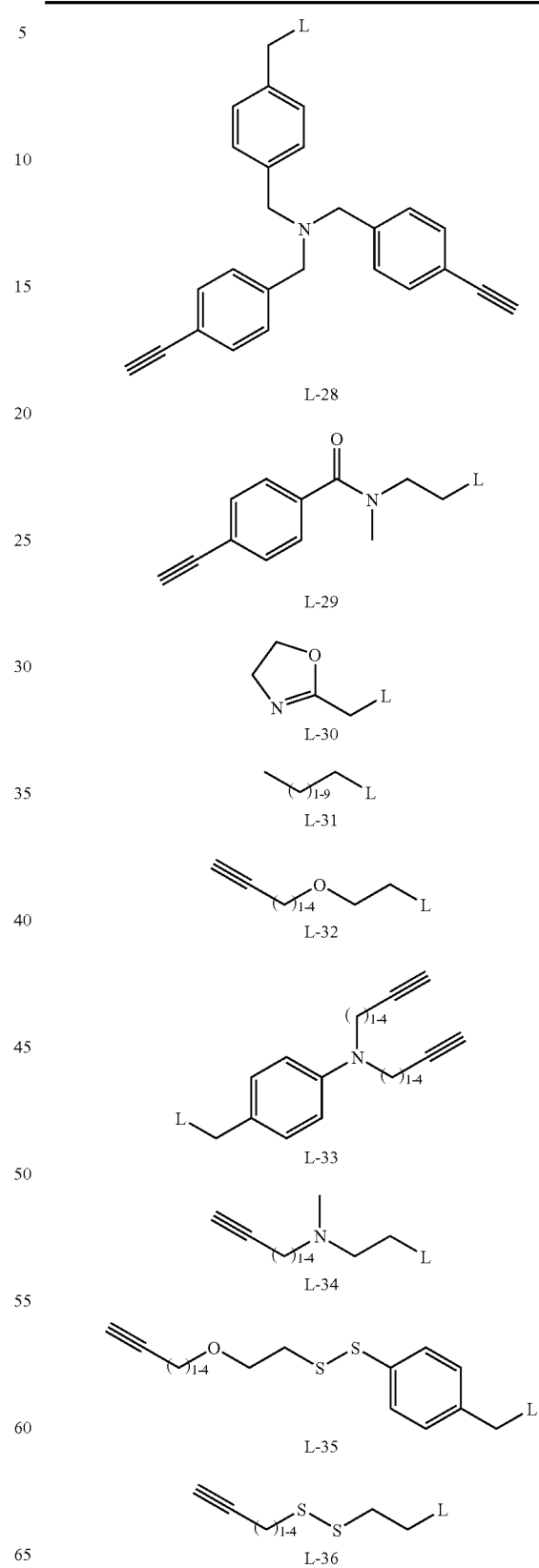

TABLE 5-continued

Representative Polymerization Terminating Agents

L-37

L-38

L-39

L-40

L-41

L-42

L-43

L-44 wherein each L is a suitable leaving group as defined above and in classes and subclasses as described above and herein.

One of ordinary skill in the art will recognize that certain of the terminating groups depicted in Tables 3, 4, and 5 comprise protected functional groups. It will be appreciated that these protecting groups are optionally removed to form compounds of the present invention. Methods for the deprotection of functional groups are well known to one of ordinary skill in the art and include those described in detail in Greene (1999).

In certain embodiments, the present invention provides a method for preparing a compound of formula I:

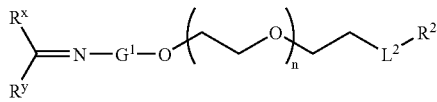

I or a salt thereof, wherein:

n is 10-2500;

$R^x$ and $R^y$ are each independently optionally substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur, or:

$R^x$ and $R^y$ are taken together to form an optionally substituted 3-8 membered saturated or partially unsaturated ring having 0-3 heteroatoms independently selected from nitrogen, oxygen, or sulfur;

$G^1$ and $L^2$ are each independently a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

each X is independently halogen;

each R is independently hydrogen or an optionally substituted aliphatic group; and $R^2$ is hydrogen, halogen, NO$_2$, CN, N$_3$, —P(O)(OR)$_2$, —P(O)(X)$_2$, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, comprising the steps of:

(a) providing a polymerization initiator of formula A:

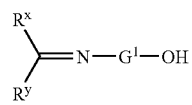

A wherein:

$R^x$ and $R^y$ are each independently optionally substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur, or:

$R^x$ and $R^y$ are taken together to form an optionally substituted 3-8 membered saturated or partially unsaturated ring having 0-3 heteroatoms independently selected from nitrogen, oxygen, or sulfur;

G¹ is a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and each R is independently hydrogen or an optionally substituted aliphatic group;

(b) polymerizing ethylene oxide onto said polymerization initiator to provide a compound of formula B:

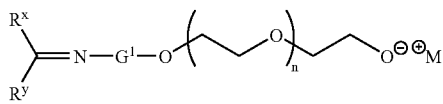

wherein:

M is the cation of a suitable metal;

n is 10-2500;

$R^x$ and $R^y$ are each independently optionally substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur, or:

$R^x$ and $R^y$ are taken together to form an optionally substituted 3-8 membered saturated or partially unsaturated ring having 0-3 heteroatoms independently selected from nitrogen, oxygen, or sulfur;

G¹ is a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and each R is independently hydrogen or an optionally substituted aliphatic group; and (c) terminating the living polymer chain-end of the compound of formula B with a suitable polymerization terminator to afford a compound of formula I.

As described generally above, the M moiety of formula B is the cation of a suitable metal capable, with its corresponding anion, of affecting the polymerization of ethylene oxide. In certain embodiments, M is $K^+$, $Cs^+$, $Na^+$, $Al^{(3+)}$, or $Y^+$. In other embodiments, M is $K^+$ or $Na^+$. According to another aspect of the present invention, M is $K^+$. In other embodiments M is a transition metal such as Sn, Pb, Zn, Cd, Cu, Pd, Mn, Cr, Mo, W, Fe, Co or organometallic complexes of these metals. In yet other embodiments, M is a rare-earth metal such as Sc, La, Pr, Nd, Sm, Eu, Gd, Dy, Yb or organometallic complexes of these metals.

According to another embodiment, the present invention provides a method for preparing a compound of formula II:

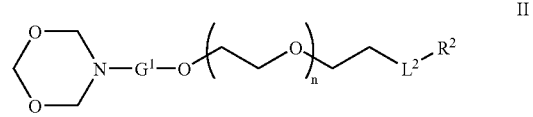

or a salt thereof, wherein:

n is 10-2500;

G¹ and $L^2$ are each independently a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^2$ is hydrogen, halogen, $NO_2$, CN, $N_3$, —P(O)(OR)$_2$, —P(O)(X)$_2$, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

each X is independently halogen; and each R is independently hydrogen or an optionally substituted aliphatic group, comprising the steps of:

(a) providing a polymerization initiator of formula C:

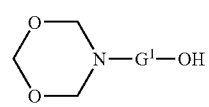

wherein G¹ is a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and each R is independently hydrogen or an optionally substituted aliphatic group;

(b) polymerizing ethylene oxide onto said polymerization initiator to provide a compound of formula D:

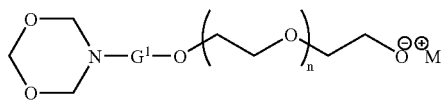

D wherein:
n is 10-2500;
M is the cation of a suitable metal;
G¹ is a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO₂—, —NRSO₂—, —SO₂NR—, —NRC(O)—, —C(O)NR—, —OC(O)NR—, or —NRC(O)O—, wherein:
  each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and
each R is independently hydrogen or an optionally substituted aliphatic group;
and
(c) terminating the living polymer chain-end of the compound of formula D with a suitable polymerization terminator to afford a compound of formula II.

As described generally above, the M moiety of formula D is the cation of a suitable metal capable, with its corresponding anion, of affecting the polymerization of ethylene oxide. In certain embodiments, M is $K^+$, $Cs^+$, $Na^+$, $Al^{(3+)}$, or $Y^+$. In other embodiments, M is $K^+$ or $Na^+$. According to another aspect of the present invention, M is $K^+$. In other embodiments M is a transition metal such as Sn, Pb, Zn, Cd, Cu, Pd, Mn, Cr, Mo, W, Fe, Co or organometallic complexes of these metals. In yet other embodiments, M is a rare-earth metal such as Sc, La, Pr, Nd, Sm, Eu, Gd, Dy, Yb or organometallic complexes of these metals.

According to another embodiment, the present invention provides a method for preparing a compound of formula III:

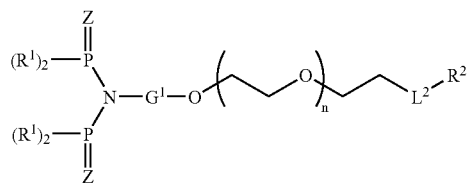

III or a salt thereof, wherein:
n is 10-2500;
each Z is independently oxygen or sulfur;
each $R^1$ is independently an optionally substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur;
$G^1$ and $L^2$ are each independently a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO₂—, —NRSO₂—, —SO₂NR—, —NRC(O)—, —C(O)NR—, —OC(O)NR—, or —NRC(O)O—, wherein:
  each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
each X is independently halogen;
each R is independently hydrogen or an optionally substituted aliphatic group; and
$R^2$ is hydrogen, halogen, $NO_2$, CN, $N_3$, —P(O)(OR)₂, —P(O)(X)₂, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
comprising the steps of:
(a) providing a polymerization initiator of formula E:

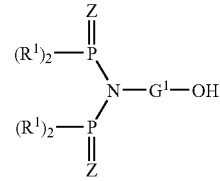

E wherein:
each Z is independently oxygen or sulfur;
$G^1$ is a valence bond or a bivalent, saturated or unsaturated, straight or branched $C_{1-12}$ hydrocarbon chain, wherein 06 methylene units of the chain are independently replaced by -Cy-, —O—, —NR—, —S—, —OC(O)—, —C(O)O—, —C(O)—, —SO—, —SO₂—, —NRSO₂—, —SO₂NR—, —NRC(O)—, —C(O)NR—, —OC(O)NR—, or —NRC(O)O—, wherein:
  each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
each R is independently hydrogen or an optionally substituted aliphatic group; and
each $R^1$ is independently an optionally substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur;
(b) polymerizing ethylene oxide onto said polymerization initiator to provide a compound of formula F:

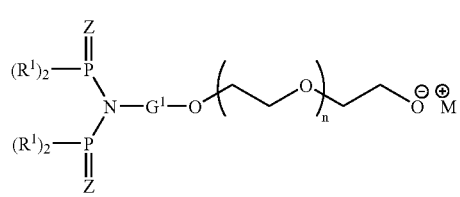

F wherein:
M is the cation of a suitable metal;
n is 10-2500;
each Z is independently oxygen or sulfur;

$G^1$ is a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

each R is independently hydrogen or an optionally substituted aliphatic group; and each $R^1$ is independently an optionally substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur; and (c) terminating the living polymer chain-end of the compound of formula F with a suitable polymerization terminator to afford a compound of formula III.

As described generally above, the M moiety of formula F is the cation of a suitable metal capable, with its corresponding anion, of affecting the polymerization of ethylene oxide. In certain embodiments, M is $K^+$, $Cs^+$, $Na^+$, $Al^{(3+)}$, or $Y^+$. In other embodiments, M is $K^+$ or $Na^+$. According to another aspect of the present invention, M is $K^+$. In other embodiments M is a transition metal such as Sn, Pb, Zn, Cd, Cu, Pd, Mn, Cr, Mo, W, Fe, Co or organometallic complexes of these metals. In yet other embodiments, M is a rare-earth metal such as Sc, La, Pr, Nd, Sm, Eu, Gd, Dy, Yb or organometallic complexes of these metals.

According to another embodiment, the present invention provides a method for preparing a compound of formula IV:

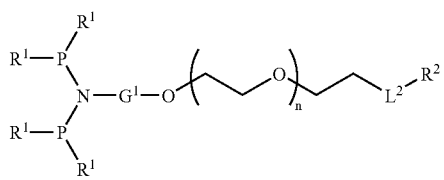

IV or a salt thereof, wherein:
n is 10-2500;
each $R^1$ is independently an optionally substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur;

$G^1$ and $L^2$ are each independently a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

each X is independently halogen;
each R is independently hydrogen or an optionally substituted aliphatic group; and $R^2$ is hydrogen, halogen, $NO_2$, CN, $N_3$, —P(O)(OR)$_2$, —P(O)(X)$_2$, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

comprising the steps of:
(a) providing a polymerization initiator of formula G:

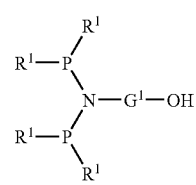

G wherein $G^1$ is a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

each R is independently hydrogen or an optionally substituted aliphatic group; and each $R^1$ is independently an optionally substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur;

(b) polymerizing ethylene oxide onto said polymerization initiator to provide a compound of formula H:

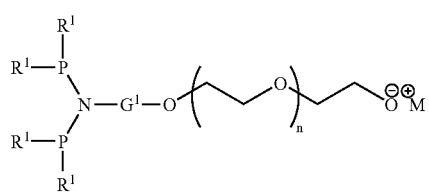

H wherein:
M is the cation of a suitable metal;
n is 10-2500;

G¹ is a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

each R is independently hydrogen or an optionally substituted aliphatic group; and each R¹ is independently an optionally substituted aliphatic, an optionally substituted 3-8 membered saturated, partially unsaturated, or aryl ring having 0-4 heteroatoms independently selected from nitrogen, oxygen, or sulfur, or an optionally substituted 8-10 membered saturated, partially unsaturated, or aryl bicyclic ring having 0-5 heteroatoms independently selected from nitrogen, oxygen, or sulfur; and (c) terminating the living polymer chain-end of the compound of formula H with a suitable polymerization terminator to afford a compound of formula IV.

As described generally above, the M moiety of formula H is the cation of a suitable metal capable, with its corresponding anion, of affecting the polymerization of ethylene oxide. In certain embodiments, M is $K^+$, $Cs^+$, $Na^+$, $Al^{(3+)}$, or $Y^+$. In other embodiments, M is $K^+$ or $Na^+$. According to another aspect of the present invention, M is $K^+$. In other embodiments M is a transition metal such as Sn, Pb, Zn, Cd, Cu, Pd, Mn, Cr, Mo, W, Fe, Co or organometallic complexes of these metals. In yet other embodiments, M is a rare-earth metal such as Sc, La, Pr, Nd, Sm, Eu, Gd, Dy, Yb or organometallic complexes of these metals.

Although certain exemplary embodiments are depicted and described above and herein, it will be appreciated that compounds of the invention can be prepared according to the methods described generally above using appropriate starting materials by methods generally available to one of ordinary skill in the art. Additional embodiments are exemplified in more detail herein.

5. Uses, Methods, and Compositions

As discussed above, the present invention provides bifunctional PEG's, intermediates thereto, and methods of preparing the same. Such functionalized PEG's are useful for a variety of purposes in the pharmaceutical and biomedical fields. Such uses include using the bifunctional PEG's of the present invention in the process of PEGylating (i.e. conjugating to) other molecules.

In certain embodiments, a compound of formula V or V-a is useful for conjugation as described hereinbelow. In other embodiments, a compound of any of formulae I, II, III, and IV are conjugated via the -L²-R² end. Such conjugation products are then optionally deprotected to provide a compound of formula V or V-a that is conjugated at the -L²-R² end. Methods of conjugation, and substrates suitable for conjugation, are well known in the art and include those described herein.

For example, U.S. Pat. No. 6,797,257 describes imaging agents prepared by PEGylating gadolinium oxide albumin microspheres. U.S. Pat. Nos. 6,790,823 and 6,764,853 describe the PEGylation of proteins by covalently bonding through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecule(s).

Another aspect of the invention provides a method of PEGylating a primary or secondary label, a dye, or another detectable moiety for biosensors, bioassays, biorecognition, detection, proteomics, genomics, microarray, and other molecular biological applications. Such PEGylation may be carried out by covalent linking of one PEG functionality to the detectable moiety or through coordination of a PEG functionality (e.g. thiol, amine, alcohol, carboxylic acid) to the detectable moiety. The opposite PEG end group can be further linked to targeting groups, permeation enhancers, proteins, sugars, DNA, RNA, cells, viruses, or other biomolecules for targeted delivery or recognition. Such labels or detectable moieties include but are not limited to organic and inorganic dyes, semiconducting nanoparticles (e.g. CdSe, CdS, CdSe/ZnS, ZnSe, PbSe nanoparticles), magnetic nanoparticles (e.g. Co, FePt, $Fe_3O_4$, $Fe_2O_3$ nanoparticles), or other metal nanoparticles (e.g. Au nanoparticles). For representative examples of nanoparticle PEGylation see Takae, S.; Akiyama, Y.; Otsuka, H.; Nakamura, T.; Nagasaki, Y.; Kataoka, K. "Ligand density effect on biorecognition by PEGylated gold nanoparticles: regulated interaction of RCA120 lectin with lactose installed to the distal end of tethered PEG strands on gold surface" *Biomacromolecules* 2005, 6, 818-824; Ishii, T.; Sunaga, Y.; Otsuka, H.; Nagasaki, Y.; Kataoka, K. "Preparation of water soluble CdS quantum dots stabilized by functional poly(ethylene glycol) and its application for bioassay" *J. Photopolym. Sci. Technol.* 2004, 17, 95-98; Otsuka, H.; Akiyama, Y.; Nagasaki, Y.; Kataoka, K. "Quantitative and Reversible Lectin-Induced Association of Gold Nanoparticles Modified with α-Lactosyl-ω-mercapto-poly(ethylene glycol)" *J. Am. Chem. Soc.* 2001, 123, 8226-8230; Akerman, M. E.; Chan, W. C. W.; Laakkonen, P.; Bhatia, S, N.; Ruoslahti, E. R. "Nanocrystal targeting in vivo" *P. Natl. Acad. Sci. USA* 2002, 99, 12617-12621; Skaff, H.; Enrick, T. "A Rapid Route to Amphiphilic Cadmium Selenide Nanoparticles Functionalized with Poly(ethylene glycol)" *Chem. Comm.*, 2003, 1, 52-53.

Accordingly, another aspect of the present invention provides a method of PEGylating a biomolecule with a compound of the present invention as described generally above and in classes and subclasses defined above and herein. In certain embodiments, the present invention provides a method of PEGylating a therapeutic or a therapeutic carrier such as a protein, a cell, a virus particle, a plasmid, an oligopeptide, an oligonucleotide (e.g. siRNA, miRNA, aptamer), small molecule drug, a liposome, a polymersome, a polymer microsphere, or a lipid emulsion with a compound of the present invention as described generally above and in classes and subclasses defined above and herein. According to another aspect, the present invention provides a method for PEGylating a substrate. Such PEGylation may be carried out by covalent linking of a terminal PEG functionality to the substrate or using any number of bioconjugation techniques.

The bifunctional PEG's of the present invention are also useful for linking two biomolecules together wherein said biomolecules are the same or different from each other. For example, one terminus of the present compounds may be linked to a surface, another polymer, therapeutic, therapeutic carrier, protein, cell, virus particle, a plasmid, oligopeptide, oligonucleotide (e.g. siRNA, miRNA, aptamer), small molecule drug, liposome, polymersome, polymer microsphere, lipid emulsion, or a detectable moiety and the other terminus of the present compounds may be linked to a surface, targeting group, permeation enhancer, growth factor, protein, sugar, DNA, RNA, cell, virus, diagnostic agent, or a detectable moiety. Accordingly, the present invention also provides a method for linking two biomolecules together wherein said method comprises coupling one terminus of a compound of the present invention to a first biomolecule then coupling the other terminus of a compound of the present invention to a second molecule, wherein the first and second biomolecules may be the same or different from each other.

Accordingly, one aspect of the present invention provides a method of PEGylating a protein therapeutic with a compound of the present invention as described generally above and in classes and subclasses defined above and herein. Such PEGylation may be carried out by covalent linking of one PEG functionality to the protein using any number of bioconjugation techniques. The opposite PEG end group can be further linked to targeting groups, permeation enhancers, proteins, sugars, DNA, RNA, cells, viruses, dyes, detectable moieties, labels or other biomolecules for targeted delivery, biorecognition, or detection. For representative examples of PEGylating a protein see Harris, J. M.; Chess, R. B. "Effect of PEGylation on Pharmaceuticals" *Nat. Rev. Drug. Discov.* 2003, 2, 214-221; Kozlowski, A.; Harris, J. M. "Improvements in protein PEGylation: pegylated interferons for treatment of hepatitis C" *J. Control. Release* 2001, 72, 217-224; Koslowski, A.; Charles, S. A.; Harris, J. M. "Development of pegylated interferons for the treatment of chronic hepatitis C" *Biodrugs* 2001, 15, 419-429; Harris, J. M.; Martin, N. E.; Modi, M. "Pegylation: a novel process for modifying pharmacokinetics" *Clin. Pharmacokinet.* 2001, 40, 539-551; Roberts, M. J.; Bentley, M. D.; Harris, J. M. "Chemistry for peptide and protein PEGylation" *Adv. Drug Deliver. Rev.* 2002, 54, 459-476.

Another aspect of the present invention provides a method of PEGylating a small molecule drug with a compound of the present invention as described generally above and in classes and subclasses defined above and herein. Such PEGylation may be carried out by covalent linking of one PEG functionality to the small molecule drug using any number of bioconjugation techniques. The opposite PEG end group can be further linked to targeting groups, permeation enhancers, proteins, sugars, DNA, RNA, cells, viruses, dyes, detectable moieties, labels or other biomolecules for targeted delivery, biorecognition, or detection. For representative examples of PEGylating a small molecule drug see Greenwald, R. B. "PEG drugs: an overview" *J. Control. Release* 2001, 74, 159-171; Caliceti, P.; Monfardini, C.; Sartore, L.; Schiavon, O.; Baccichetti, F.; Carlassare, F.; Veronese, F. M. "Preparation and properties of monomethoxy poly(ethylene glycol) doxorubicin conjugates linked by an amino acid or a peptide as spacer" *Il Farmaco* 1993, 48, 919-932; Fleming, A. B.; Haverstick, K.; Saltzman, W. M. "In vitro cytotoxicity and in vivo distribution after direct delivery of PEG-camptothecin conjugates to the rat brain" *Bioconjug Chem.* 2004, 15, 1364-1375.

Yet another aspect of the present invention provides a drug-polymer conjugate comprising a compound of the present invention and a pharmaceutically active agent. In still another aspect of the present invention, pharmaceutically acceptable compositions are provided, wherein these compositions comprise a drug-polymer conjugate as described herein, and optionally comprise a pharmaceutically acceptable carrier, adjuvant or vehicle. In certain embodiments, these compositions optionally further comprise one or more additional therapeutic agents.

One of ordinary skill in the art would recognize that the present compounds are useful for the PEGylation of small molecule drugs. Small molecule drugs suitable for PEGylation with the present compounds include, but are not limited to, those having a functional group suitable for covalently linking to the bifunctional PEG's of the present invention. Such drugs include, without limitation, chemotherapeutic agents or other anti-proliferative agents including alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), angiogenesis inhibitors (Avastin) and hormones (Tamoxifen, Leuprolide, Flutamide, and Megestrol), Gleevec, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of small molecule drugs that may be PEGylated with the compounds of this invention include treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Another aspect of the present invention provides a method of PEGylating a virus with a compound of the present invention as described generally above and in classes and subclasses defined above and herein. Such PEGylation may be carried out by covalent linking of one PEG functionality to the virus using any number of bioconjugation techniques. The opposite PEG end group can be, after deprotection, further linked to targeting groups, permeation enhancers, proteins, sugars, DNA, RNA, cells, viruses, dyes, detectable moieties, labels or other biomolecules for targeted delivery, biorecognition, or detection. For representative examples of virus PEGylation see Gupta, S. S.; Kuzelka, J.; Singh, P.; Lewis, W. G.; Manchester, M.; Finn, M. G. "Accelerated Bioorthogonal Conjugation: A Practical Method for the Ligation of Diverse Functional Molecules to a Polyvalent Virus Scaffold" *Bioconjug. Chem.* 2005, 16, 1572-1579; Raja, K. S.; Wang, Q.; Gonzalez, M. J.; Manchester, M.; Johnson, J. E.; Finn, M. G. "Hybrid Virus-Polymer Materials. 1. Synthesis and Properties of PEG-Decorated Cowpea Mosaic Virus" *Biomacromolecules* 2003, 4, 472-476; Oh, I. K.; Mok, H.; Park, T. G. "Folate Immobilized and PEGylated Adenovirus for Retargeting to Tumor Cells" *Bioconjugate Chem.* ASAP Article (Published online Apr. 14, 2006)

Yet another aspect of the present invention provides a method of PEGylating therapeutic carriers such as liposomes, polymersomes, microspheres, capsules, or lipid emulsions with a compound of the present invention as described generally above and in classes and subclasses defined above and herein. Such PEGylation may be carried out by covalent linking of one PEG functionality to the therapeutic carrier using any number of bioconjugation techniques or by the non-covalent incorporation of a PEGylated molecule (e.g. lipid, phospholipid, or polymer) into the carrier. The opposite PEG end group can be further linked to targeting groups, permeation enhancers, proteins, sugars, DNA, RNA, cells, viruses, dyes, detectable moieties, labels or other biomolecules for targeted delivery, biorecognition, or detection. For representative examples of PEGylating therapeutic carriers see Lukyanov, A. N.; Elbayoumi, T. A.; Chakilam, A. R.; Torchilin, V. P. "Tumor-targeted liposomes: doxorubicin-loaded long-circulating liposomes modified with anti-cancer antibody" *J. Control. Release* 2004, 100, 135-144; Forssen, E.; Willis, M. "Ligand-targeted liposomes" *Adv. Drug Del. Rev.* 1998, 29, 249-271; Koning, G. A.; Schiffelers, R. M.; Wauben, M. H. M.; Kok, R. J.; Mastrobattista, E.; Molema, G.; ten Hagen, T. L. M.; Storn, G. "Targeting of Angiogenic Endothelial Cells at Sites of Inflammation by Dexamethasone Phosphate-Containing RGD Peptide Liposomes Inhibits Experimental Arthritis" *Arthritis Rheum.* 2006, 54, 1198-1208; Torchilin, V. P. "Structure and design of polymeric surfactant-based drug delivery systems" *J. Control. Release* 2001, 73, 137-172.

Another aspect of the present invention provides a method of PEGylating a cell with a compound of the present invention as described generally above and in classes and subclasses defined above and herein. Such PEGylation may be carried out by covalent linking of one PEG functionality to the cell using any number of bioconjugation techniques. The opposite PEG end group can be further linked to targeting groups, permeation enhancers, proteins, sugars, DNA, RNA, cells, viruses, dyes, detectable moieties, labels or other biomolecules for targeted delivery, biorecognition, or detection. See Scott, M. D.; Chen, A. M. "Beyond the red cell: pegylation of other blood cells and tissues" *Transfus. Clin. Biol.* 2004, 11, 40-46.

Another aspect of the present invention provides a method of PEGylating the surface of a natural or synthetic material or biomaterial with a compound of the present invention as described generally above and in classes and subclasses defined above and herein. Such PEGylation may be carried out by covalent linking of one PEG functionality to the surface using any number of bioconjugation techniques or through non-covalent interactions with PEG or the PEG end-groups. Such surface PEGylation generally enhances anti-fouling properties of the material and can reduce the foreign-body response of injectable or implantable biomaterials. For representative examples of Bergstrom, K.; Holmberg, K.; Safranj, A.; Hoffman, A. S.; Edgell, M. J.; Kozlowski, A.; Hovanes, B. A.; Harris, J. M. "Reduction of fibrinogen adsorption on PEG-coated polystyrene surfaces" *J. Biomed Mater. Res.* 1992, 26, 779-790; Vladkova, T.; Krasteva, N.; Kostadinova, A.; Altankov, G. "Preparation of PEG-coated surfaces and a study for their interaction with living cells" *J. Biomater. Sci. Polym. Ed.* 1999, 10, 609-620.

Another aspect of the present invention provides a method of linking molecules or biomolecules to a synthetic or natural surface with a compound of the present invention as described generally above and in classes and subclasses defined above and herein. Such PEGylation may be carried out by covalent linking of one PEG functionality to the surface using any number of bioconjugation techniques or through non-covalent interactions with PEG or the PEG end-groups. The opposite PEG end group can be further linked to proteins, sugars, DNA, RNA, cells, viruses, dyes, detectable moieties, labels or other biomolecules for biorecognition and/or detection. For representatives examples of using PEGylated surface linkers see Otsuka, H.; Nagasaki, Y.; Kataoka, K. "Characterization of aldehyde-PEG tethered surfaces: influence of PEG chain length on the specific biorecognition" *Langmuir* 2004, 20, 11285-11287; Muñoz, E. M.; Yu, H.; Hallock, J.; Edens, R. E.; Linhardt, R. J. "Poly(ethylene glycol)-based biosensor chip to study heparin-protein interactions" *Anal. Biochem.* 2005, 343, 176-178; Metzger, S. W.; Natesan, M.; Yanavich, C.; Schneider, J.; Leea, G. U. "Development and characterization of surface chemistries for microfabricated biosensors" *J. Vac. Sci. Technol. A* 1999, 17, 2623-2628; Hahn, M. S.; Taite, L. J.; Moon, J. J.; Rowland, M. C.; Ruffino, K. A.; West, J. L. "Photolithographic patterning of polyethylene glycol hydrogels" *Biomaterials* 2006, 27, 2519-2524; Veiseh, M.; Zareie, M. H.; Zhang, M. "Highly Selective Protein Patterning on Gold-Silicon Substrates for Biosensor Applications" *Langmuir*, 2002, 18, 6671-6678.

Another aspect of the present invention provides a method of incorporating PEG into a hydrogel with a compound of the present invention as described generally above and in classes and subclasses defined above and herein. Such PEGylation may be carried out by the reaction of one PEG functionality for incorporation into the hydrogel matrix or through non-covalent interaction of the hydrogel and PEG or the PEG end-groups. The opposite PEG end group can be further linked to proteins, growth factors, antibodies, oligopeptides, sugars, DNA, RNA, cells, viruses, dyes, detectable moieties, labels or other biomolecules to promote cell adhesion and growth, for biorecognition, or detection. For examples of producing hydrogels from functional PEGs see Kim, P.; Kim, D. H.; Kim, B.; Choi, S. K.; Lee, S. H.; Khademhosseini, A.; Langer, R.; Suh, K. Y. "Fabrication of nanostructures of polyethylene glycol for applications to protein adsorption and cell adhesion" *Nanotechnology*, 2005, 16, 2420-2426; Raeber, G. P.; Lutolf, M. P; Hubbell, J. A. "Molecularly Engineered PEG Hydrogels: A Novel Model System for Proteolytically Mediated Cell Migration" *Biophys. J.* 2005, 89, 1374-1388; Quick, D. J.; Anseth, K. S. "DNA delivery from photocrosslinked PEG hydrogels: encapsulation efficiency, release profiles, and DNA quality" *J. Control. Release* 2004, 96, 341-351.

Another aspect of the present invention provides a method of producing block and graft copolymers of PEG using a compound of the present invention as described generally above and in classes and subclasses defined above and herein. A compound of the present invention which possess appropriate reactive functionality may serve as macroinitiators of cyclic esters (e.g. caprolactone, lactide, glycolide), cyclic ethers, cyclic phosphazenes, N-carboxyanhydrides (NCAs), or vinyl monomers (e.g. N-isopropylacrylamide, methyl acrylate, styrene) to synthesize block copolymers for use as micellar therapeutic carriers. One or both PEG functionalities can be used to initiate or mediate the growth of additional polymer blocks. In cases where a single PEG functionality serves as an initiator, the opposite PEG end group can be further linked to targeting groups, permeation enhancers, proteins, sugars, DNA, RNA, cells, viruses, dyes, detectable moieties, labels or other biomolecules for targeted delivery, biorecognition, or detection. For representative examples of PEG macroinitiators see Akiyama, Y.; Harada, A.; Nagasaki, Y.; Kataoka, K. *Macromolecules* 2000, 33, 5841-5845; Yamamoto, Y.; Nagasaki, Y.; Kato, Y.; Sugiyama, Y.; Kataoka, K. "Long-circulating poly(ethylene glycol)-poly(D,L-lactide) block copolymer micelles with modulated surface charge" *J. Control. Release* 2001, 77, 27-38; Bae, Y.; Jang, W. D.; Nishiyama, N.; Fukushima, S.; Kataoka, K. "Multifunctional polymeric micelles with folate-mediated cancer cell targeting and pH-triggered drug releasing properties for active intracellular drug delivery" *Mol. Biosyst.* 2002, 1, 242-250; Nasongkla, N.; Shuai, X.; Ai, H.; Weinberg, B. D.; Pink, J.;

Boothman, D. A.; Gao, J. "cRGD-Functionalized Polymer Micelles for Targeted Doxorubicin Delivery" Angew. *Chem. Int. Ed.* 2004, 43, 6323-6327.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compounds and compositions, according to the method of the present invention, may be administered using any amount and any route of administration effective for treating or lessening the severity of the disorder being treated. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

EXAMPLES

As depicted in the Examples below, in certain exemplary embodiments, compounds are prepared according to the following general procedures. It will be appreciated that, although the general methods depict the synthesis of certain compounds of the present invention, the following general methods, in addition to the Schemes set forth above and other methods known to one of ordinary skill in the art, can be applied to all compounds and subclasses and species of each of these compounds, as described herein.

Example 1

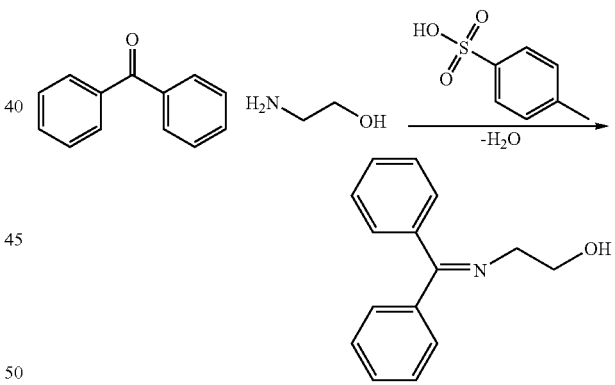

Benzophenone-imine-ethanol: To a 500 mL round bottom flask equipped with stirbar, Dean-Stark apparatus, reflux condenser, and $N_2$ inlet was added benzophenone (45.5 g, 0.25 mol), ethanol amine (23 mL, 0.38 mol), p-toluenesulfonic acid (4.3 g, 0.025 mol), and toluene (300 mL). The reaction stirred at reflux for 16 hours, collecting 8 mL water. The solution was cooled and the solution washed with $NaHCO_3$ (aq) (2×400 mL). The aqueous layer was extracted with ether (2×300 mL) and the combined organic layers dried over $MgSO_4$, stirred with carbon black for 1 hour, then filtered. The solvent was evaporated and the residue dissolved in ether (300 mL). Hexanes (900 mL) was added and the product crystallized over 2 hours at room temperature. The solid was filtered and recrystallized from 3:1 hexanes:ether giving 25.2 g of colorless needles (0.112 mol, 45%). HPLC (3:1 acetonitrile:water, $C_8$ column) 99.9+% pure.

Example 2

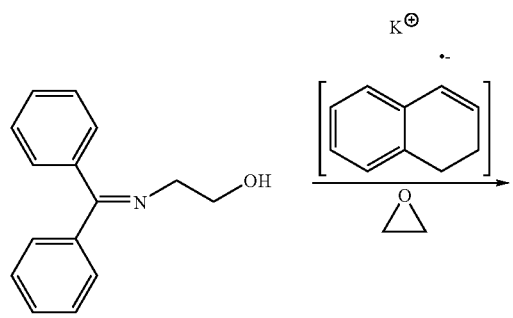

Benzophenone-imine-PEG-alcohol: To a stirred solution of benzophenone-imine-ethanol (0.45 g, 2 mmol) in anhydrous THF (200 mL) was added a solution of potassium naphthalenide in THF (0.2 M, 10 mL, 2 mmol). The resulting solution was cooled to 0° C., then ethylene oxide (10 g, 227 mmol) was introduced to the alkoxide solution using Schlenk techniques. Upon complete addition of the ethylene oxide, the flask was backfilled with Argon, sealed and stirred at 40° C. After 24 h, the reaction was quenched with methanol and the solvent evaporated. The resulting viscous liquid was then precipitated into cold diethyl ether to give a powder. $^1$H NMR (400 MHz, DMSO-$d_6$, δ) 7.41, 7.29, 7.19, 4.56, 3.7-3.3. GPC (DMF, MALS) $M_n$=5,400; PDI=1.06.

Example 3

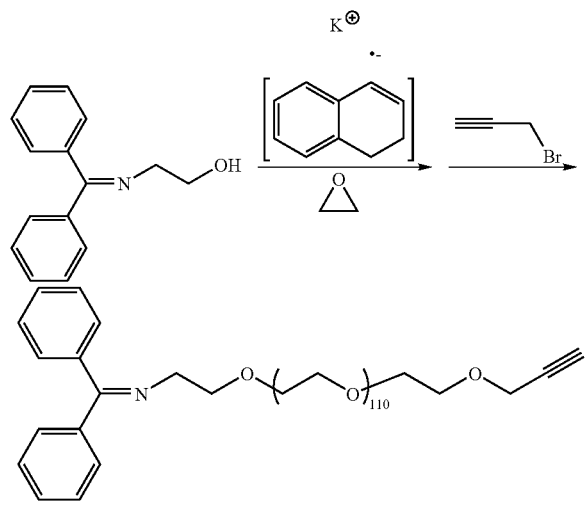

Benzophenone-imine-PEG-propyne: To a stirred solution of benzophenone-imine-ethanol (0.45 g, 2 mmol) in anhydrous THF (200 μL) was added a solution of potassium naphthalenide in THF (0.2 M, 10 mL, 2 mmol). The resulting solution was cooled to 0° C., then ethylene oxide (20 g, 454 mmol) was introduced to the alkoxide solution using Schlenk techniques. Upon complete addition of the ethylene oxide, the flask was backfilled with Argon, sealed and stirred at 40° C. After 24 h, propargyl bromide (1.3 g, 10 mmol) was added to the reaction using Schlenk techniques. The solution was stirred for and additional 12 h at 40° C., allowed to cool, and the solvent removed. The resulting viscous liquid was precipitated into cold diethyl ether to give a powder. $^1$H NMR (400 MHz, DMSO-$d_6$, δ) 7.42, 7.29, 7.19, 4.14, 3.7-3.3. GPC (DMF, MALS) $M_n$=11,400; PDI=1.02.

Example 4

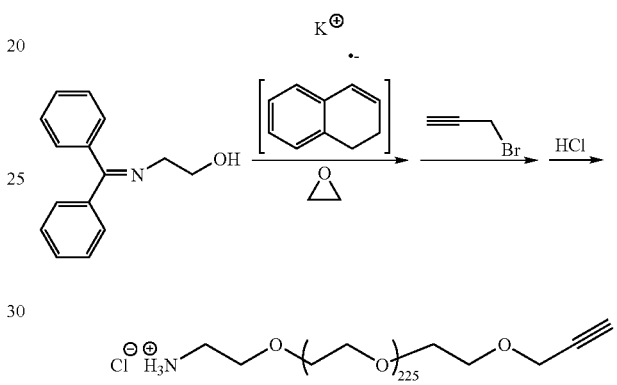

Ammonium hydrochloride-PEG-propyne: To a stirred solution of benzophenone-imine-ethanol (0.45 g, 2 mmol) in anhydrous THF (200 mL) was added a solution of potassium naphthalenide in THF (0.2 M, 10 μL, 2 mmol). The resulting solution was cooled to 0° C., then ethylene oxide (20 g, 454 mmol) was introduced to the alkoxide solution using Schlenk techniques. Upon complete addition of the ethylene oxide, the flask was backfilled with Argon, sealed and stirred at 40° C. After 24 h, propargyl bromide (1.3 g, 10 mmol) was added to the reaction using Schlenk techniques. The solution was stirred for and additional 12 h at 40° C., allowed to cool, and the solvent removed. The resulting viscous liquid was dissolved in 6 N HCl (150 mL) and stirred for 3 h. The solution was extracted with CHCl$_3$ (4×300 mL) then the combined organic layers dried over MgSO$_4$, filtered and the solvent evaporated. The resulting viscous liquid was precipitated into cold diethyl ether to give a white powder. $^1$H NMR (400 MHz, DMSO-$d_6$, δ) 8.9, 4.14, 3.7-3.3. GPC (DMF, MALS) $M_n$=11,600; PDI=1.03.

Example 5

It will be appreciated that compounds of the present invention are prepared according to the methods of the invention, the schemes depicted herein, Examples 1-4 above, and by methods known to one of ordinary skill in the art. Exemplary non-limiting compounds that are prepared according to the present invention are set forth below as Examples 5a through 5j. In each of Examples 5a through 5j, "DIAD" refers to diisopropylazodicarboxylate and "TPP" refers to triphenylphosphine.

Example 5a
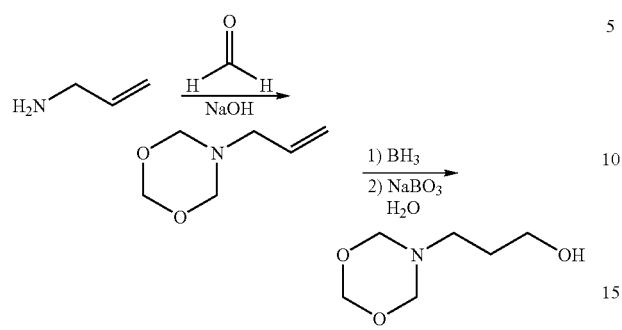
Example 5b
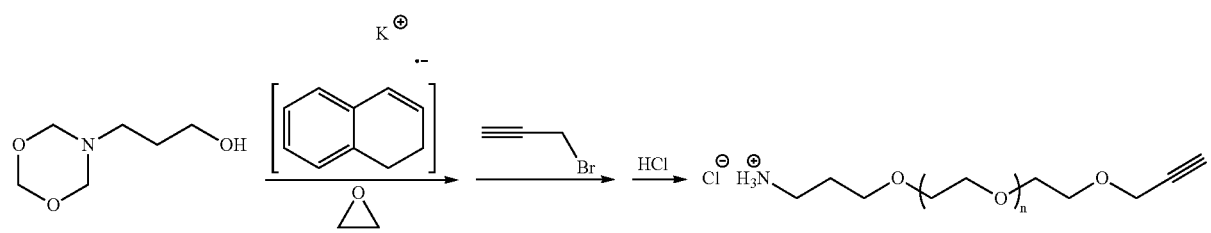
Example 5c
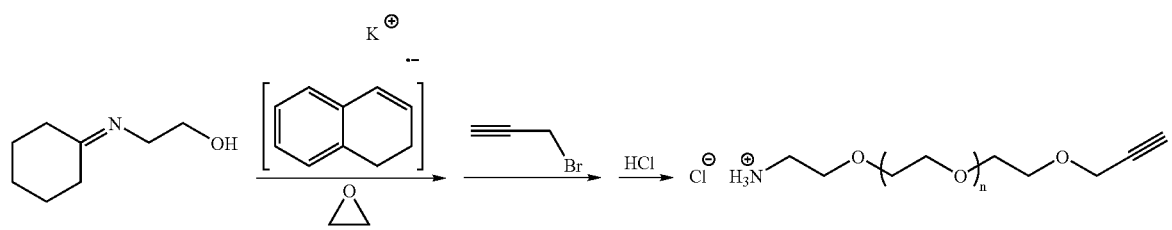
Example 5d
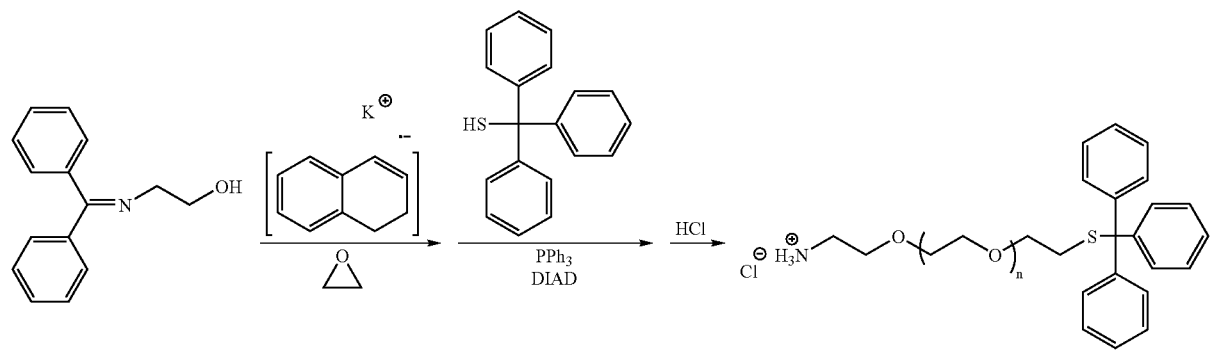

Example 5e
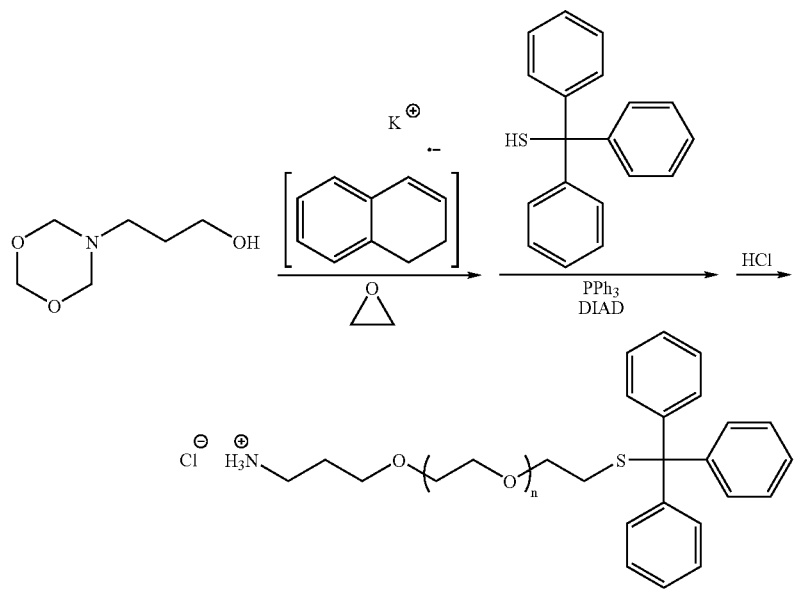
Example 5f
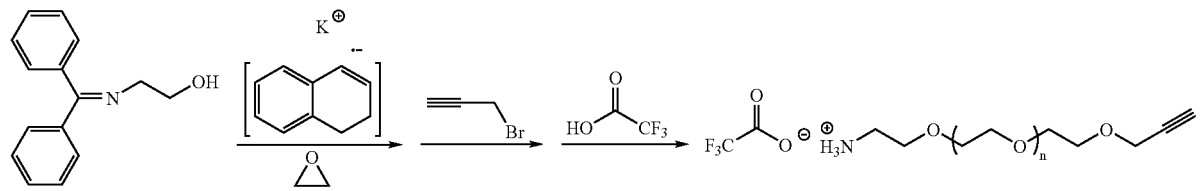
Example 5g
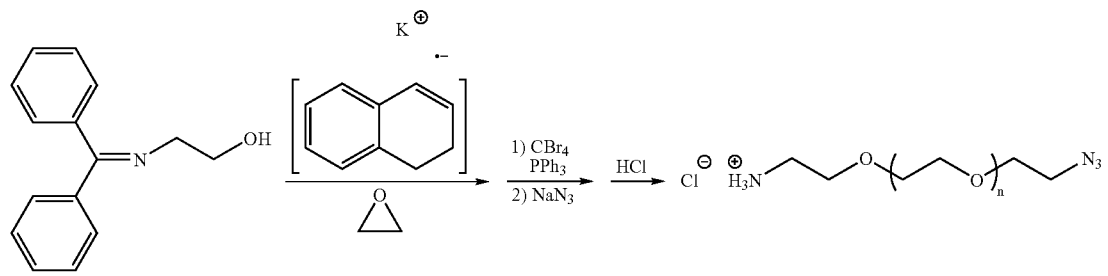
Example 5h
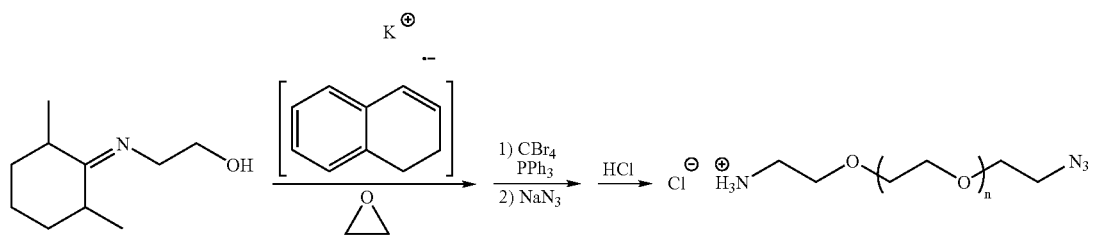

Example 5i

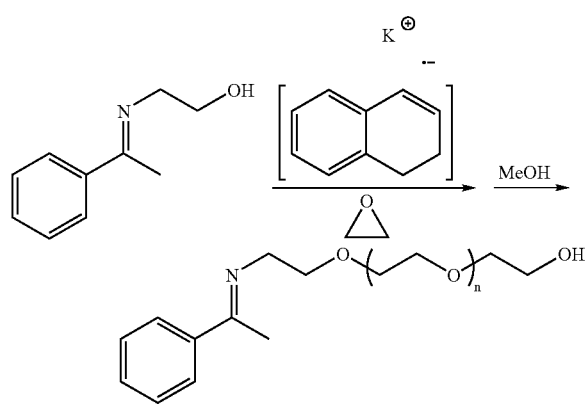

Example 5j

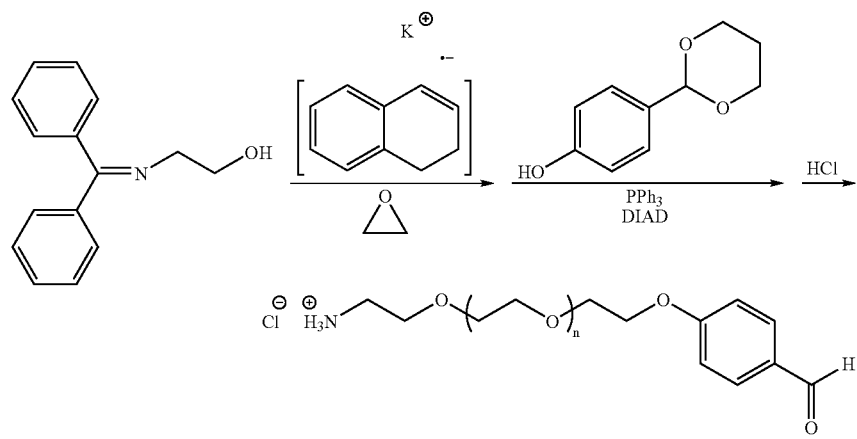

Benzophenone-imine-ethanol

To a 500 mL round bottom flask equipped with stirbar, Dean-Stark apparatus, reflux condenser, and $N_2$ inlet was added benzophenone (45.5 g, 0.25 mol), ethanol amine (23 mL, 0.38 mol), p-toluenesulfonic acid (4.3 g, 0.025 mol), and toluene (300 mL). The reaction stirred at reflux for 16 hours, collecting 8 mL water. The solution was cooled and the solution washed with $NaHCO_{3(aq)}$ (2×400 mL). The aqueous layer was extracted with ether (2×300 mL) and the combined organic layers dried over $MgSO_4$, stirred with carbon black for 1 hour, then filtered. The solvent was evaporated and the residue dissolved in ether (300 mL). Hexanes (900 mL) was added and the product crystallized over 2 hours at room temperature. The solid was filtered and recrystallized from 3:1 hexanes:ether giving 25.2 g of colorless needles (0.112 mol, 45%). HPLC (3:1 acetonitrile:water, $C_8$ column) 99.9+% pure.

Example 6 | Example 7

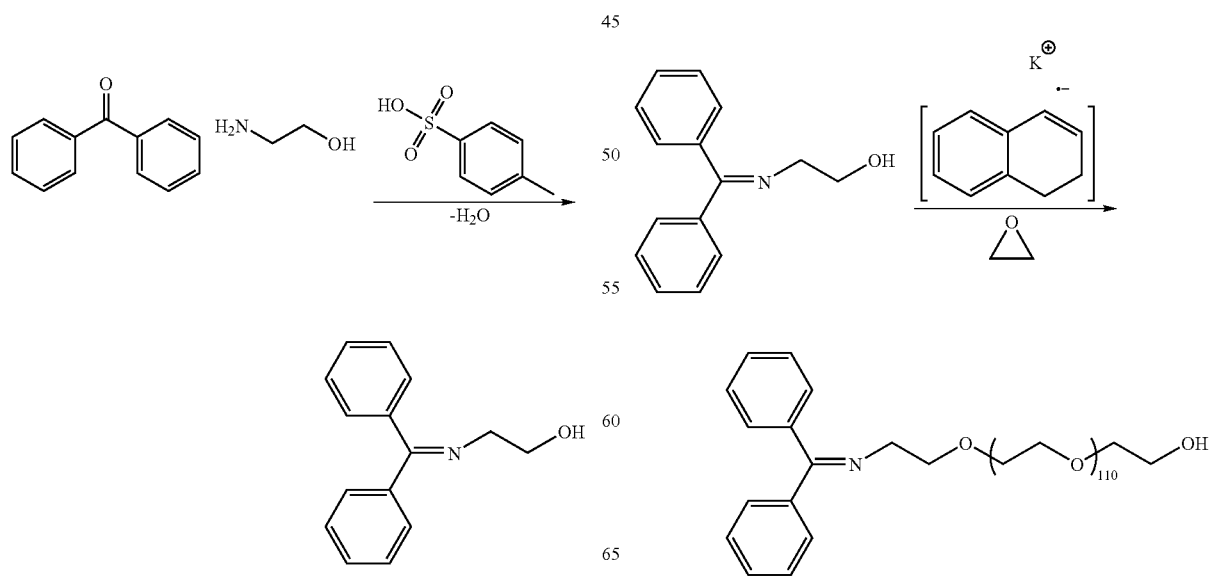

Benzophenone-imine-PEG-alcohol

To a stirred solution of benzophenone-imine-ethanol (0.45 g, 2 mmol) in anhydrous THF (200 mL) was added a solution of potassium naphthalenide in THF (0.2 M, 10 mL, 2 mmol). The resulting solution was cooled to 0° C., then ethylene oxide (10 g, 227 mmol) was introduced to the alkoxide solution using Schlenk techniques. Upon complete addition of the ethylene oxide, the flask was backfilled with Argon, sealed and stirred at 40° C. After 24 h, the reaction was quenched with methanol and the solvent evaporated. The resulting viscous liquid was then precipitated into cold diethyl ether to give a powder. $^1$H NMR (400 MHz, DMSO-d$_6$, δ) 7.41, 7.29, 7.19, 4.56, 3.7-3.3. GPC (DMF, MALS) $M_n$=5,400; PDI=1.06.

Example 8

Benzophenone-imine-PEG-azide

To a stirred solution of benzophenone-imine-ethanol (0.45 g, 2 mmol) in anhydrous THF (200 mL) was added a solution of potassium naphthalenide in THF (0.2 M, 10 mL, 2 mmol). The resulting solution was cooled to 0° C., then ethylene oxide (20 g, 454 mmol) was introduced to the alkoxide solution using Schlenk techniques. Upon complete addition of the ethylene oxide, the flask was backfilled with Argon, sealed and stirred at 40° C. The solution was cooled to room temperature then triethylamine (0.72 g, 10 mmol) and mesyl

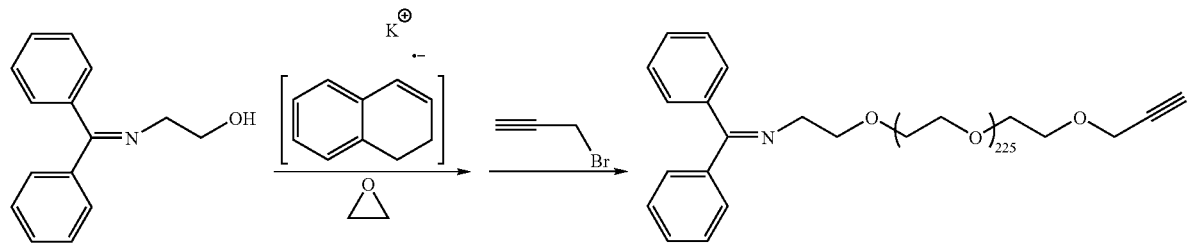

Benzophenone-imine-PEG-propyne

To a stirred solution of benzophenone-imine-ethanol (0.45 g, 2 mmol) in anhydrous THF (200 mL) was added a solution of potassium naphthalenide in THF (0.2 M, 10 mL, 2 mmol). The resulting solution was cooled to 0° C., then ethylene oxide (20 g, 454 mmol) was introduced to the alkoxide solution using Schlenk techniques. Upon complete addition of the ethylene oxide, the flask was backfilled with Argon, sealed and stirred at 40° C. After 24 h, propargyl bromide (1.3 g, 10 mmol) was added to the reaction using Schlenk techniques. The solution was stirred for and additional 12 h at 40° C., allowed to cool, and the solvent removed. The resulting viscous liquid was precipitated into cold diethyl ether to give a powder. $^1$H NMR (400 MHz, DMSO-d$_6$, δ) 7.42, 7.29, 7.19, 4.14, 3.7-3.3. GPC (DMF, MALS) $M_n$=11,400; PDI=1.02.

Example 9 chloride (1.14 g, 10 mmol) was added dropwise via syringe and the solution stirred at room temperature for 12 hours, then the solvent removed. The resulting viscous liquid was dissolved in ethanol (~200 mL) then NaN$_3$ (0.65 g, 10 mmol) was added. The solution was stirred at reflux for 16 hours, allowed to cool, the solvent evaporated and the polymer was dissolved in 100 mL water then extracted with CHCl$_3$ (4×300 mL). The combined organic layers dried over MgSO$_4$, and filtered. The solvent was removed and the resulting liquid was diluted with a minimal amount of methanol and precipitated in to diethyl ether. 14.8 g (72% yield) of a white powder was isolated following filtration. $^1$H NMR (400 MHz, DMSO-d$_6$, δ) 7.42, 7.29, 7.19, 4.13, 4.07, 3.7-3.3. GPC (DMF, MALS) $M_n$=8,400; PDI=1.01.

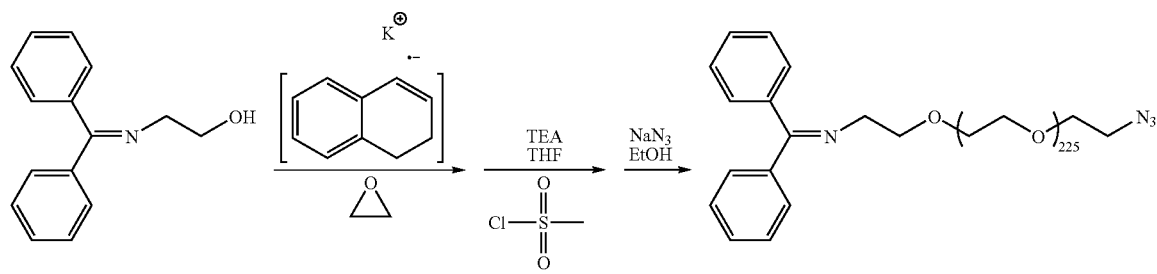

Example 10

Methods for the Removal of the Benzophenone Imine Protecting Group

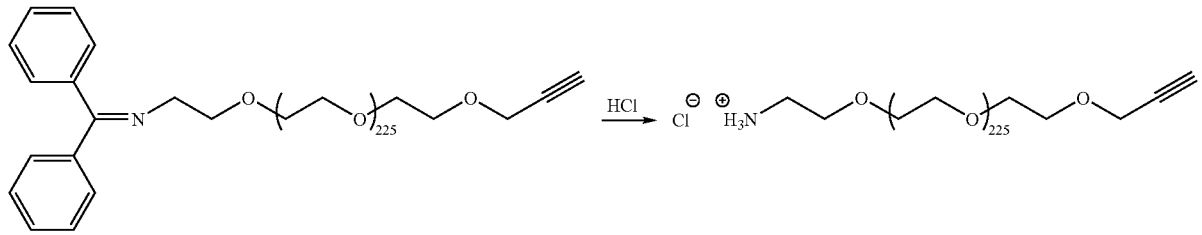

Ammonium hydrochloride-PEG-propyne

Benzophenone-imine-PEG-propyne was dissolved in 6 N HCl (150 mL) and stirred for 3 h at room temperature. The solution was extracted with $CHCl_3$ (4×300 mL) then the combined organic layers dried over $MgSO_4$, filtered and the solvent evaporated. The resulting viscous liquid was precipitated into cold diethyl ether to give a white powder. $^1H$ NMR (400 MHz, DMSO-$d_6$, δ) 8.9, 4.14, 3.7-3.3. GPC (DMF, MALS) $M_n$=11,600; PDI=1.03.

Benzophenone-imine-PEG-propyne (1 g) was dissolved in 0.5 M hydroxylamine hydrochloride in pH 5 water (20 mL). After 16 h, the solution extracted with $CHCl_3$ (4×30 mL). The combined organic layers dried over $MgSO_4$, and filtered. The solvent was removed and the resulting liquid was diluted with a minimal amount of methanol and precipitated in to diethyl ether. A white powder was isolated following filtration.

Benzophenone-imine-PEG-propyne (1 g) was dissolved in water (5 mL) and THF (5 mL). Hydroxylamine hydrochloride (0.7 g, 100 equiv) was added and the solution stirred at 50° C. After 16 h, the solution extracted with $CHCl_3$ (4×30 mL). The combined organic layers dried over $MgSO_4$, and filtered. The solvent was removed and the resulting liquid was diluted with a minimal amount of methanol and precipitated in to diethyl ether. A white powder was isolated following filtration.

Benzophenone-imine-PEG-propyne (5 g) was dissolved in 0.5 N HCl (50 mL) then silica gel (2 g) added to the stirred solution. The suspension was stirred at 40° C. for 4 hours, filtered, extracted with $CHCl_3$ (4×300 mL) then the combined organic layers dried over $MgSO_4$, filtered and the solvent evaporated. The resulting viscous liquid was precipitated into cold diethyl ether to give a white powder.

Benzophenone-imine-PEG-propyne was dissolved in water adjusted to pH 5 with dilute HCl (10 mL) and stirred for 16 h at room temperature. The solution was extracted with $CHCl_3$ (4×300 mL) then the combined organic layers dried over $MgSO_4$, filtered and the solvent evaporated. The resulting viscous liquid was precipitated into cold diethyl ether to give a white powder.

Benzophenone-imine-PEG-propyne (1 g) was dissolved in 0.2 N HCl (5 mL) and THF (5 mL) and the solution stirred at room temperature. After 16 h, the solution extracted with $CHCl_3$ (4×30 mL). The combined organic layers dried over $MgSO_4$, and filtered. The solvent was removed and the resulting liquid was diluted with a minimal amount of methanol and precipitated in to diethyl ether. A white powder was isolated following filtration.

Benzophenone-imine-PEG-propyne (1 g) was dissolved in ethanol (10 mL) then hydroxylamine hydrochloride (0.008 g, 1.1 equiv) was added and the solution stirred at reflux. After 16 h, the solution was diluted with 20 mL water then extracted with $CHCl_3$ (4×30 mL). The combined organic layers dried over $MgSO_4$, and filtered. The solvent was removed and the resulting liquid was diluted with a minimal amount of methanol and precipitated in to diethyl ether. A white powder was isolated following filtration.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

---

We claim:

1. A compound of formula I:

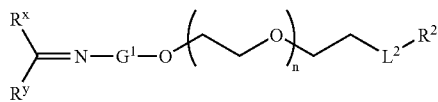

or a salt thereof, wherein:

n is about 10 to about 40, about 40 to about 60, about 60 to about 90, about 90 to about 150, about 150 to about 200, about 200 to about 250, about 300 to about 375, about 400 to about 500, about 650 to about 750, about 5 to about 10, about 5 to about 15, 50±10, 80±10, 115 ±10, 180±10, or 225±10;

—N=$R^x(R^y)$ is:

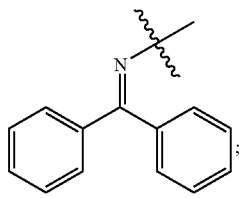

$G^1$ is a valence bond or a bivalent, saturated or unsaturated, straight or branched $C_{1-12}$ hydrocarbon chain, wherein 0-6 methylene units of the chain are independently replaced by -Cy-, or —O—;

$L^2$ is a valence bond or a bivalent, saturated or unsaturated, straight or branched $C_{1-12}$ hydrocarbon chain, wherein 0-6 methylene units of the chain are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

each R is independently hydrogen or an optionally substituted aliphatic group;

$R^2$ is hydrogen, halogen, NO$_2$, CN, N$_3$, —P(O)(OR)$_2$, —P(O)(X)$_2$, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety; and each X is independently halogen.

2. The compound according to claim 1, wherein:
$L^2$ is -Cy-, —C(O)—, —C(O)NH—, —NH—O—, —O-Cy-CH$_2$NH—, —NHC(O)—, —OCH$_2$—, —OCH$_2$C(O)—, —OCH$_2$CH$_2$C(O)—, —OCH$_2$CH$_2$O—, —OCH$_2$CH$_2$S—, —OCH$_2$CH$_2$C(O) O—, —OCH$_2$CH$_2$NH—, —OCH$_2$CH$_2$NHC(O)—, —OCH₂CH₂C(O)NH—, —O-Cy-, —O-Cy-NH—, —NHC(O)CH₂CH₂C(O)O—, —OCH₂CH₂NHC(O)CH₂CH₂C(O)O—, —O-Cy-CH₂—, —OCH₂CH₂NHC(O)CH₂OCH₂C(O)O—, —OCH₂CH₂NHC(O)CH₂OCH₂C(O)NH—, —CH₂C(O)NH—, —CH₂C(O)NHNH—, —OCH₂CH₂NHNH—, —OC(O)CH₂CH₂CH₂CH₂—, —OCH₂CH₂—, —NHC(O)CH₂CH₂—, —NHC(O)CH₂CH₂CH₂—, —OC(O)CH₂CH₂CH₂—, —O-Cy-C(O)—, —O-Cy-C(O)O—, —O-Cy-C(O)O—Cy-, —O-Cy-OCH₂CH(CH₃)C(O)O—, —O-Cy-C(O)O—, —O-Cy-OCH(CH₃)CH₂C(O)O—, —OCH₂C(O)O—, —OCH₂C(O)NH—, —OCH₂O—, —OCH₂S—, —O-Cy-S—, or —OCH₂NH—.

3. The compound according to claim 1, wherein R² is an azide-containing group, an alkyne-containing group, a group comprising a terminal alkyne moiety, an aldehyde-containing group, a group comprising a terminal hydrazine moiety, a group comprising a terminal oxyamine moiety, an epoxide-containing group, or a group comprising a terminal maleimide moiety.

4. The compound according to claim 1, wherein said compound is selected from the following formulae:

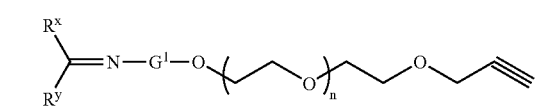
I-a

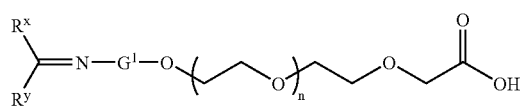
I-b

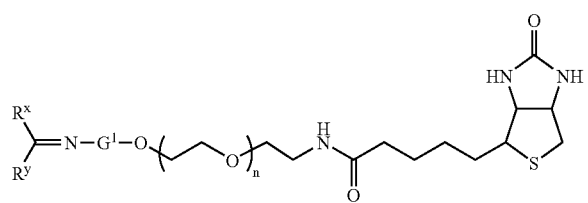
I-c

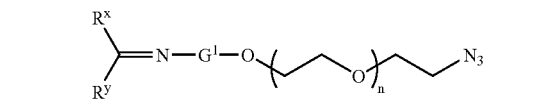
I-d

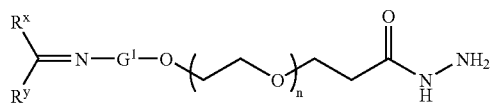
I-e

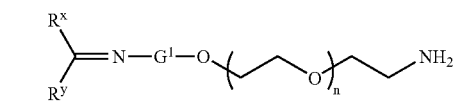
I-f

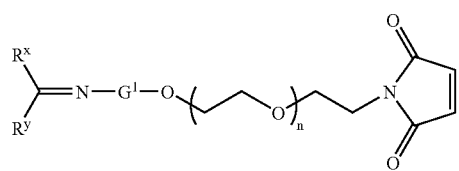
I-g

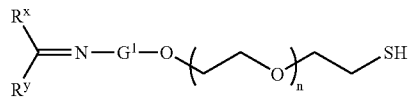
I-h

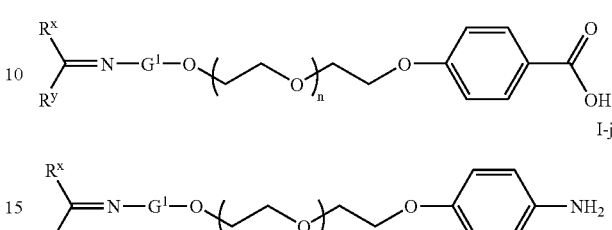
I-i

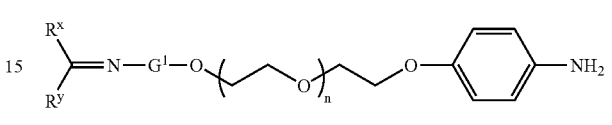
I-j

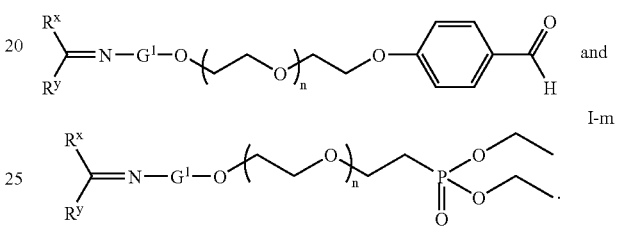
I-l and

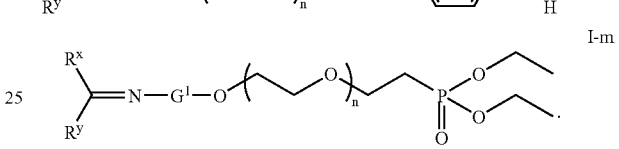
I-m

5. The compound of claim 1, selected from those depicted in Tables A and B:

TABLE A

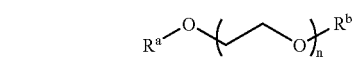

| # | Rᵃ | Rᵇ |
|---|---|---|
| 1 | 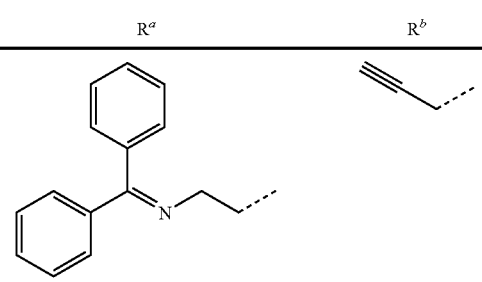 | (alkyne) |
| 2 | 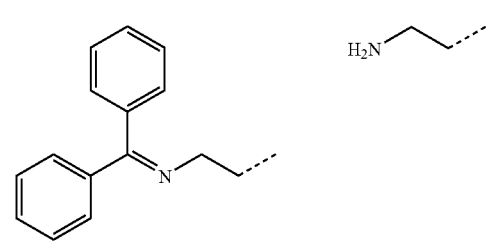 | H₂N— |
| 3 | 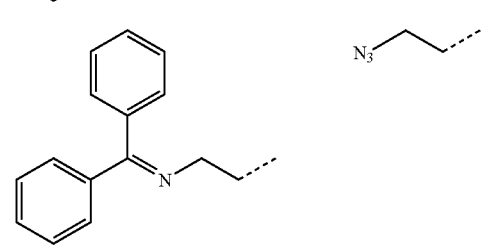 | N₃— |

TABLE A-continued $$R^a{-}O{-}(\phantom{x})_n{-}O{-}R^b$$

| # | $R^a$ | $R^b$ |
|---|---|---|
| 4 | (diphenylmethylene)amino-propyl | –CH₂CH₂–CHO |
| 5 | (diphenylmethylene)amino-propyl | –CH₂CH₂–SH |
| 6 | (diphenylmethylene)amino-propyl | exo-oxanorbornene dicarboximide-ethyl |
| 7 | (diphenylmethylene)amino-propyl | maleimido-ethyl |
| 8 | (diphenylmethylene)amino-propyl | –CH₂CH₂–OH |

TABLE B $$R^a{-}O{-}(\phantom{x})_n{-}O{-}R^b$$

| Entry | $R^a$ | $R^b$ |
|---|---|---|
| 25 | (diphenylmethylene)amino-propyl | –CH₂CH₂–O–CH₃ |

* * * * *